US006528631B1

(12) United States Patent
Cook et al.

(10) Patent No.: US 6,528,631 B1
(45) Date of Patent: Mar. 4, 2003

(54) OLIGONUCLEOTIDE-FOLATE CONJUGATES

(75) Inventors: Phillip Dan Cook, Lake San Marcos, CA (US); Muthiah Manoharan, Carlsbad, CA (US); Balkrishen Bhat, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/098,166

(22) Filed: Jun. 16, 1998

Related U.S. Application Data

(63) Continuation-in-part of application No. 08/117,363, filed on Sep. 3, 1993.

(51) Int. Cl.[7] .......................... C07H 21/02; C07H 21/04
(52) U.S. Cl. .......................... 536/23.1; 435/6; 435/91.1; 435/91.2; 514/1; 514/44; 536/22.1; 536/24.3; 536/24.33; 536/25.3
(58) Field of Search .......................... 435/6, 91.1, 91.2; 514/1, 44; 536/22.1, 23.1, 24.3, 24.33, 25.3

(56) References Cited

U.S. PATENT DOCUMENTS

| | | | |
|---|---|---|---|
| 3,687,808 A | 8/1972 | Merigan et al. | 195/28 |
| 4,469,863 A | 9/1984 | Ts'o et al. | 536/27 |
| 4,476,301 A | 10/1984 | Imbach et al. | 536/27 |
| 4,587,044 A | 5/1986 | Miller et al. | 530/211 |
| 4,605,735 A | 8/1986 | Miyoshi et al. | 536/27 |
| 4,667,025 A | 5/1987 | Miyoshi et al. | 536/27 |
| 4,689,320 A | 8/1987 | Kaji | 514/44 |
| 4,725,677 A | 2/1988 | Köster et al. | 536/27 |
| 4,762,779 A | 8/1988 | Snitman | 435/6 |
| 4,789,737 A | 12/1988 | Miyoshi et al. | 536/27 |
| 4,806,463 A | 2/1989 | Goodchild et al. | 435/5 |

(List continued on next page.)

FOREIGN PATENT DOCUMENTS

| | | |
|---|---|---|
| EP | 0 251 283 | 6/1987 |
| WO | WO 86/02929 | 5/1986 |
| WO | WO 90/10448 | 9/1990 |
| WO | WO 90/12096 | 10/1990 |
| WO | WO 91/10671 | 7/1991 |
| WO | WO 9307883 | 4/1993 |

OTHER PUBLICATIONS

Rosowsky et al. "Nucleosides. 1. 9–(3'–alkyl–3'–deoxy– – D–ribofuranosyl)adenines as lipophilic analogues of cordycepin. Synthesis and preliminary studies" Journal of Medicinal Chemistry, vol. 19, No: 11, pp. 1265–1270, Nov. 1976.*

(List continued on next page.)

*Primary Examiner*—Jezia Riley
(74) *Attorney, Agent, or Firm*—Woodcock Washburn LLP

(57) ABSTRACT

Oligonucleotide-folate conjugates are described wherein folates are conjugated to one or more sites on an oligonucleotide including the 2'-, 3'-, 5'-, nucleobase and internucleotide linkage sites. The folate can be attached via the α- or γ-carboxylate, optionally through a linking group. Methods for the regiospecific synthesis of the conjugates are disclosed.

42 Claims, 9 Drawing Sheets

U.S. PATENT DOCUMENTS

| | | |
|---|---|---|
| 4,824,941 A | 4/1989 | Gordon et al. ............... 530/403 |
| 4,828,979 A | 5/1989 | Klevan et al. .................. 435/6 |
| 4,835,263 A | 5/1989 | Nguyen et al. ................ 536/27 |
| 4,845,205 A | 7/1989 | Huynh Dinh et al. ......... 536/28 |
| 4,876,335 A | 10/1989 | Yamane et al. ............... 536/27 |
| 4,904,582 A | 2/1990 | Tullis ............................ 435/6 |
| 4,948,882 A | 8/1990 | Ruth ........................... 536/27 |
| 4,958,013 A | 9/1990 | Letsinger ..................... 536/27 |
| 4,981,957 A | 1/1991 | Lebleu et al. ................. 536/27 |
| 5,004,810 A | 4/1991 | Draper ........................ 536/27 |
| 5,013,830 A | 5/1991 | Ohtsuka et al. ............... 536/27 |
| 5,023,243 A | 6/1991 | Tullis .......................... 514/44 |
| 5,034,506 A | 7/1991 | Summerton et al. ......... 528/391 |
| 5,082,830 A | 1/1992 | Brakel et al. ................. 514/44 |
| 5,087,617 A | 2/1992 | Smith .......................... 514/44 |
| 5,098,890 A | 3/1992 | Gerwirtz et al. .............. 514/44 |
| 5,108,921 A | 4/1992 | Low et al. ............... 435/240.1 |
| 5,109,124 A | 4/1992 | Ramachandran et al. ..... 536/27 |
| 5,112,963 A | 5/1992 | Pieles et al. ................... 536/27 |
| 5,118,800 A | 6/1992 | Smith et al. .................. 536/23 |
| 5,118,802 A | 6/1992 | Smith et al. .................. 536/27 |
| 5,130,302 A | 7/1992 | Spielvogel et al. ........... 514/45 |
| 5,134,066 A | 7/1992 | Rogers et al. ................ 435/91 |
| 5,135,917 A | 8/1992 | Burch ......................... 514/44 |
| 5,138,045 A | 8/1992 | Cook et al. ................... 536/27 |
| RE34,069 E | 9/1992 | Köster et al. ................. 536/27 |
| 5,149,797 A | 9/1992 | Pederson et al. ............. 536/27 |
| 5,166,195 A | 11/1992 | Ecker ......................... 514/44 |
| 5,166,315 A | 11/1992 | Summerton et al. .......... 528/406 |
| 5,175,273 A | 12/1992 | Bischofberger et al. ...... 536/27 |
| 5,177,196 A | 1/1993 | Meyer, Jr. et al. .......... 536/22.1 |
| 5,185,444 A | 2/1993 | Summerton et al. .......... 544/81 |
| 5,188,897 A | 2/1993 | Suhadolnik et al. ..... 428/402.2 |
| 5,194,428 A | 3/1993 | Agrawal et al. ............... 514/44 |
| 5,212,295 A | 5/1993 | Cook ......................... 536/26.7 |
| 5,214,134 A | 5/1993 | Weis et al. .................. 536/25.3 |
| 5,214,136 A | 5/1993 | Lin et al. ..................... 514/44 |
| 5,216,141 A | 6/1993 | Benner ................... 536/27.13 |
| 5,218,105 A | 6/1993 | Cook et al. ............... 536/25.31 |
| 5,220,007 A | 6/1993 | Pederson et al. ........... 536/23.1 |
| 5,223,168 A | 6/1993 | Holt ........................... 252/142 |
| 5,223,618 A | 6/1993 | Cook et al. ............... 544/276 |
| 5,235,033 A | 8/1993 | Summerton et al. ......... 528/391 |
| 5,242,906 A | 9/1993 | Pagano et al. ................ 514/44 |
| 5,245,022 A | 9/1993 | Weis et al. .................. 536/24.5 |
| 5,254,469 A | 10/1993 | Warren, III et al. ......... 435/188 |
| 5,256,775 A | 10/1993 | Froehler ..................... 536/25.6 |
| 5,258,506 A | 11/1993 | Urdea ........................ 536/23.1 |
| 5,262,536 A | 11/1993 | Hobbs, Jr. ................... 546/25 |
| 5,264,423 A | 11/1993 | Cohen et al. ................. 514/44 |
| 5,264,562 A | 11/1993 | Matteucci ................... 536/23.1 |
| 5,264,564 A | 11/1993 | Matteucci ................... 536/23.1 |
| 5,272,250 A | 12/1993 | Spielvogel et al. ........... 530/300 |
| 5,276,019 A | 1/1994 | Cohen et al. ................. 514/44 |
| 5,278,302 A | 1/1994 | Caruthers et al. ........... 536/24.5 |
| 5,286,717 A | 2/1994 | Cohen et al. ................. 514/44 |
| 5,292,873 A | 3/1994 | Rokita et al. ................ 536/24.3 |
| 5,317,098 A | 5/1994 | Shizuya et al. ............. 536/23.1 |
| 5,319,080 A | 6/1994 | Leumann .................... 536/27.1 |
| 5,321,131 A | 6/1994 | Agrawal et al. ........... 536/25.34 |
| 5,359,044 A | 10/1994 | Cook et al. ................. 536/23.1 |
| 5,366,878 A | 11/1994 | Pederson et al. ........... 435/91.3 |
| 5,367,066 A | 11/1994 | Urdea et al. ............... 536/24.3 |
| 5,371,241 A | 12/1994 | Brush et al. ................. 549/220 |
| 5,378,825 A | 1/1995 | Cook et al. ............... 536/25.34 |
| 5,386,023 A | 1/1995 | Sanghvi et al. ............. 536/25.3 |
| 5,391,723 A | 2/1995 | Priest ........................ 536/23.1 |
| 5,393,878 A | 2/1995 | Leumann .................... 536/28.2 |
| 5,399,676 A | 3/1995 | Froehler .................... 536/23.1 |
| 5,403,711 A | 4/1995 | Walder et al. ................ 435/6 |
| 5,405,938 A | 4/1995 | Summerton et al. ......... 528/406 |
| 5,405,939 A | 4/1995 | Suhadolnik et al. ......... 530/322 |
| 5,414,077 A | 5/1995 | Lin et al. .................... 536/24.3 |
| 5,416,016 A | 5/1995 | Low et al. ............... 435/240.1 |
| 5,416,203 A | 5/1995 | Letsinger ................. 533/25.34 |
| 5,432,272 A | 7/1995 | Benner ....................... 536/25.3 |
| 5,434,257 A | 7/1995 | Matteucci et al. .......... 536/24.3 |
| 5,446,137 A | 8/1995 | Maag et al. ................ 536/23.1 |
| 5,451,463 A | 9/1995 | Nelson et al. ............... 428/402 |
| 5,453,496 A | 9/1995 | Caruthers et al. ........... 536/24.5 |
| 5,455,233 A | 10/1995 | Spielvogel et al. ........... 514/44 |
| 5,457,187 A | 10/1995 | Gmeiner et al. ........... 536/25.5 |
| 5,457,191 A | 10/1995 | Cook et al. ............... 536/27.13 |
| 5,459,255 A | 10/1995 | Cook et al. ............... 536/27.13 |
| 5,466,677 A | 11/1995 | Baxter et al. ................. 514/44 |
| 5,466,786 A | 11/1995 | Buhr et al. ................ 536/26.26 |
| 5,470,967 A | 11/1995 | Huie et al. ................. 536/24.3 |
| 5,476,925 A | 12/1995 | Letsinger et al. ........... 536/23.1 |
| 5,484,908 A | 1/1996 | Froehler et al. .......... 536/24.31 |
| 5,486,603 A | 1/1996 | Buhr ........................ 536/24.3 |
| 5,489,677 A | 2/1996 | Sanghvi et al. ............. 536/22.1 |
| 5,491,133 A | 2/1996 | Walder et al. ................ 514/44 |
| 5,502,177 A | 3/1996 | Matteucci et al. ............ 536/260 |
| 5,506,351 A | 4/1996 | McGee ....................... 536/55.3 |
| 5,510,475 A | 4/1996 | Agrawal et al. ............ 536/24.3 |
| 5,512,439 A | 4/1996 | Hornes et al. ................. 435/6 |
| 5,512,667 A | 4/1996 | Reed et al. ............... 536/24.31 |
| 5,514,785 A | 5/1996 | Van Ness et al. ........... 536/22.1 |
| 5,519,126 A | 5/1996 | Hecht ........................ 536/24.3 |
| 5,519,134 A | 5/1996 | Acevedo et al. ............ 544/243 |
| 5,521,302 A | 5/1996 | Cook ........................ 536/25.31 |
| 5,525,465 A | 6/1996 | Haralambidis et al. ......... 435/6 |
| 5,525,711 A | 6/1996 | Hawkins et al. ........... 536/22.1 |
| 5,536,821 A | 7/1996 | Agrawal et al. ............ 536/22.1 |
| 5,539,082 A | 7/1996 | Nielsen et al. .............. 530/300 |
| 5,541,306 A | 7/1996 | Agrawal et al. ............ 536/22.1 |
| 5,541,307 A | 7/1996 | Cook et al. ................. 536/23.1 |
| 5,541,313 A | 7/1996 | Ruth ........................ 536/24.3 |
| 5,543,508 A | 8/1996 | Haseloff et al. ............ 536/23.2 |
| 5,545,729 A | 8/1996 | Goodchild et al. ......... 536/24.5 |
| 5,545,730 A | 8/1996 | Urdea et al. .............. 536/28.51 |
| 5,550,111 A | 8/1996 | Suhadolnik et al. .......... 514/44 |
| 5,552,538 A | 9/1996 | Urdea et al. ............... 536/24.3 |
| 5,552,540 A | 9/1996 | Haralambidis ........... 536/25.34 |
| 5,554,746 A | 9/1996 | Ravikumar et al. ......... 540/200 |
| 5,561,225 A | 10/1996 | Maddry et al. ............. 536/23.1 |
| 5,563,253 A | 10/1996 | Agrawal et al. ............ 536/22.1 |
| 5,565,350 A | 10/1996 | Kmiec ..................... 435/172.3 |
| 5,565,552 A | 10/1996 | Magda et al. ................ 534/11 |
| 5,567,810 A | 10/1996 | Weis et al. ................. 536/25.3 |
| 5,567,811 A | 10/1996 | Misiura et al. ........... 536/25.34 |
| 5,571,799 A | 11/1996 | Tkachuk et al. .............. 514/47 |
| 5,571,902 A | 11/1996 | Ravikumar et al. ........ 536/22.1 |
| 5,574,142 A | 11/1996 | Meyer, Jr. et al. ......... 536/23.1 |
| 5,576,427 A | 11/1996 | Cook et al. ................. 536/23.1 |
| 5,578,717 A | 11/1996 | Urdea et al. ............... 536/26.1 |
| 5,578,718 A | 11/1996 | Cook et al. ............... 536/27.21 |
| 5,580,731 A | 12/1996 | Chang et al. .................. 435/6 |
| 5,585,481 A | 12/1996 | Arnold, Jr. et al. ...... 536/25.33 |
| 5,587,361 A | 12/1996 | Cook et al. .................. 514/44 |
| 5,587,371 A | 12/1996 | Sessler et al. .............. 514/185 |
| 5,587,469 A | 12/1996 | Cook et al. ................. 536/23.1 |
| 5,587,470 A | 12/1996 | Cook et al. ................. 536/23.1 |
| 5,591,584 A | 1/1997 | Chang et al. .................. 435/6 |
| 5,591,722 A | 1/1997 | Montgomery et al. ......... 514/45 |
| 5,594,121 A | 1/1997 | Froehler et al. ............ 536/23.5 |
| 5,595,726 A | 1/1997 | Magda et al. .............. 424/9.61 |
| 5,596,086 A | 1/1997 | Matteucci et al. .......... 536/22.1 |
| 5,596,091 A | 1/1997 | Switzer ..................... 536/24.5 |
| 5,597,696 A | 1/1997 | Linn et al. .................... 435/6 |
| 5,597,909 A | 1/1997 | Urdea et al. ............... 536/24.3 |

| | | |
|---|---|---|
| 5,599,797 A | 2/1997 | Cook et al. ............... 514/44 |
| 5,599,923 A | 2/1997 | Sessler et al. ............ 540/145 |
| 5,599,928 A | 2/1997 | Hemmi et al. ............ 540/474 |
| 5,602,240 A | 2/1997 | De Mesmaeker et al. . 536/23.1 |
| 5,608,046 A | 3/1997 | Cook et al. ............... 536/23.1 |
| 5,610,289 A | 3/1997 | Cook et al. .............. 536/25.34 |
| 5,610,300 A | 3/1997 | Altmann et al. ............ 544/244 |
| 5,614,617 A | 3/1997 | Cook et al. ............... 536/23.1 |
| 5,618,704 A | 4/1997 | Sanghvi et al. ............ 435/91.5 |
| 5,623,065 A | 4/1997 | Cook et al. ............... 536/23.1 |
| 5,623,070 A | 4/1997 | Cook et al. ............... 536/27.6 |
| 5,625,050 A | 4/1997 | Beaton et al. ............. 536/24.1 |
| 5,627,053 A | 5/1997 | Usman et al. ............ 435/91.1 |
| 5,633,360 A | 5/1997 | Bischofberger et al. ... 536/22.1 |
| 5,639,873 A | 6/1997 | Barascut et al. ........... 536/25.3 |
| 5,646,265 A | 7/1997 | McGee .................... 536/25.34 |
| 5,652,355 A | 7/1997 | Metelev et al. ........... 536/24.5 |
| 5,652,356 A | 7/1997 | Agrawal .................. 536/24.5 |
| 5,658,873 A | 8/1997 | Bertsch-Frank et al. .... 510/375 |
| 5,663,312 A | 9/1997 | Chaturvedula ............. 536/22.1 |
| 5,670,633 A | 9/1997 | Cook et al. ............... 536/23.1 |
| 5,677,437 A | 10/1997 | Teng et al. ............... 536/23.1 |
| 5,677,439 A | 10/1997 | Weis et al. ............... 536/23.1 |
| 5,681,941 A | 10/1997 | Cook et al. ............... 536/23.1 |
| 5,688,941 A | 11/1997 | Cook et al. ............... 536/25.3 |
| 5,697,248 A | 12/1997 | Brown .................... 73/290 V |
| 5,700,920 A | 12/1997 | Altmann et al. ............ 536/221 |
| 5,700,922 A | 12/1997 | Cook ...................... 536/23.1 |
| 5,714,331 A | 2/1998 | Buchardt et al. ............. 435/6 |
| 5,719,262 A | 2/1998 | Buchardt et al. ........... 530/300 |
| 5,750,692 A | 5/1998 | Cook et al. ............... 536/23.1 |
| 5,859,221 A | 1/1999 | Cook et al. ............... 536/22.1 |
| 5,955,589 A | 9/1999 | Cook ...................... 536/23.1 |
| 6,262,241 B1 | 7/2001 | Cook et al. ............... 536/22.1 |
| 6,127,533 A1 | 10/2001 | Cook et al. ............... 536/23.1 |

OTHER PUBLICATIONS

Nomura, Y. et al., "Site–specific introduction of functional groups into phosphodiester oligonucleotides and their thermal stability and nuclease–resistance properties," *Nucleic Acids Research*, 1997, 25, pp. 2784–2791.

Wasner, M. et al., "6–Aminohexanoyl–Linked Conjugates of Monomeric and Trimeric Cordycepin", *Helvetica Chimica Acta*, 1997, 80, pp. 1061–1071.

Habus, I. et al., "A Mild and Efficient Solid–Support Synthesis of Novel Oligonucleotide Conjugates," *Bioconj. Chem.*, 1998, 9, 283–291.

Asseline, U. et al., "Nucleic acid–binding molecules with high affinity and base sequence specificity: Intercalating agents covalently linked to oligodeoxynucleotides", *Proc. Natl. Acad. Sci.*, 1984, 81, 3297–3301.

Beaucage, S.L. et al., "The Functionalization of Oligonucleotides Via Phosphoramidite Derivatives," *Tetrahedron*, 1993, 49(10), 1925–1963.

Beaucage, S.L. et al., "The Synthesis of Specific Ribonucleotides and Unrelated Phosphorylated Biomolecules by the Phosphoramidite Method," *Tetrahedron*, 1993, 49(46), 10441–10488.

Beaucage, S.L. et al., "Advanced in the Synthesis of Oligonucleotides by the Phosphoramidite Approach", *Tetrahedron*, 1992, 48, 2223–2311.

Buzayan, J.M. et al., "Satellite tobacco ringspot virus RNA: A subset of the RNA sequence is sufficient for autolytic processing", *Proc. Natl. Acad. Sci. USA*, 1986, 83, 8859–8862.

Chollet, A., "Selective Attachment of Oligonucleotides to Interleukin 1β and Targeted Delivery to Cells", *Nucleosides & Nucleotides*, 1990, 9, 957–966.

Corey, D.R. et al., "Sequence–Selective Hydrolysis of Duplex DNA by and Oligonucleotide–Directed Nuclease", *J. Am. Chem. Soc.*, 1989, 111, 8523–8525.

Corey, D.R. et al., "Generation of a Hybrid Sequence–Specific Single–Stranded Deoxyribonuclease", *Science*, 1987, 238, 1401–1403.

Crooke, S.T. et al., "Pharmacokinetic Properties of Several Novel Oligonucleotide Analogs in mice", *J. Pharmacol. Exp. Therapeutics*, 1996, 277, 923–937.

Dingwell et al., "Protein Import into the Cell Nucleus", *Ann. Rev. Cell Biol.*, 1986, 2, 367–390.

Dreyer, G.B. et al., "Sequence–specific cleavage of single–stranded DNA: Oligodeoxynucleotide–EDTA·Fe(II)", *Proc. Natl. Acad. Sci.*, 1985, 82, 968–972.

Englisch, U. et al., "Chemically Modified Oligonucleotiodes as Probes and Inhibitors", *Angew. Chem. Int. Ed. Eng.*, 1991, 30, 613–629.

Forster, A.C. et al., "Self–Cleavage of Virusoid RNA is Performed by the Proposed 55–Nucleotide Active Site", *Cell*, 1987, 50, 9–16.

Freier, S.M. et al., "The ups and downs of nucleic acid duplex stability: structure–stability studies on chemically–modified DNA:RNA duplexes", *Nucl. Acids Res.*, 1997, 25, 4429–4443.

Guerra, F.I. et al., "Synthetic 6–Glucosyl Phospholipid as a Drug Transport System", *Tetrahedron Letts.*, 1987, 28, 3581–3584.

Haralambidis, J. et al., "Preparation of base–modified nucleósides suitable for non–radioactive label attachment and their incorporation into synthetic oligodeoxyribonucleotides", *Nucl. Acids. Res.*, 1987, 15, 4857–4876.

Haralambidis, J. et al., "The Solid Phase Synthesis of Oligonucleotides Containing a 3'–Peptide Moeity", *Tetrahedron Letts.*, 1987, 28, 5199–5202.

Jablonski, E. et al., "Preparation of oligodeoxynucleotide—alkaline phosphatase conjugates and their use as hybridization probes", *Nucl. Acids Res.*, 1986, 14, 6115–6128.

Juby, C.D. et al., "Facile Preparation of 3'Oligonucleotide–Peptide Conjugates", *Tetrahedron Letts.*, 1991, 32, 879–882.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kornberg, A. et al., *DNA Replication*, 1980, W.H. Freeman & Co., San Francisco, 4–7.

Krieg, A.M. et al., "Uptake of Oligodeoxyribonucleotides by Lymphoid Cells Is Heterogenous and Inducible", *Antisense Res. & Dev.*, 1991, 1, 161–171.

Kroschwitz, J.I., "Polynucleotides", *Concise Encyclopedia of Polymer Science and Engineering*, 1990, John Wiley & Sons, New York, 858–859.

Lehninger, "The amino acid building blocks of proteins", *Biochemistry*, Second Edition, Worth Publishers, Inc., 1975, Ch. 4, 73–77.

Lemairte, M. et al., "Specific antiviral activity of a poly(L–l–ysine)–conjugated oligodeoxyribonucleotide sequence complementrary to vesicular stomatitis virus N protein mRNA initiation site", *Proc. Natl. Acad. Sci.*, 1987, 84, 648–652.

Leonetti, J.P. et al., "Biological Activity of Oligonucleotide–Poly(L–lysine) Conjugates: Mechanism of Cell Uptake", *Biconjugate Chem.*, 1990, 1, 149–153.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Manoharan, M. et al., "Lipidic Nucleic Acids", *Tetrahedron Letts.*, 1995, 36, 3651–3654.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Oligonucleotide Conjugates: Alteration of the Pharmacokinetic Properties of Antisense Agents", *Nucleosides and Nucleotides*, 1995, 14, 969–973.

Miller, P.S. et al., "A New approach to chemotherapy based on molecular biology and nucleic acid chemistry: Matagen (masking tape for gene expression)", *Anti–Cancer Drug Des.*, 1987, 2, 117–128.

Martin, P., "Ein neuer Zugang zu 2'–O–Alkylribonucleosiden und Eigenschaften deren Oligonucleotide", *Helvetica Chemica Acta*, 1995, 78, 486–504 (English summary included).

Mishra, R.K. et al., "Improved leishmanicidal effect of phosphorotioate antisense oligonucleotides by LDL–medicated delivery", *Biochim. Et Biophysica*, 1995, 1264, 229–237.

Nelson, P.S. et al., "Bifunctional oligonucleotide probes synthesized using a novel CPG: support are able to detect single base pair mutations", *Nucl. Acids Res.*, 1989, 17, 7187–7195.

Nielsen, P.E. et al., "Sequence–Selective Recognition of DNA by Strand Displacement with a Thymine–Substituted Polyamide", *Science*, 1991, 254, 1497–1500.

Oberhauser, B. et al., "Effective incorporation of 2'–0–methyl–oligonucleotides into liposomes and enhanced cell association through modification with thiocholesterol", *Nucl. Acids Res.*, 1992, 20, 533–538.

Ramirez, F. et al., "Nucleotidophospholipids: Oligonucleotide Derrivatives with Membrane–Recognition Groups", *J. Am. Chem. Soc.*, 1982, 104, 5483–5486.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Sanghvi, Y.S.,"Heterocyclic Base Modifications in Nucleic acids and their Applications in Antisense Oligonucleotides", *Antisense Research and Applications*, Crooke, S.T. et al. (eds.), CRC Press, 1993, Chapter 15, 273–288.

Shea, R.G. et al., "Synthesis, hybridization properties and antiviral activity of lipid–oligodeoxynucleotide conjugates", *Nucl. Acids Res.*, 1990, 18, 3777–3783.

Svinarchuk, F.P. et al., "Inhibition of HIV proliferation in MT–4 cells by antisense oligonucleotide conjugated to lipophilic groups", *Biochimie*, 1993, 79, 49–54.

Telser, J. et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", *J. Am. Chem. Soc.*, 1989, 111, 6966–6975.

Wychowski, C. et al., "The Intranuclear Location of Simian Virus 40 Polypeptides VP2 and VP3 Depends on a Specific Amino Acid Sequence", *J. Virology*, 1987, 61, 3862–3869.

Yamana, K. et al., "Synthesis and Interactive Properties of an Oligonucleotide with Anthraquinone at the Sugar Frament", *Biconjugate Chem*, 1990, 1, 319–324.

Yoneda et al., "Synthetic Peptides Containing a Region of SV40 Large T–Antigen Involved in Nuclear Localization Direct the Transport of Proteins into the Nucleus", *Exp. Cell Res.*, 1987, 170, 439–452.

Zhang, Z. et al., "Uptake of N–(4'–pyridoxyl)amines and release of amines by renal cells: A model for transporter–enhanced delivery of bioactive compounds", *Proc. Natl. Acad. Sci.*, 1991, 88, 10407–10410.

Zuckermann, R.N. et al., "Site–Selective Cleavage of RNA by a Hybrid Enzyme", *J. Am. Chem. Soc.*, 1988, 110, 1614–1615.

* cited by examiner

α-isomer of folic acid-nucleoside conjugate

N²-ibu-N¹⁰ trifluoroacetyl Pteroic Acid

43, R = CH₃

Phosphitylation

44

Fully protected nucleoside folic acid γ-conjugate phosphoramidite, 66% yield

OLIGONUCLEOTIDE-FOLATE CONJUGATES

CROSS REFERENCE TO RELATED APPLICATIONS

This application is a continuation in part of copending U.S. application Ser. No. 08/117,363, filed Sep. 3, 1993.

FIELD OF THE INVENTION

This present invention is directed to mononucleosides and oligonucleotides that are conjugated to folic acid, related folates, antifolates and analogs thereof. The present invention also provides methods for the preparation of the mononucleoside and oligonucleotide conjugates.

BACKGROUND OF THE INVENTION

Protein synthesis is directed by nucleic acids through the intermediacy of messenger RNA (mRNA). Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally occurring events that provide the disruption of the nucleic acid function, discussed by Cohen in *Oligonucleotides: Antisense Inhibitors of Gene Expression*, CRC Press, Inc., Boca Raton, Fla. (1989) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides: Miller, P. S. and Ts'O, P. O. P. (1987) *Anti-Cancer Drug Design*, 2:117–128, and α-anomer oligonucleotides are the two most extensively studied antisense agents which are thought to disrupt nucleic acid function by hybridization arrest.

Another means by which antisense oligonucleotides disrupt nucleic acid function is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research applications and potential therapeutic purposes. At least for therapeutic purposes, the antisense oligonucleotides and oligonucleotide analogs must be transported across cell membranes or taken up by cells to exhibit their activity. However, due to the large size and unfavorable charge-size ratio of oligonucleotides, their cellular uptake is very limited. Numerous efforts have focused on increasing this membrane permeability and cellular delivery of oligonucleotides.

Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate mediated transformation.

However, many of these techniques are limited by the types of cells in which transmembrane transport is enabled and by the conditions needed for achieving such transport. An alternative that is particularly attractive for the transmembrane delivery of oligonucleotides is the modification of the physico-chemical properties of oligonucleotides via conjugation to a molecule that facilitates transport.

One method for increasing membrane or cellular transport of oligonucleotides is the attachment of a pendant lipophilic group. Ramirez, F., Mandal, S. B. and Marecek, J. F., (1982) *J. Am. Chem. Soc.*, 104:5483, introduced the phospholipid group 5'-O-(1,2-di-O-myristoyl-sn-glycero-3-phosphoryl) into the dimer TpT independently at the 3' and 5' positions. Subsequently Shea, R. G., Marsters, J. C. and Bischofberger, N. (1990), *Nuc. Acids Res.*, 18:3777, disclosed oligonucleotides having a 1,2-di-O-hexyldecyl-rac-glycerol group linked to a 5'-phosphate on the 5'-terminus of the oligonucleotide. Certain of the Shea et. al. authors also disclosed these and other compounds in patent application PCT/US90/01002. A further glucosyl phospholipid was disclosed by Guerra, F. I., Neumann, J. M. and Hynh-Dinh, T. (1987), *Tetrahedron Letters*, 28:3581.

In other work, a cholesteryl group was attached to the inter-nucleotide linkage between the first and second nucleotides (from the 3' terminus) of an oligonucleotide. This work is disclosed in U.S. Pat. No. 4,958,013 and further in Letsinger, R. L., Zhang, G., Sun, D. K., Ikeuchi, T. and Sarin, P. S. (1989), *Proc. Natl. Acad. Sci. USA*, 86:6553. Additional approaches to the delivery and study of oligonucleotides have involved the conjugation of a variety of other molecules and reporter groups. The aromatic intercalating agent anthraquinone was attached to the 2' position of a sugar fragment of an oligonucleotide as reported by Yamana, K., Nishijima, Y., Ikeda, T., Gokota, T. Ozaki, H., Nakano, H., Sangen, O. and Shimidze, T. (1990) *Bioconjugate Chem.*, 1:319; Lemairte, M., Bayard, B. and Lebleu, B. (1986), *Proc. Natl. Acad. Sci. USA*, 84:648; and Leonetti, J.-P., Degols, G. and Lebleu, B. (1990), *Bioconjugate Chem.*, 1:149. Lysine and polylysines have also been conjugated to oligonucleotides to improve their charge-size characteristics. The poly(L-lysine) was linked to the oligonucleotide via periodate oxidation of the 3'-terminal ribose followed by reduction and coupling through a N-morpholine ring. Oligonucleotide-poly(L-lysine) conjugates are described in European Patent application 87109348.0. In this instance the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide as is described by Corey, D. R. and Schultz, P. G. (1987), *Science*, 238:1401; Zuckermann, R. N., Corey, D. R., and Schultz, P. G. (1988), *J. Am. Chem. Soc.*, 110:1614; and Corey, D. R., Pei, D. and Schultz, P. G. (1989), *J. Am. Chem. Soc.*, 111:8524.

Nelson, P. S., Frye, R. A. and Liu, E. (1989), *Nuc. Acids Res.*, 17:7187 describe a linking reagent for attaching biotin to the 3'-terminus of an oligonucleotide. This reagent, N-Fmoc-O-DMT-3-amino-1,2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy, C. D., Richardson,. C. D. and Brousseau, R. (1991), *Tetrahedron Letters*, 32:879. A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg, A. M., Gmelig-Meyling, F., Gourley, M. F., Kisch, W. J., Chrisey, L. A. and Steinberg, A. D. (1991), *Antisense Research and Development*, 1:161 to link fluorescein to the 5'-terminus of an oligonucleotide. Other compounds of interest have also been linked to the 3'-terminus of an oligonucleotide. Asseline, U., Delaure, M., Lancelot, G., Toulme, F., Thuong, N. T., Montenay-Garestier, T. and Helene, C. (1984), *Proc. Natl. Acad. Sci. USA*, 81:3297 described linking acridine on the 3'-terminal phosphate group of an poly (Tp) oligonucleotide via a polymethylene linkage. Haralambidis, J., Duncan, L. and Tregear, G. W. (1987), *Tetrahedron Letters*, 28:5199 report building a peptide on a solid state support and then linking an oligonucleotide to that peptide via the 3' hydroxyl group of the 3' terminal nucleotide of the oligonucleotide. Chollet, A. (1990), *Nucleosides & Nucleotides*, 9:957 attached an Aminolink 2 (Applied Biosystems, Foster City, Calif.) to the 5' terminal phosphate of an oligonucleotide. They then used the bifunctional linking group SMPB (Pierce Chemical Co., Rockford, Ill.) to link an interleukin protein to the oligonucleotide.

Conjugation of lipids, reporters, peptides and other molecules to oligonucleotides is not limited to the terminal 3' and 5'-positions. A wide variety of conjugates have also been reported in the literature wherein attachment is performed at any one or more of the 2'-positions on the nucleotide building blocks of the oligonucleotide. Further conjugates have also been reported wherein attachment occurs on the internucleotide linkage or on one of the atoms of the nucleobase of any one of the nucleotide units of the oligonucleotide. For example, an EDTA iron complex has been linked to the 5 position of a pyrimidine nucleoside as reported by Dreyer, G. B. and Dervan, P. B. (1985), *Proc. Natl. Acad. Sci. USA*, 82:968. Fluorescein has been linked to an oligonucleotide in the same manner as reported by Haralambidis, J., Chai, M. and Tregear, G. W. (1987), *Nucleic Acid Research*, 15:4857 and biotin in the same manner as described in PCT application PCT/US/02198. Fluorescein, biotin and pyrene were also linked in the same manner as reported by Telser, J., Cruickshank, K. A., Morrision, L. E. and Netzel, T. L. (1989), *J. Am. Chem. Soc.*, 111:6966. A commercial reagent, Amino-Modifier-dT, from Glen Research Corporation (Sterling, Va.) can be utilized to introduce pyrimidine nucleotides bearing similar linking groups into oligonucleotides.

Manoharan et al. PCT Application WO 93/07883, have also reported the conjugation of oligonucleotides with a variety of molecules such as steroids, reporter molecules, reporter enzymes, vitamins, non-aromatic lipophilic molecules, chelators, porphyrins, intercalators, peptides and proteins through the intermediacy of varied linking groups, such as ω-aminoalkoxy and ω-aminoalkylamino groups. Conjugation has been reported at the 3'-, 5'-, 2'-, internucleotide linkage and nucleobase positions of oligonucleotides. Such oligonucleotide conjugates are expected to have improved physico-chemical properties that facilitated their uptake and delivery into cells as demonstrated by in vitro experiments.

The intracellular and intranuclear delivery of nucleic acids and oligonucleotides, however, is still a challenge. Most often, penetration of heretofore reported oligonucleotide conjugates has been found to be limited. This has typically been a problem because such conjugates have generally been designed to improve the passive absorption of the oligonucleotides where the size, physico-chemical properties and extra-cellular concentration of the conjugate play important limiting roles. This coupled with the limited extra-cellular stability of nucleic acids and oligonucleotides demands the development of novel conjugates that will deliver higher levels of nucleic acids and oligonucleotides into specific tissues and targeted cells. One such approach for delivering oligonucleotides, is to exploit the active transport mechanism of receptor mediated endocytosis.

Unlike many of the methods mentioned above, receptor mediated endocytotic activity can be used successfully both in vitro and in vivo. This mechanism of uptake involves the movement of ligands bound to membrane receptors into the interior of an area that is enveloped by the membrane via invagination of the membrane structure. This process is initiated via activation of a cell-surface or membrane receptor following binding of a specific ligand to the receptor. Many receptor mediated endocytotic systems are known and have been studied, including those that recognize sugars such as galactose, mannose, mannose-6-phosphate, asialoglycoprotein, vitamin B12, insulin and epidermal growth factor (EGF). Receptor mediated endocytosis has been well studied and is known to be a critical pathway for the uptake and internalization of a variety of cellular nutrients. These are highly developed mechanisms because of their critical role in providing nutrients to cells and in maintaining cellular physiology. Thus many examples of the utilization of receptor mediated endocytosis pathways for the delivery of drugs, proteins, nucleic acids and other molecules to cells are known. One way in which this has been applied is the conjugation of essential nutrients that are actively transported into cells with the drug or molecule of interest. The transporters or receptors involved in the uptake are capable of recognizing the nutrient portion of the conjugate and ferrying the entire conjugate into the cell. Examples of nutrients that are actively transported into cells and that may be of use in conjugates include, but are not limited to, folic acid, vitamin B6, cholesterol and vitamin B12. Such molecules have been conjugated to macromolecules such as nucleic acids and oligonucleotides to afford conjugates that exhibit improved cellular penetration. Manorharan et al., PCT Application WO 93/07883; Low et al., U.S. Pat. No. 5,108,921, U.S. Pat. No. 5,416,016.

Many vitamins possess an acid or alcohol functionality that is readily modified for conjugation to oligonucleotides. For example, conjugation of an N-hydroxy succinimide ester of an acid moiety of retinoic acid to an amine function on a linker pendant to an oliogonucleotide resulted in a oligonucleotide-Vitamin A conjugate attached via an amide bond. Retinol has been converted to its phosphoramidite and conjugated to the 5'-terminus of oligonucleotides via a phosphodiester or phosphorothioate linkage. Likewise, vitamin E and vitamin B6 may also be conjugated to oligonucleotides to improve transport into cells.

Pyridoxal (vitamin $B_6$) has specific $B_6$-binding proteins. The role of these proteins in pyridoxal transport has been studied by Zhang and McCormick, *Proc. Natl. Acad. Sci. USA*, 1991 88, 10407. Zhang and McCormick also have shown that a series of N-(4'-pyridoxyl)amines, in which several synthetic amines were conjugated at the 4'-position of pyridoxal, are able to enter cells by a process facilitated by the B6 transporter. They also demonstrated the release of these synthetic amines within the cell. Other pyridoxal family members include pyridoxine, pyridoxamine, pyridoxal phosphate, and pyridoxic acid. Pyridoxic acid, niacin, pantothenic acid, biotin, folic acid and ascorbic acid can be conjugated to oligonucleotides using N-hydroxysuccinimide esters that are reactive with aminolinkers located on the oligonucleotide, as described above for retinoic acid.

Folic acid and its various forms, such as dihydrofolate and tetrahydrofolate, are essential vitamins that are crucial for the biosynthesis of nucleic acids and therefore are critical to the survival and proliferation of cells. Folate cofactors play an important role in the one-carbon transfers that are critical for the biosynthesis of pyrimidine nucleosides. Cells therefore have a sophisticated system of transporting folates into the cytoplasm. Uptake of folates occurs by two different pathways depending on the cell type. Cells expressing a carrier or transporter for folate that exhibits a low affinity ($Kd\sim10^{-6}$ M) for the vitamin prefer reduced over oxidized forms of folate. Cells that express membrane receptors called folate binding protein (FBP), in contrast, exhibit high binding affinity ($Kd\sim10^{-9}$ M) and prefer the oxidized form of the vitamin. This latter receptor is believed to mediate the uptake of folates into the cytoplasm via endocytosis.

The use of biotin conjugates and also folic acid conjugates to enhance transmembrane transport of exogenous molecules, including oligonucleotides, has been reported by Low et al., U.S. Pat. No. 5,108,921; U.S. Pat. No. 5,416,016; PCT Application WO 90/12096. Folic acid was conjugated to 3'-aminoalkyl-oligonucleotides at their 3'-terminus via carbodiimide chemistry. The multiplicity of folate receptors on membrane surfaces of most cells and the associated receptor mediated endocytotic processes were implicated in the enhanced transport of these oligonucleotide-folic acid conjugates into cells. There are however, several limitations to this approach for the conjugation of folic acid to oligonucleotides.

Folic acid and many related folates and antifolates exhibit very poor solubility that hinders the effective conjugation of folic acid to oligonucleotides and subsequent purification of oligonucleotide-folic acid conjugates. Further folic acid bears two reactive carboxylic acid groups that are just as likely to react with the terminal amino group of the 3-aminoalkyl-oligonucleotide. Thus conjugation will typically result in a mixture of α- and γ-conjugates arising from the reaction of the α-carboxylate and the γ-carboxylate of the glutamic acid portion of the folic acid molecule. This poses difficulties from the standpoint of characterizing the conjugate and further from the standpoint of polyglutamylation of folates. Polyglutamylation of folates is a well recognized phenomenon that has significant implications on the transport, localization and activity of folates. Since polyglutamylation rates differ significantly between the α- and γ-carboxylates, the use of poorly defined mixtures of oligonucleotide-folate conjugates, as obtained from the Low et al. procedure, U.S. Pat. No. 5,108,921, will lead to variable transport and concentration of the conjugate. Further, the conjugation of folates onto one end of an oligonucleotide may be a disadvantage because of the known propensity of exonucleases to rapidly cleave oligonucleotides by excising the terminal residues. Also, it has been observed that oligonucleotide-folic acid conjugates prepared in this fashion are light sensitive.

Therefore, there is a clear need for new oligonucleotide-folate conjugates, and methods for their preparation, that address the shortcomings of oligonucleotide conjugates as described above. The present invention is directed to this very important end.

SUMMARY OF THE INVENTION

The present invention provides novel approaches to the facile synthesis of nucleoside- and oligonucleotide-folate conjugates via a step-wise construction of the folate conjugate. The methods of the present invention are broadly applicable to the attachment of a wide variety of folates at any one of many possible sites of attachment on oligonucleotides.

In accordance with the present invention, synthetic methods are provided comprising the steps of:
(a) providing a compound of Formula IA, IB, IC or ID:

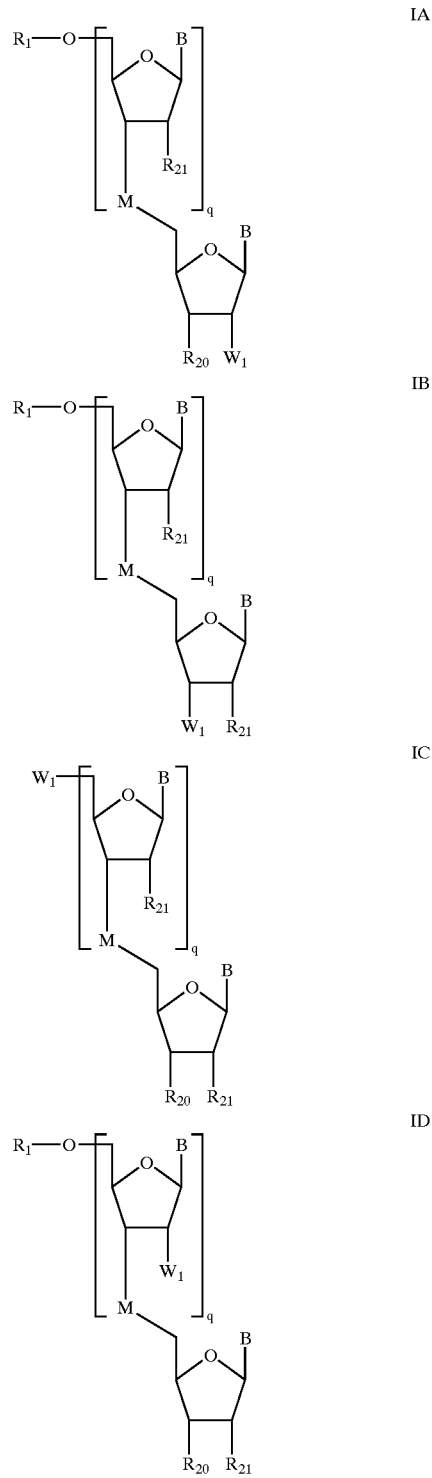

wherein:

W₁ is a linking group, O, NH or S, with a linking group being preferred;

R₁ is H or a hydroxyl protecting group;

B is a nucleobase;

each $R_{21}$ is H, OH, F, or a group of formula Z—$R_{22}$—$(R_{23})_v$;

Z is O, S, NH, or N—$R_{22}$—$(R_{23})_v$ $R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

v is from 0 to about 10;

or $R_{21}$ has one of the formulas:

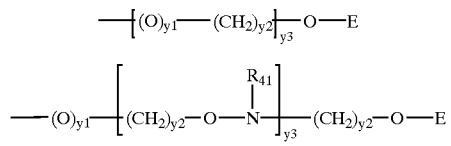

wherein:

y1 is 0 or 1;

y2 is 0 to 10;

y3 is 1 to 10;

E is $N(R_{41})(R_{42})$ or $N=C(R_{41})(R_{42})$;

each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heterotom selected from N and O;

q is from 0 to about 50;

M is an optionally protected internucleoside linkage;

(b) reacting said compound of Formula I with a compound of Formula II:

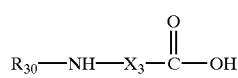

wherein:

$R_{30}$ is an amino protecting group;

$X_3$ is —$CH(Z_1)$— or a group of Formula XI:

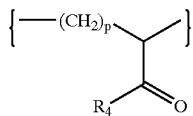

$Z_1$ is the sidechain of a naturally occurring amino acid, or a protected sidechain of a naturally occurring amino acid, wherein the amino acid is preferably glutamic acid;

p is 1 or 2, with 2 being preferred;

to form a compound of Formula IVA, IVB, IVC, or IVD:

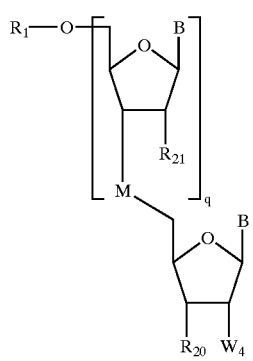

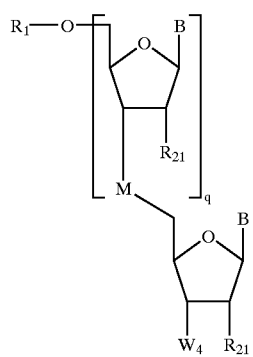

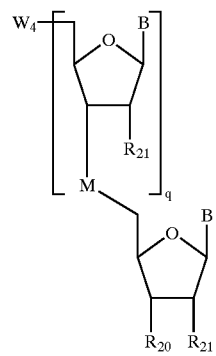

-continued

IVD

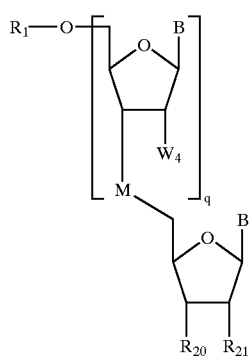

wherein:

$W_4$ has the formula:

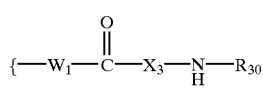

and treating said compound of Formula IVA, IVB, IVC or IVD with a deprotecting reagent to form a compound of Formula VA, VB, VC or VD:

VA

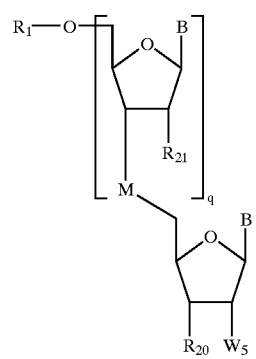

VB

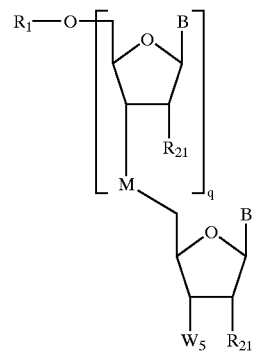

-continued

VC

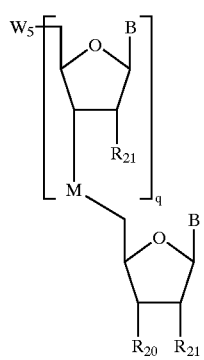

VD

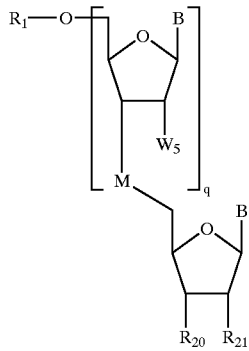

where $W_5$ has the Formula:

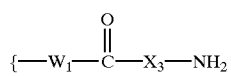

In some preferred embodiments, the methods of the invention further comprise condensing said compound of Formula V with a compound of Formula VI:

VI

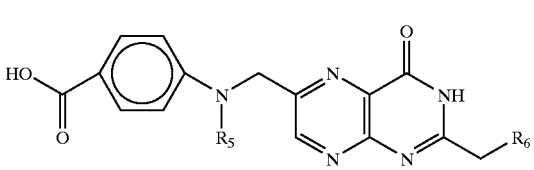

wherein:

$R_5$ is H or an amino protecting group;

$R_6$ is H or an amino protecting group;

to form a compound of Formula VIIA, VIIB, VIIC, OR VIID:

VIIA

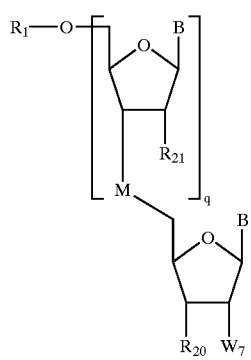

VIIB

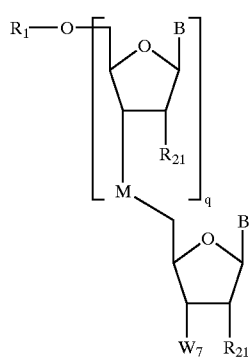

VIIC

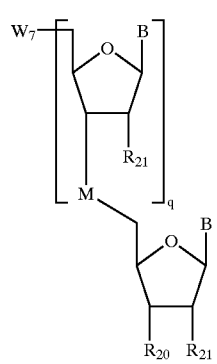

VIID

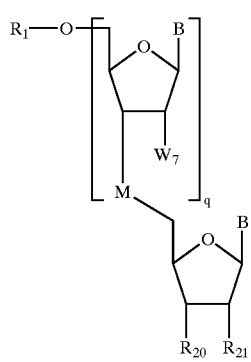

wherein $W_7$ has the Formula:

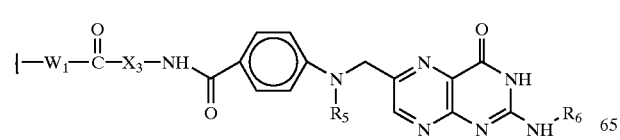

Some preferred embodiments of the methods of the invention further comprise contacting said compound of Formula VIIA or VIID with a phosphitylating reagent to form a compound of Formula VIIIA or VIIIA–D:

VIIIA

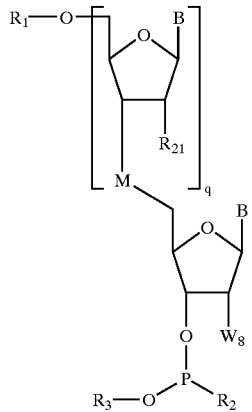

VIIID

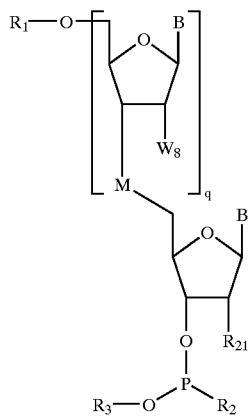

wherein $W_8$ has the Formula:

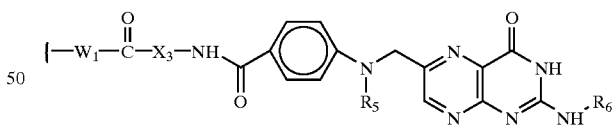

In some preferred embodiments, said compound of Formula VI is prepared by the steps of reacting a compound of Formula IX:

IX

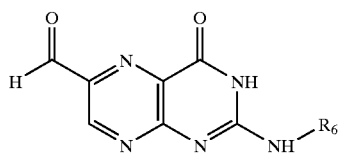

with a compound of Formula X:

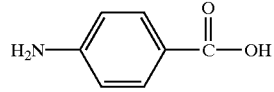
X and treating the product of said reaction with a protecting group reagent to form said compound of Formula VI.

In some especially preferred embodiments, said compound IX is prepared by reacting folic acid:

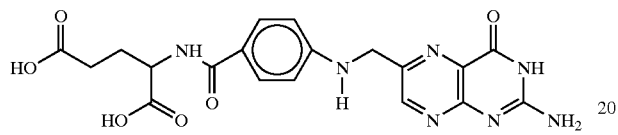

with a reagent effective to form pterin aldehyde:

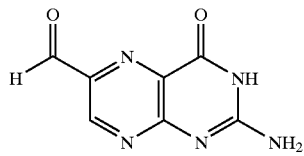

and protecting the amino group of said pterin aldehyde.

Also provided in accordance with the present invention are methods for the preparation of a folic acid derivative comprising the steps of reacting folic acid:

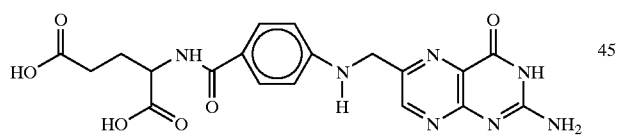

with a reagent effective to form pterin aldehyde:

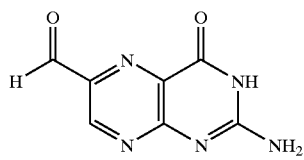

Preferably, the methods further comprise protecting the amino group of said pterin aldehyde.

The present invention also provides compounds having the Formula XIIIA, XIIIB, XIIIC or XIIID:

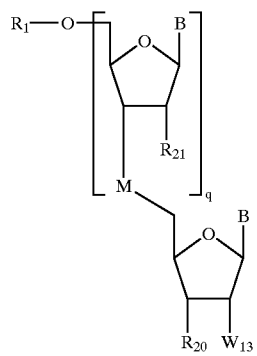
XIIIA

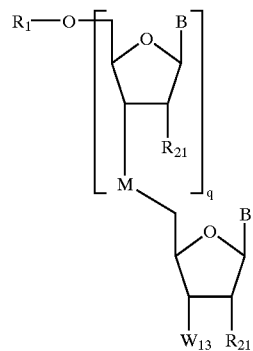
XIIIB

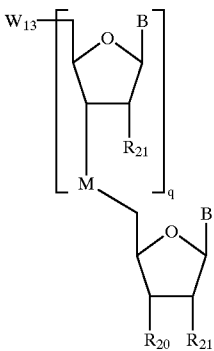
XIIIC

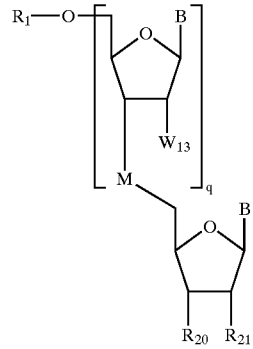
XIIID

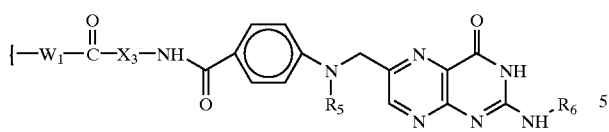

R₁ is H or a hydroxyl protecting group;
B is a nucleobase;
each R₂₁ is H, OH, F, or a group of formula Z—R₂₂—(R₂₃)ᵥ;
  Z is O, S, NH or N—R₂₂—(R₂₃)ᵥ;
  R₂₂ is $C_1$–$C_{20}$ alkyl, $C_2$–$C_{20}$ alkenyl, or $C_2$–$C_{20}$ alkynyl;
  R₂₃ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
or R₂₁ has one of the formulas:

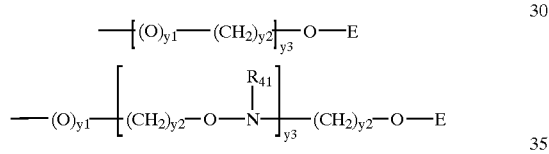

wherein:
y1 is 0 or 1;
y2 is 0 to 10;
y3 is 1 to 10;
E is N (R₄₁)(R₄₂) or N=C(R₄₁)(R₄₂);
  each R₄₁ and each R₄₂ is independently H, $C_1$–$C_{10}$ alkyl, a nitrogen protecting group, or R₄₁ and R₄₂ taken together form a nitrogen protecting group; or R₄₁ and R₄₂ taken together with the N or C atom to which they are attached form a ring structure that can include at least one heterotom selected from N and O;
v is from 0 to about 10;
q is from 0 to about 50;
M is an optionally protected internucleoside linkage;
W₁ is a linking group, O, NH or S, with a linking group being preferred;
R₂₀ is OH or a group of formula:

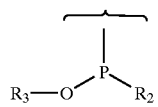

R₂ is —N(R₇)₂, or a heterocycloalkyl or heterocycloalkenyl ring containing from 4 to 7 atoms, and having up to 3 heteroatoms selected from nitrogen, sulfur, and oxygen;
R₇ is straight or branched chain alkyl having from 1 to 10 carbons;

R₃ is a phosphorus protecting group;
n is from 1 to about 10;
R₅ is H or an amino protecting group;
R₆ is H or an amino protecting group;
X₃ is —CH(Z₁)— or a group of Formula XI:

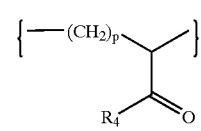

Z₁ is the sidechain of a naturally occurring amino acid, or a protected sidechain of a naturally occurring amino acid, wherein the amino acid is preferably glutamic acid;
p is 1 or 2, with 2 being preferred; and
R₄ is a hydroxyl group, or a protected hydroxyl group.

The present invention also provides compositions comprising a compound of Formula XIIIA–D wherein X₃ has the Formula XI and p is 2, said composition being substantially free of a compound of Formula XIVA, XIVB, XIVC, or XIVD:

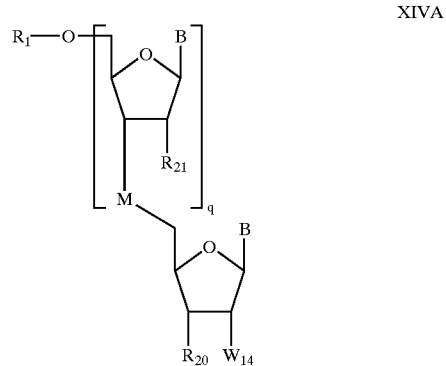

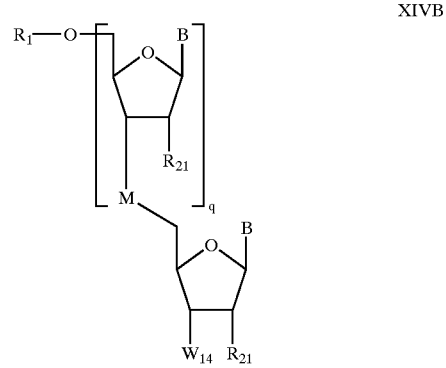

-continued
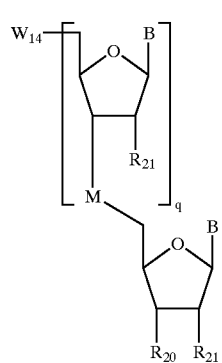
XIVC
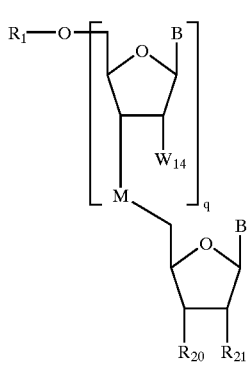
XIVD
wherein:
$W_{14}$ has the Formula:
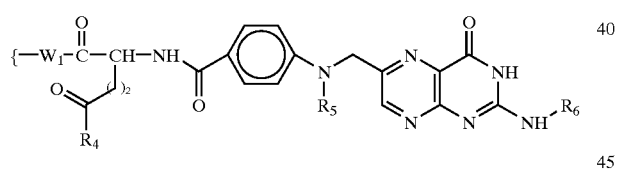
Also provided in accordance with the present invention are compositions comprising a compound of Formula XII-IA–D wherein $X_3$ has the Formula XII and m is 2, said composition being substantially free of a compound of Formula XVA, XVB, XVC or XVD:
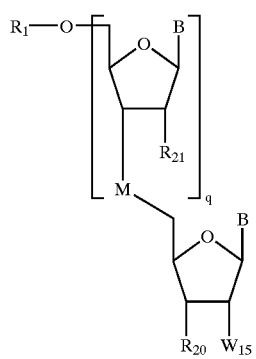
XVA
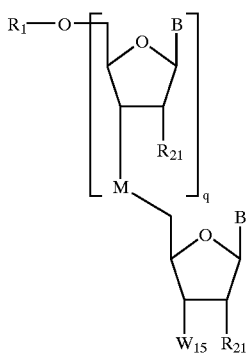
XVB
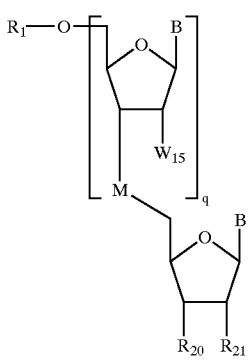
XVC
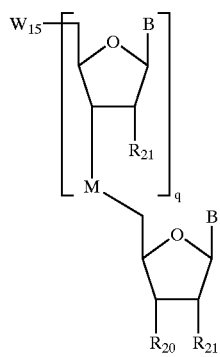
XVD
wherein $W_{15}$ has the Formula:

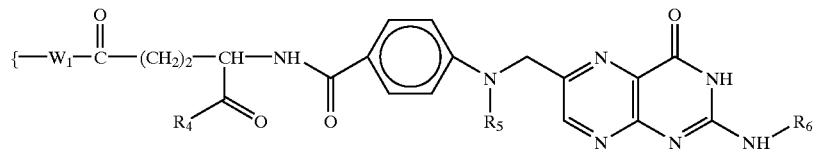
The present invention further provides compounds having the Formula XVIA, XVIB, XVIC or XVID:
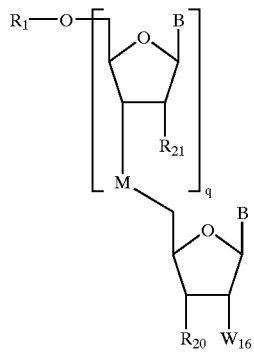
XVIA
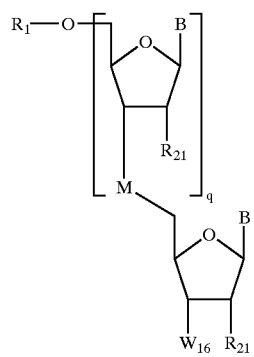
XVIB
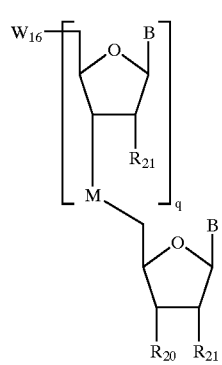
XVIC
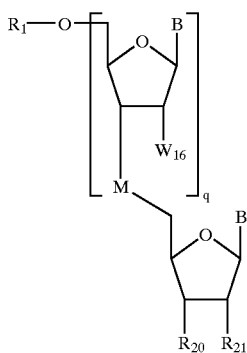
XVID
wherein:
$W_{16}$ has the Formula:
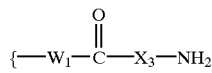
wherein the constituent variables are as defined above.
Also provided in accordance with the present invention are compounds having the Formula XVIIA, XVIIB, XVIIC or XVIID:
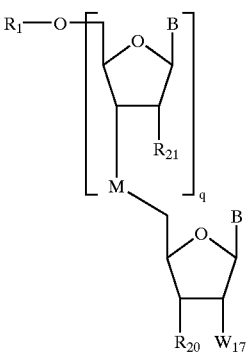
XVIIA
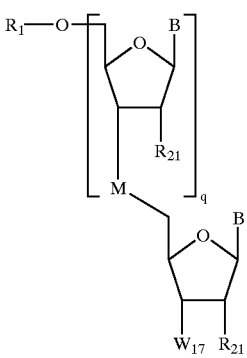
XVIIB -continued

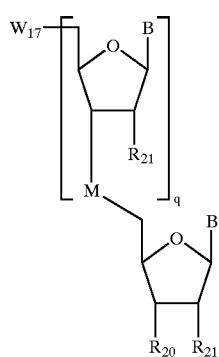

XVIIC

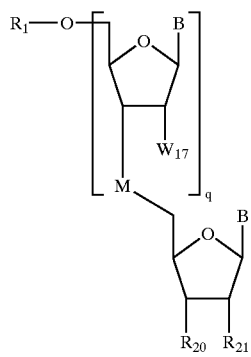

XVIID wherein:

$W_{17}$ has the Formula:

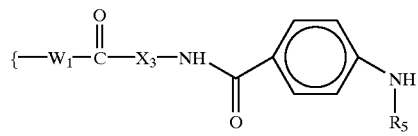

where the constituent variables are as defined above.

In some preferred embodiments of the foregoing methods and compounds, $X_3$ is a group of Formula XI:

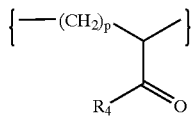

XI wherein:

p is 1 or 2, with 2 being preferred;

$R_4$ is a hydroxyl group, or a protected hydroxy group;

or $X_3$ is a group of Formula XII:

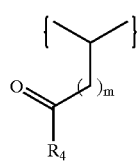

XII wherein m is 1 or 2, with 2 being preferred.

In some preferred embodiments of the foregoing compounds and methods, q is 0.

In further preferred embodiments of the foregoing compounds and methods, $X_3$ is a group of Formula XI, preferably wherein p is 2.

In further preferred embodiments of the foregoing compounds and methods, $X_3$ is a group of Formula XII, preferably wherein m is 2.

In preferred embodiments of the foregoing compounds and methods, $W_1$ has the Formula —O—$(CH_2)_n$—NH—, where n is from 1 to about 10, with 6 being preferred.

In some preferred embodiments of the foregoing compounds and methods, $R_2$ is dimethoxytrityl. In further preferred embodiments, $R_4$ is t-butoxy. In still further preferred embodiments, $R_5$ is trifluoroacetoyl. In further preferred embodiments, $R_6$ is —C(=O)—CH$(CH_3)_2$. In yet further preferred embodiments, $R_{30}$ is fluorene-9-yl methoxycarbonyl.

In some preferred embodiments of the foregoing compounds and methods, $R_1$ is dimethoxytrityl, $W_1$ has the Formula —O—$(CH_2)_n$—NH— where n is 6, $X_3$ has the Formula XI where p is 2, $R_4$ is t-butoxy, $R_5$ is trifluoroacetoyl, $R_6$ is —C(=O)—CH$(CH_3)_2$, and $R_{30}$ is FMOX.

In further preferred embodiments, $R_1$ is dimethoxytrityl, $W_1$ has the Formula —O—$(CH_2)_n$—NH— where n is 6, $X_3$ has the Formula XII where m is 2, $R_4$ is t-butoxy, $R_5$ is trifluoroacetoyl, $R_6$ is —C(=O)—CH$(CH_3)_2$, and $R_{30}$ is FMOX.

DETAILED DESCRIPTION OF THE INVENTION

Figure 1:
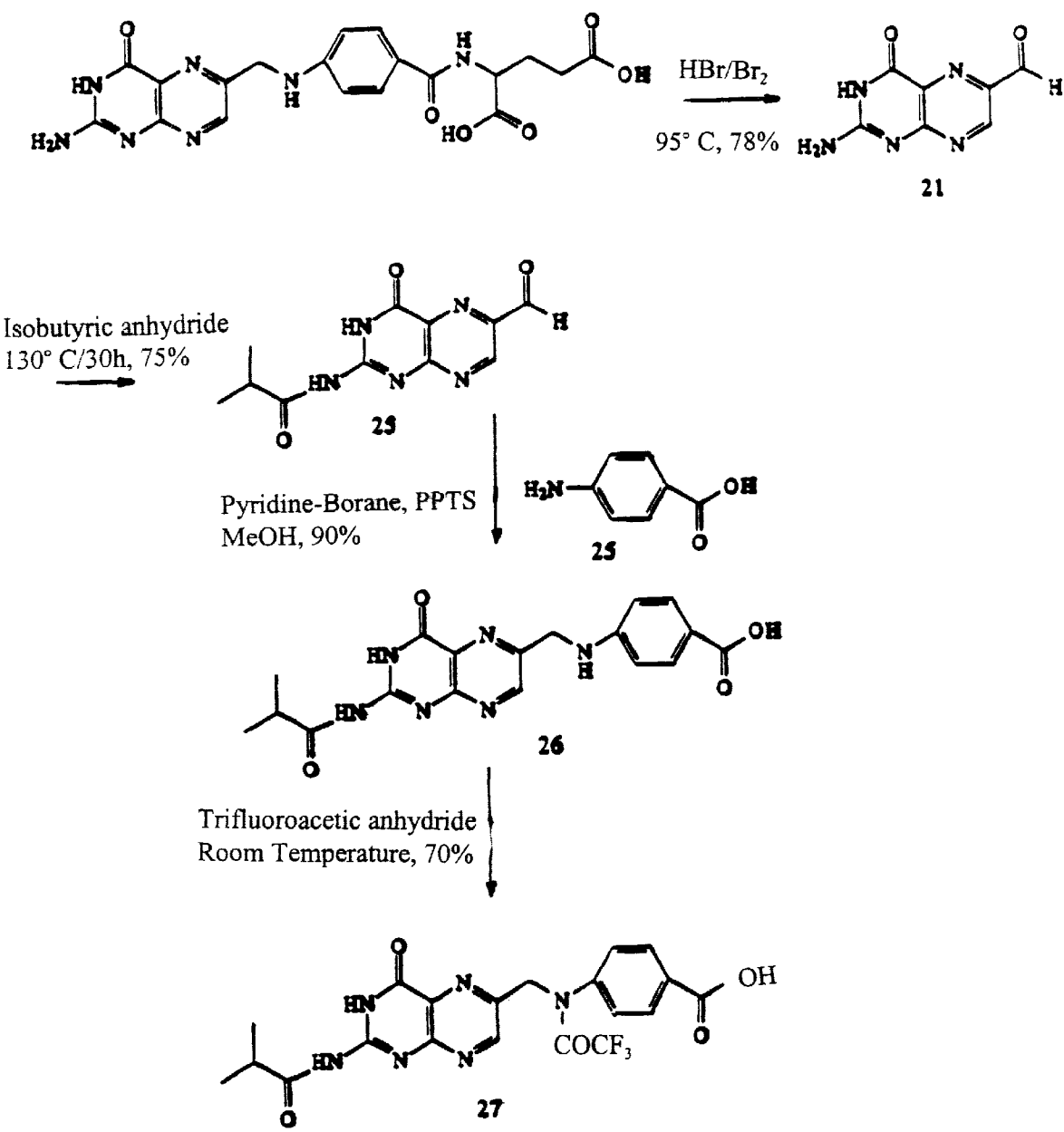
FIG. 1 shows the synthesis of $N^2,N^{10}$-protected pteroic acid.
Figure 2:
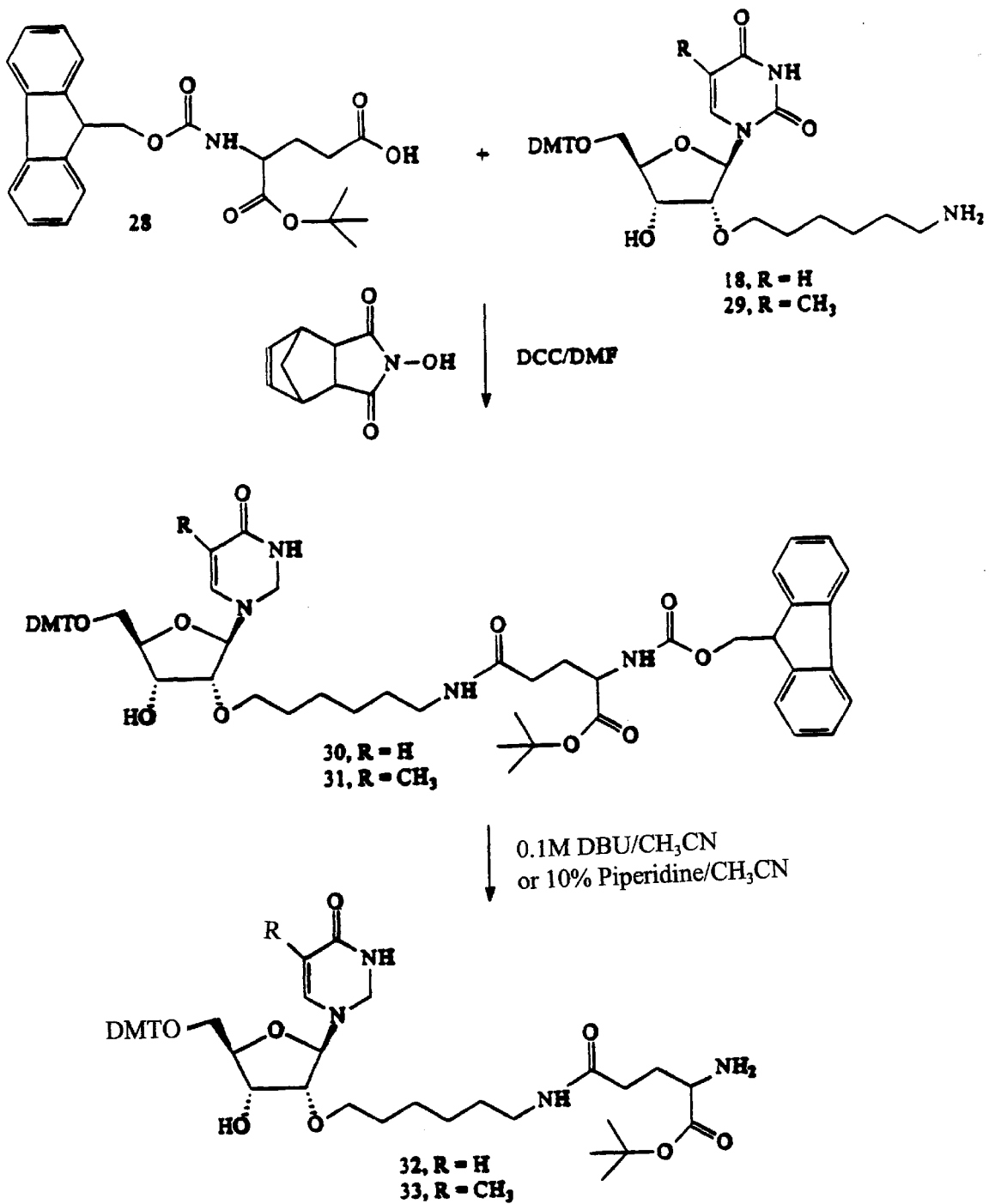
FIG. 2 shows the synthesis of 2'-O-(γ-(α-t-butyl-glutamoyl(hexylamino)))-5'-O-DMT-5-methyl-uridine.
Figure 3:
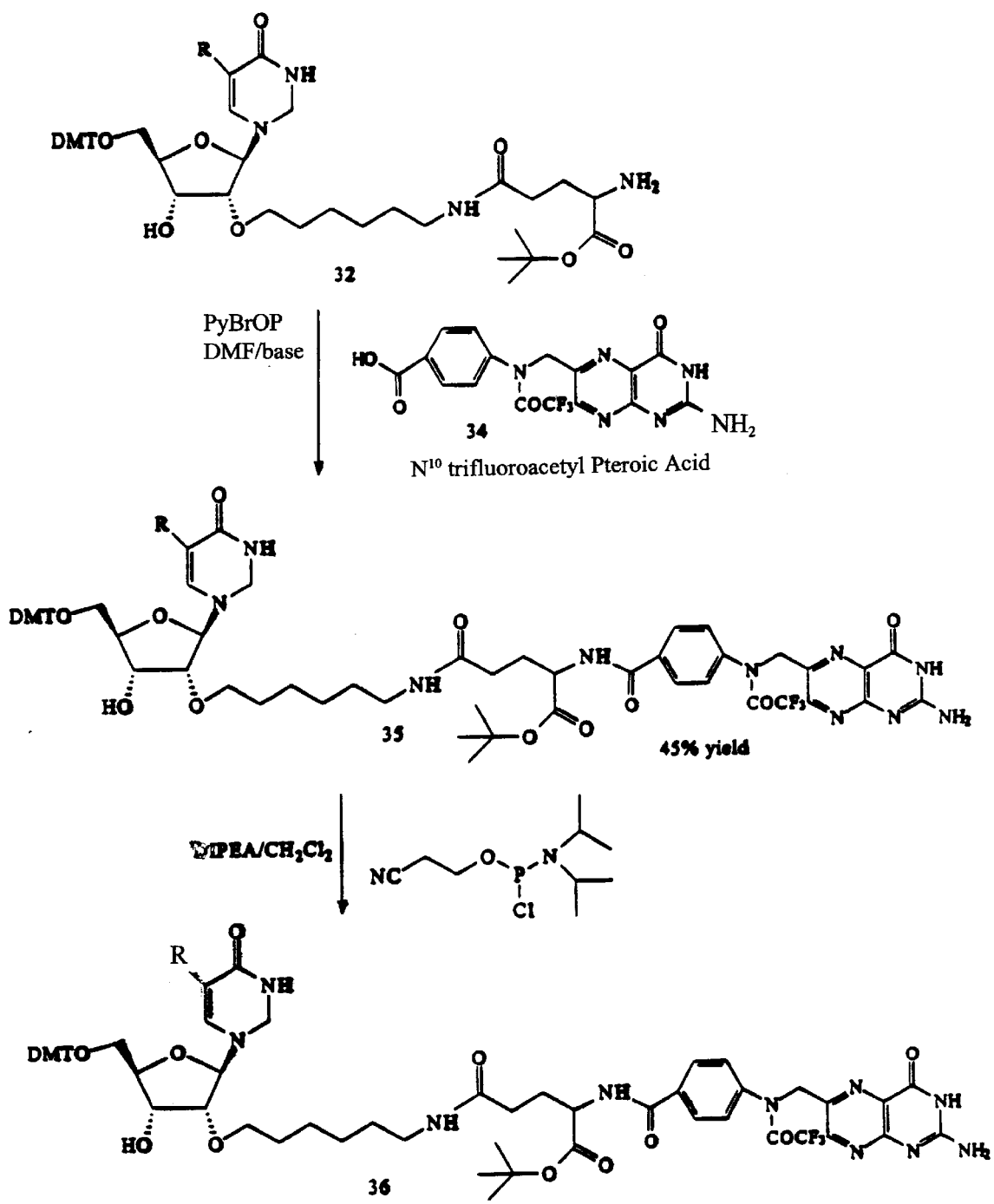
FIG. 3 shows the synthesis of the phosphoramidite of the γ-conjugate of folic acid attached to 2'-O-(hexylamino)-5'-O-DMT-5-methyl-uridine.
Figure 4:
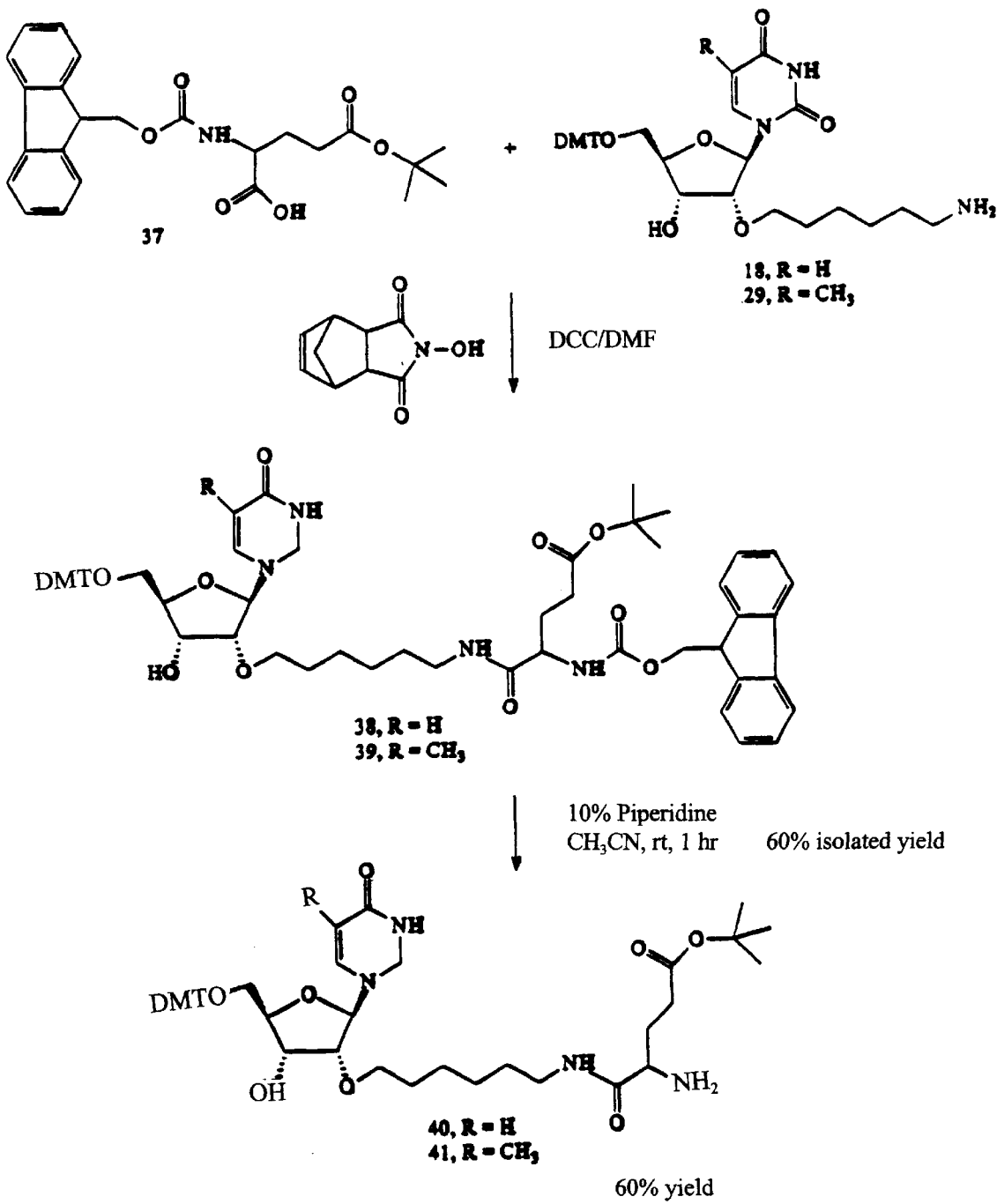
FIG. 4 shows the synthesis of 2'-O-(α-(γ-t-butyl-glutamoyl(hexylamino)))-5'-O-DMT-5-methyl-uridine.
Figure 5:
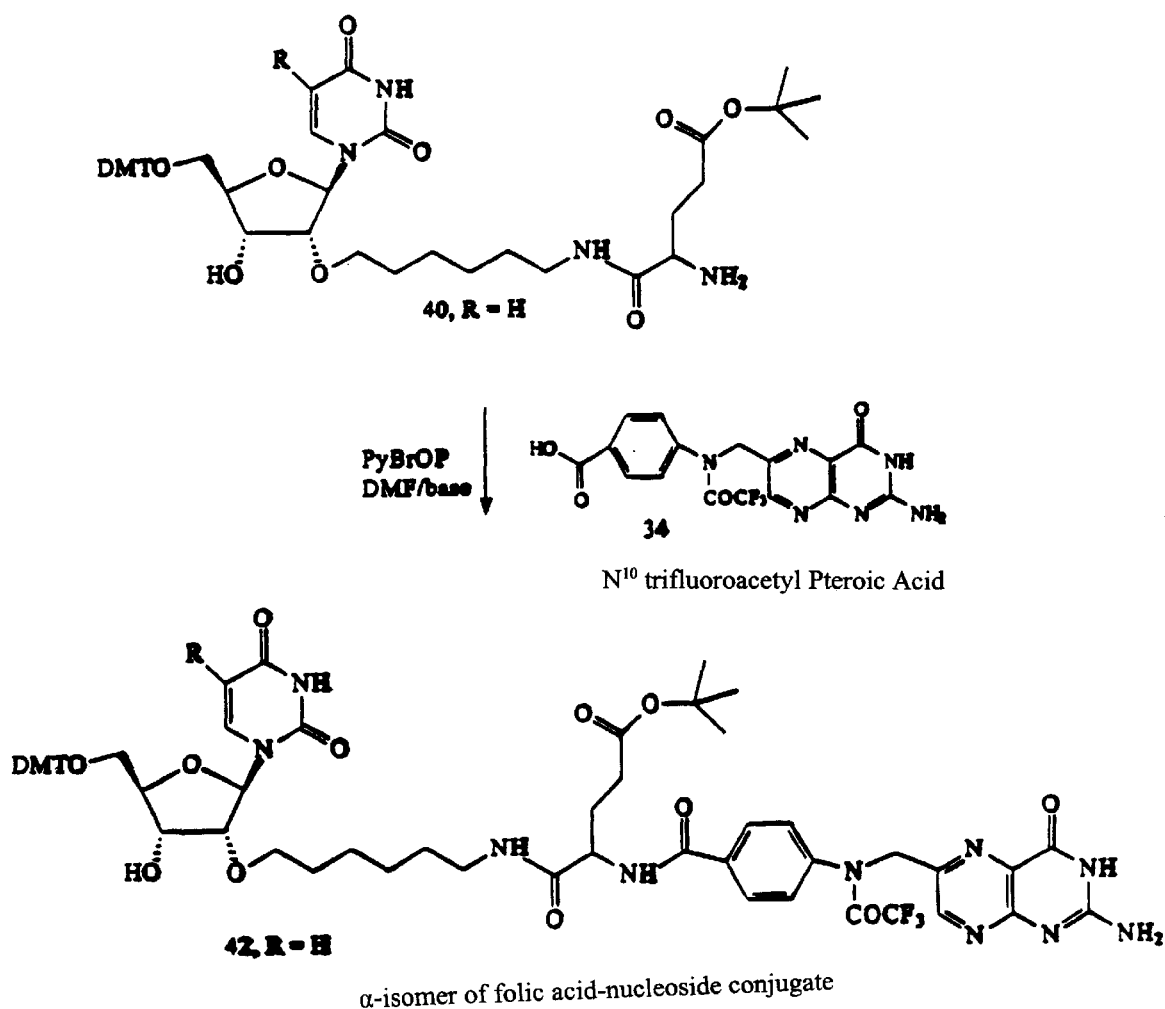
FIG. 5 shows the synthesis of the α-conjugate of folic acid attached to 2'-O-(hexylamino)-5'-O-DMT-uridine. shows the synthesis of 2'-O-(γ-(α-t-butyl-glutamoyl (hexylamino)))-5'-O-DMT-5-methyl-uridine.
Figure 6:
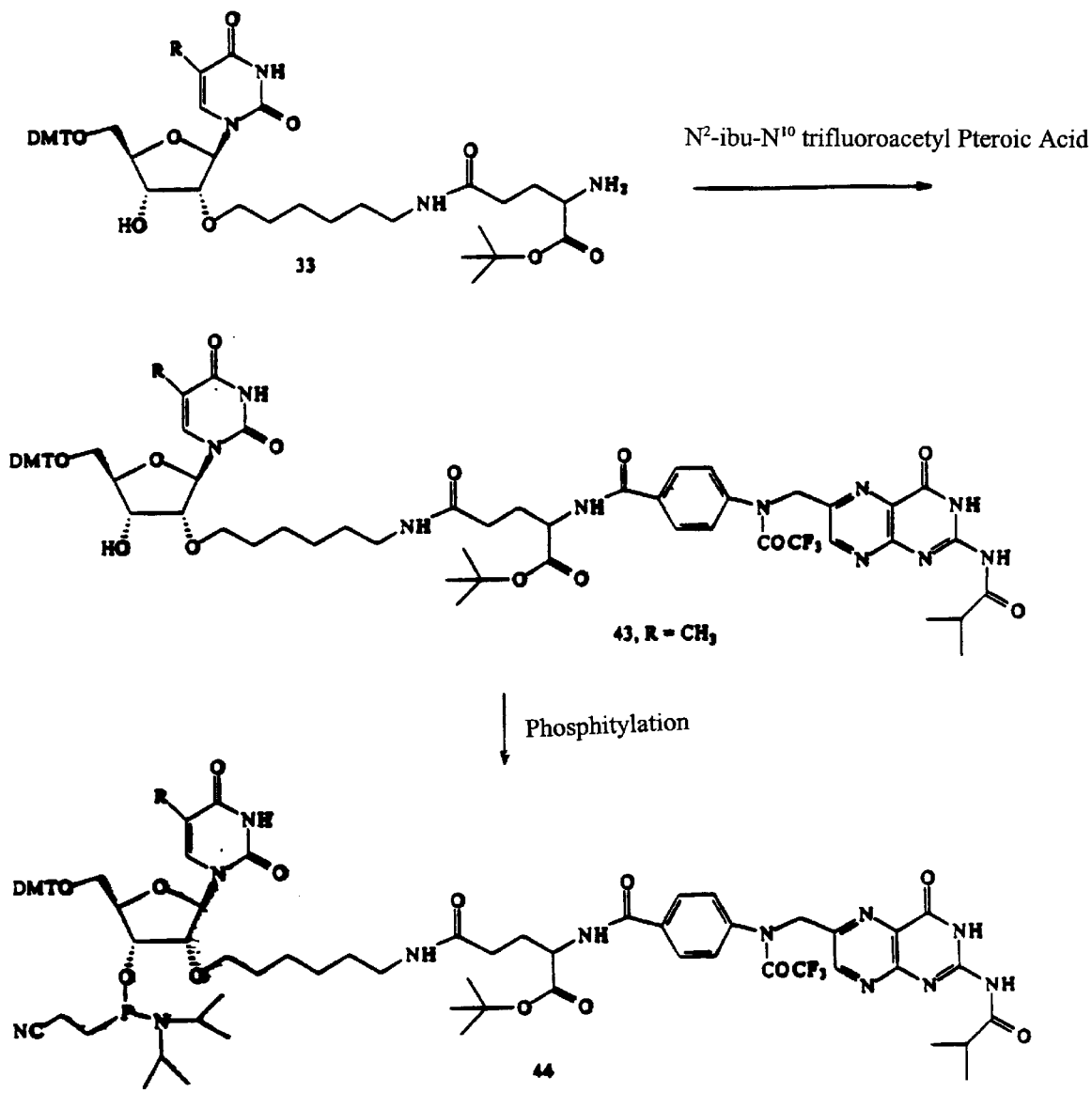
FIG. 6 shows the synthesis of the phosphoramidite of the fully protected γ-conjugate of folic acid attached to 2'-O-(hexylamino)-5'-O-DMT-uridine.
Figure 7:
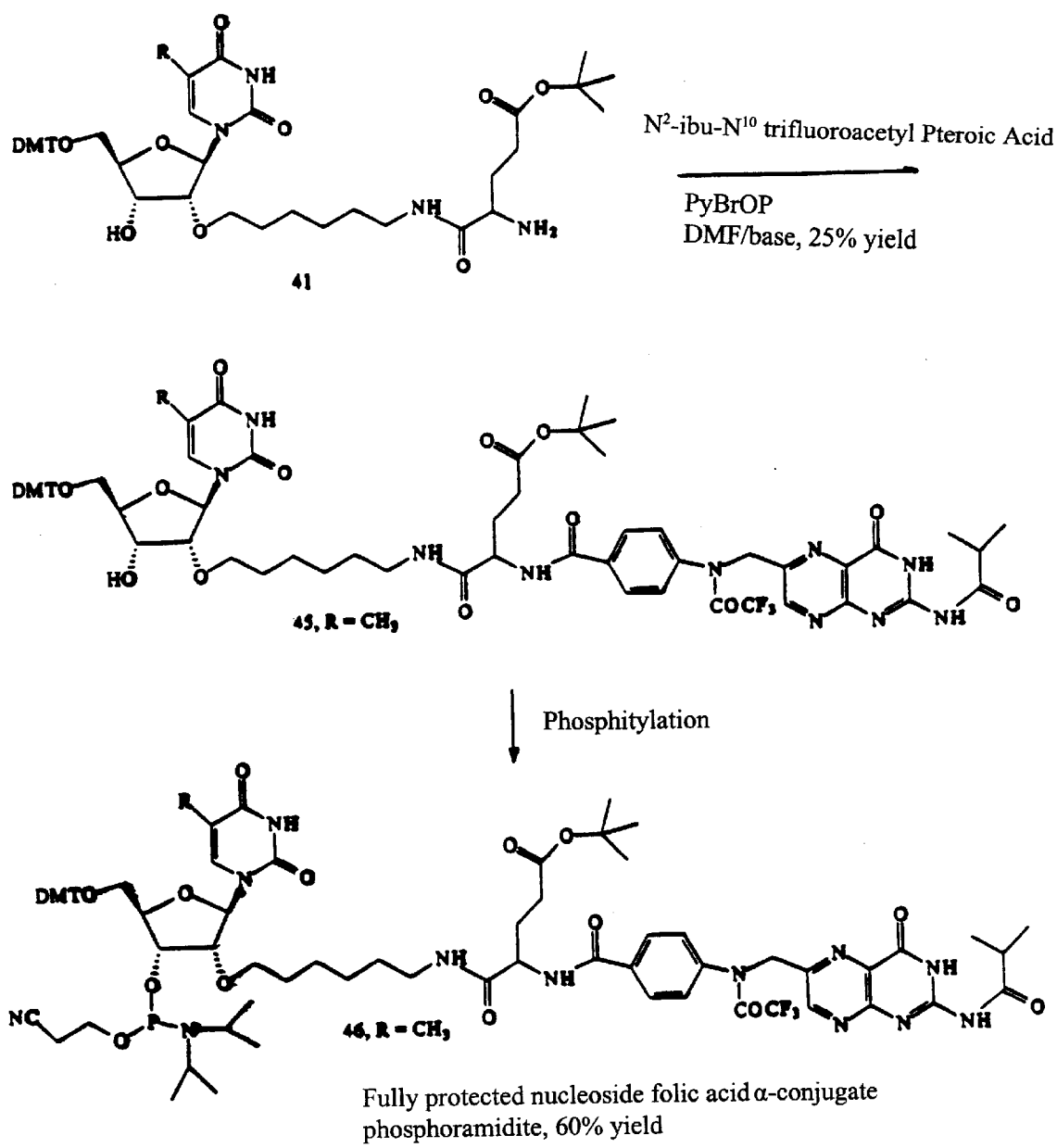
FIG. 7 shows the synthesis of the phosphoramidite of the fully protected α-conjugate of folic acid attached to 2'-O-(hexylamino)-5'-O-DMT-uridine.
Figure 8A:
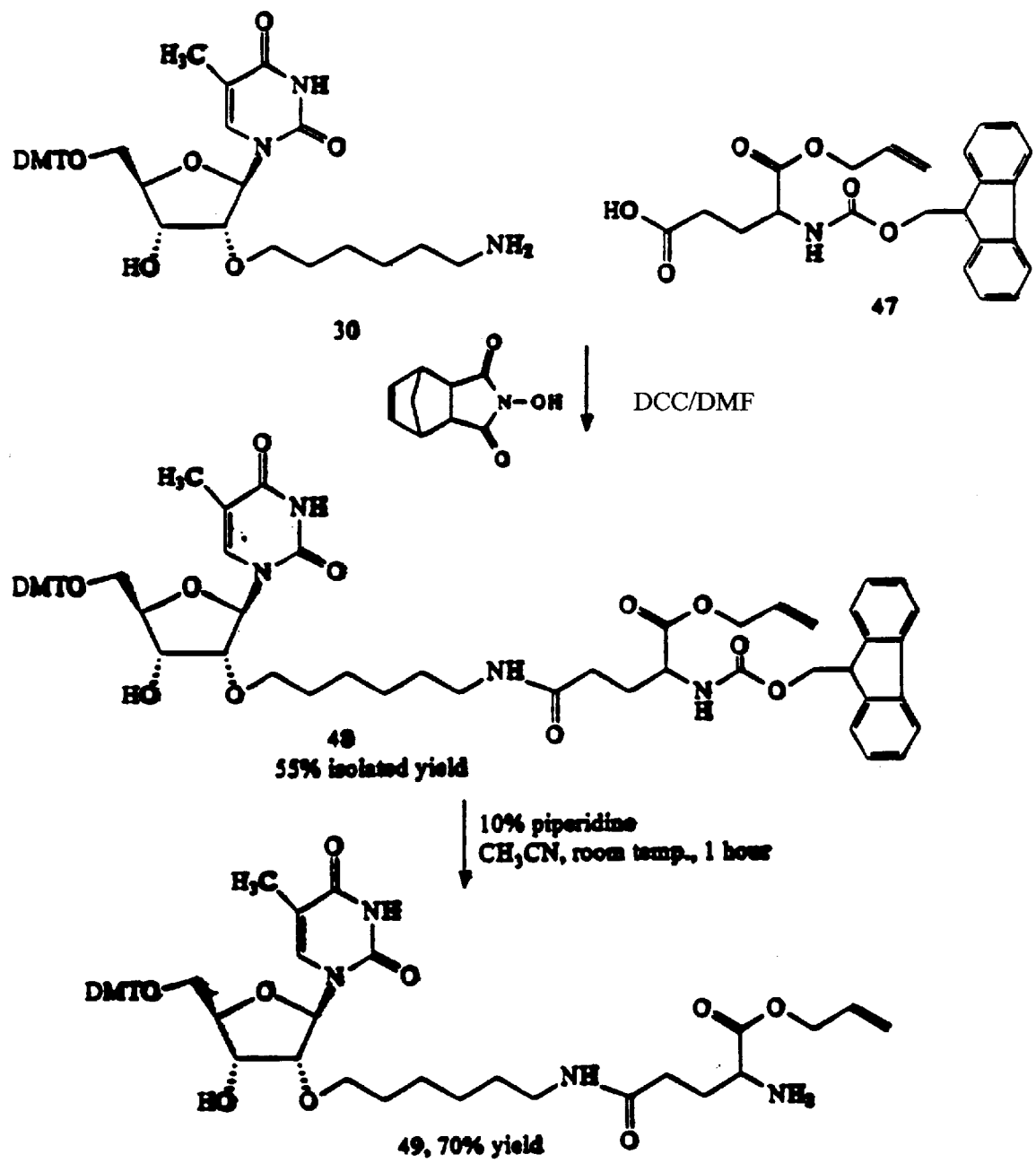
FIGS. 8a and 8b show the synthesis of the γ-conjugate of α-O-allyl protected folic acid attached to 2'-O-(hexylamino)-5'-O-DMT-5-methyl-uridine, and the synthesis of the phosphoramidite of the γ-conjugate of α-O-allyl protected folic acid attached to 2'-O-(hexylamino)-5'-O-DMT-5-methyl-uridine.
Figure 8B:
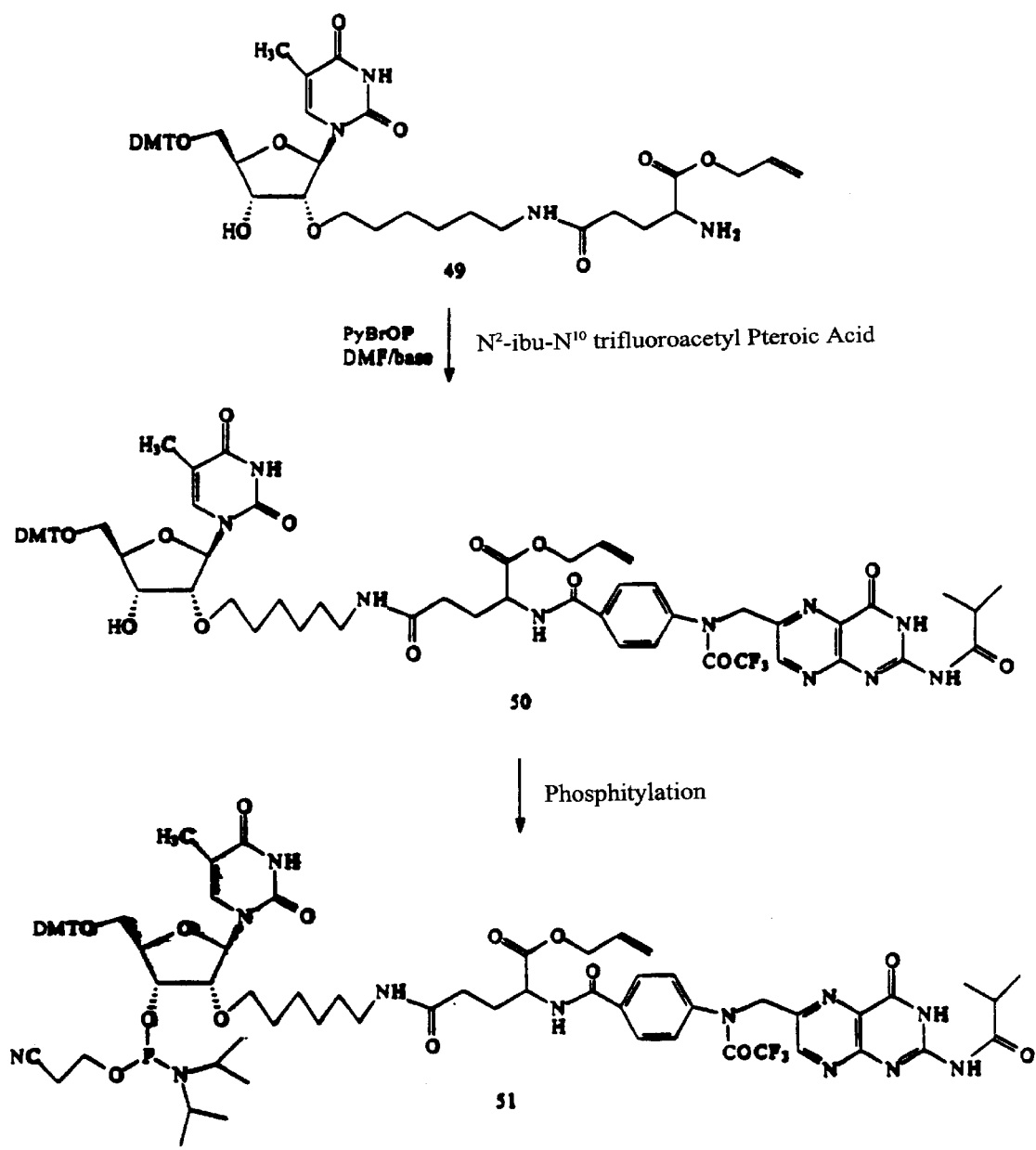

The present invention provides folate and folate analog-containing conjugates that have improved therapeutic properties, including improved transfer across cellular membranes. The present invention also provides methods for the preparation of the oligonucleotide-folate conjugates.

In preferred embodiments, the present invention provides methods for the preparation of mononucleosides or oligonucleotides having one or more folate molecules conjugated thereto, optionally via one or more linking groups.

In preferred embodiments, the methods comprise the steps of:

(a) providing a compound of Formula IA, IB, IC or ID:

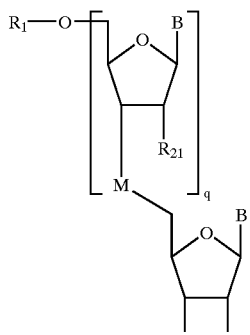

IA

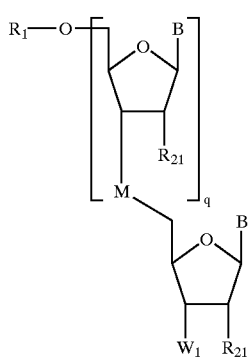

IB

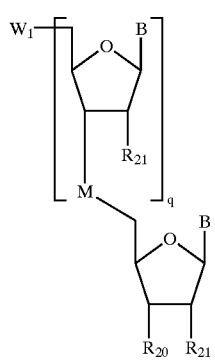

IC

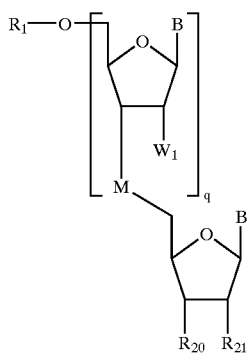

ID wherein:
W$_1$ is a linking group;
R$_1$ is H or a hydroxyl protecting group;
B is a nucleobase;
each R$_{21}$ is H, OH, F, or a group of formula Z—R$_{22}$—(R$_{23}$)$_v$;

Z is O, S, NH, or N—R$_{22}$—(R$_{23}$)$_v$;
R$_{22}$ is C$_1$–C$_{20}$ alkyl, C$_2$–C$_{20}$ alkenyl, or C$_2$–C$_{20}$ alkynyl;
R$_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
v is from 0 to about 10;
or R$_{21}$ has one of the formulas:

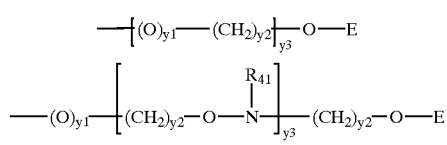

wherein:
y1 is 0 or 1;
y2 is 0 to 10;
y3 is 1 to 10;
E is N(R$_{41}$)(R$_{42}$) or N═C(R$_{41}$)(R$_{42}$);
each R$_{41}$ and each R$_{42}$ is independently H, C$_1$–C$_{10}$ alkyl, a nitogen protecting group, or R$_{41}$ and R$_{42}$ taken together form a nitrogen protecting group; or R$_{41}$ and R$_{42}$ taken together with the N or C atom to which they are attached form a ring structure that can include at least one heterotom selected from N and O;
q is from 0 to about 50;
M is an optionally protected internucleoside linkage;

(b) reacting said compound of Formula I with a compound of Formula II:

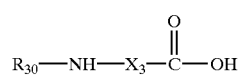

II wherein:

R$_{30}$ is an amino protecting group;
X$_3$ is —CH(Z$_1$)— or a group of Formula XI:

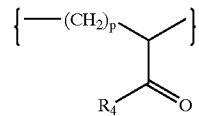

XI $Z_1$ is the sidechain of a naturally occurring amino acid, or a protected sidechain of a naturally occurring amino acid, wherein the amino acid is preferably glutamic acid;

p is 1 or 2, with 2 being preferred;

to form a compound of Formula IVA, IVB, IVC, or IVD:

IVA
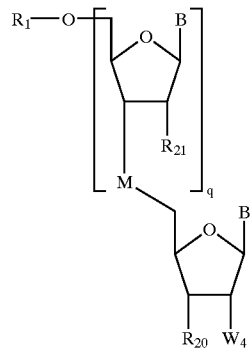

IVB
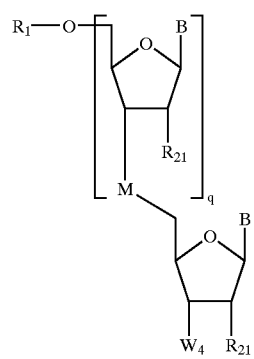

IVC
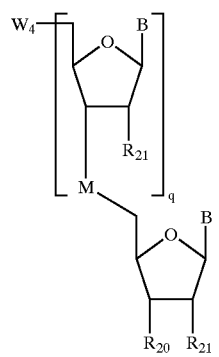

IVD
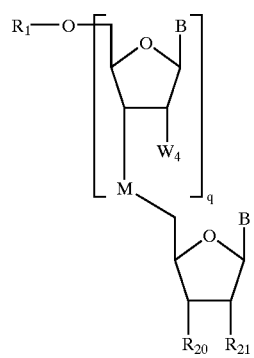

wherein:

$W_4$ has the formula:

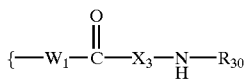

and treating said compound of Formula IVA, IVB, IVC or IVD with a deprotecting reagent to form a compound of Formula VA, VB, VC or VD:

VA
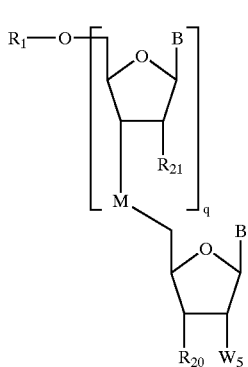

VB
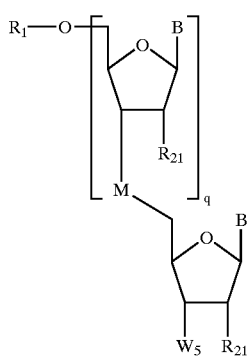

VC
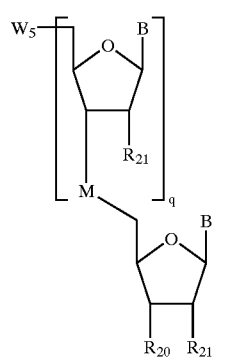

VD

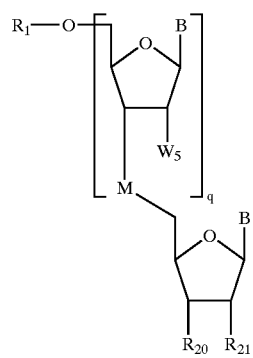

where W₅ has the Formula:

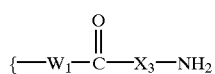

As used herein, the term "reacting" means placing moieties together in a container under conditions of time, temperature and pressure such that the indicated reaction occurs. As used herein, the term "treating said compound of Formula IVA, IVB, IVC or IVD with a deprotecting reagent to form a compound of Formula VA, VB, VC or VD" means causing the formation of a compound of Formula VA, VB, VC or VD by effecting the deprotection of a compound of Formula IVA, IVB, IVC or IVD using a deprotection reagent. The term "deprotecting reagent" denotes a reagent that is effective to remove the protecting group $R_{30}$. Suitable deprotecting reagents can be found in Greene and Wuts, *Protective Groups in Organic Synthesis*, Chapter 2, 2d ed, John Wiley & Sons, New York, 1991, and *Oligonucleotides And Analogues A Practical Approach*, Ekstein, F. Ed., IRL Press, N.Y, 1991, each of which are incorporated by reference herein in their entirety. Preferred deprotection reagents include, but are not limited to, 0.1 M DBU in acetonitrile or a 10% solution of piperidine in acetonitrile.

In some preferred embodiments, the methods of the invention further comprise condensing said compound of Formula V with a compound of Formula VI:

VI

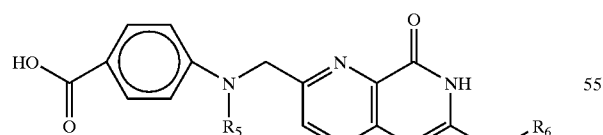

wherein:

$R_5$ is H or an amino protecting group;

$R_6$ is H or an amino protecting group;

to form a compound of Formula VIIA, VIIB, VIIC, or VIID:

VIIA

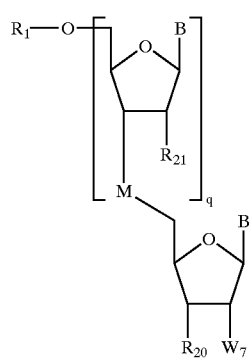

VIIB

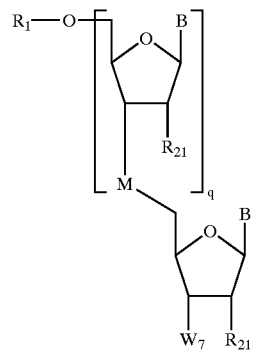

VIIC

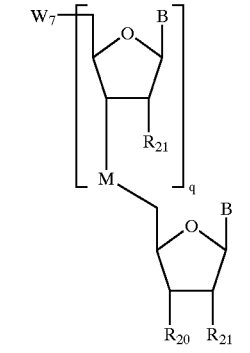

VIID

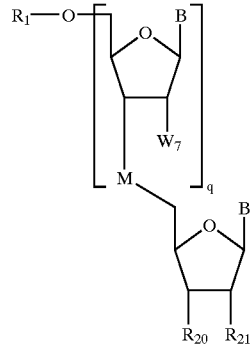

wherein $W_7$ has the Formula:

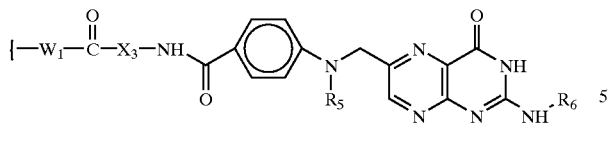

As used herein the term "condensing said compound of Formula V with a compound of Formula VI" means placing a compound of Formula V together with a compound of Formula VIA–D under conditions of time, temperature and pressure effective to form a condensation product of Formula VIIA–D. The condensation is preferably performed in the presence of dicyclohexylcarbodiimide (DCC) and HONB as activating reagent in anhydrous DMF. Other suitable reagents for this purpose include HATU, HBTU and PyBrop.

Some preferred embodiments of the methods of the invention further comprise contacting said compound of Formula VIIA or VIID with a phosphitylating reagent to form a compound of Formula VIIIA or VIIIA–D:

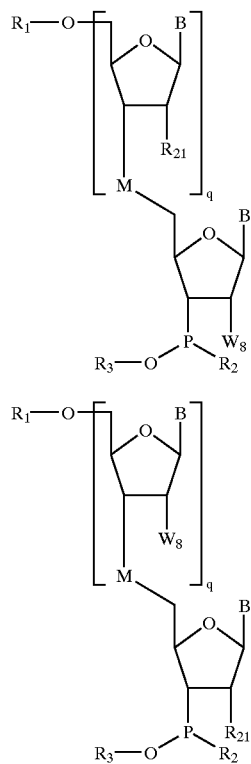

wherein $W_7$ has the Formula:

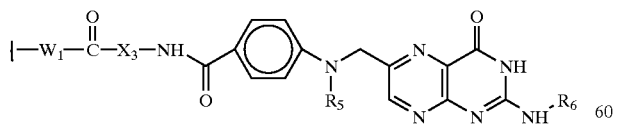

The phosphitylated compound of Formula VIIIA or VIIID can be used as a synthon in standard oligonucleotide synthetic regimes, as disclosed in, for example, Ekstein, infra.

In some preferred embodiments, compounds of Formula VI are prepared by reacting a compound of Formula IX:

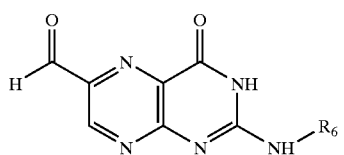

with a compound of Formula X:

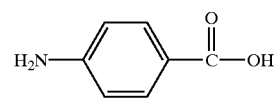

and treating the product of said reaction with a protecting group reagent to form said compound of Formula VI.

In accordance with preferred embodiments of the methods of the invention, folic acid conjugates and/or derivatives can be prepared from pterin aldehyde, which is obtained from folic acid. Preferably, the folic acid from which the pterin aldehyde is obtained is isolated from a natural source, or purchased commercially. Thus, in some especially preferred embodiments, compounds of Formula IX are prepared by reacting folic acid:

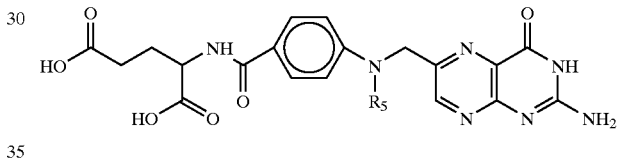

with a reagent effective to form pterin aldehyde:

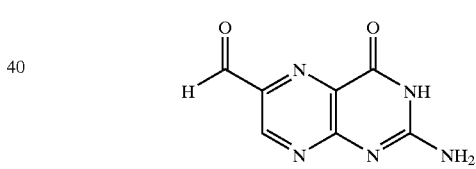

and
protecting the amino group of said pterin aldehyde.

In preferred embodiments, the pterin aldehyde is obtained from the reaction of folic acid and Hbr/$Br_2$, preferably at a temperature of 95–100° C. The amino group of the pterin aldehyde can be selectively protected by, for example, treatment with isobutyric anhydride at a temperature of 130° C. for 30 hours. The 4-oxo moiety of the pterins may also be protected as the diphenylcarbamate species by using, for example, diphenylcarbamoyl chloride.

Also provided in accordance with the present invention are methods for the preparation of a folic acid derivative comprising the steps of reacting folic acid:

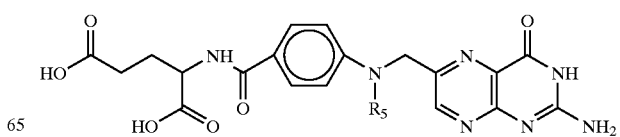

with a reagent effective to form pterin aldehyde:

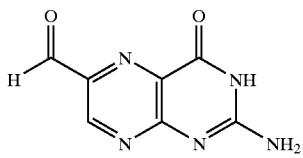

and preferably protecting the amino group of said pterin aldehyde.

In preferred embodiments, the conjugates of the present invention include folate moieties such as, but not limited to, folic acid, folic acid derivatives and analogs, antifolates and deazafolates. As used herein, the term "folate" shall include all such structures. Examples of such folates include folic acid, dihydrofolic acid, tetrahydrofolic acid, folinic acid, pteropolyglutamic acid, dihydrofolates, tetrahydrofolates, tetrahydropterins, 1-deaza, 3-deaza, 5-deaza, 8-deaza, 10-deaza, 1,5-dideaza, 5,10-dideaza, 8,10-dideaza and 5,8-dideaza folate analogs, and antifolates. In some preferred embodiments, folic acid is employed as the folate moiety in the compounds and methods of the invention.

The folate moiety or moieties may be attached to one or more sites on a mononucleoside, mononucleotide phosphoramidite, or oligonucleotide of the invention. These sites include one or more of, but are not limited to, the 2'-position, 3'-position, 5'-position, the internucleotide linkage, and a nucleobase atom of any nucleotide residue.

The attachment of folates to such structures can be performed, according to some preferred embodiments of the invention, using a linking group, or without the use of such a linking group.

In some preferred embodiments of the compounds and methods of the present invention, one or more folate moieties is attached to a nucleoside or oligonucleotide portion of the conjugate via linking groups. Preferred linking groups of the invention include, but are not limited to, ω-aminoalkoxy linkers, ω-aminoalkylamino linkers, cysteamine, heterobifunctional linkers, homobifunctional linkers, and a universal linker (derived from 3-dimethoxytrityloxy-2-aminopropanol). A particularly preferred linking group for the synthesis of oligonucleotide-folate conjugates of the invention is a 6-aminohexyloxy group.

The oligonucleotide conjugates of the invention contain one or more optionally protected oligonucleoside linkages, represented by variable "M" in the formulas provided herein. Representative internucleoside linkages include optionally protected phosphite, phosphodiester, phosphorothioate, phosphorodithioate, and alkyl phosphonate linkages. As used herein, the term "protected" means that the indicated moiety has appended a protecting group thereto.

Some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule. Representative hydroxyl protecting groups, for example, are disclosed by Beaucage, et al., *Tetrahedron* 1992, 48, 2223–2311. Further hydroxyl protecting groups, as well as other representative protecting groups are disclosed in Greene and Wuts, *Protective Groups in Organic Synthesis*, Chapter 2, 2d ed, John Wiley & Sons, New York, 1991, and *Oligonucleotides And Analogues A Practical Approach*, Ekstein, F. Ed., IRL Press, N.Y, 1991, each of which is hereby incorporated by reference in its entirety.

In some especially preferred embodiments, the nucleoside components of the oligonucleotide-folate conjugates are connected to each other by optionally protected phosphorothioate internucleoside linkages. Representative protecting groups for phosphorus containing internucleoside linkages such as phosphphite, phosphodiester and phosphorothioate linages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., *Tetrahedron*, 49 No. 10, pp. 1925–1963 (1993); Beaucage, S. L. and Iyer, R. P., *Tetrahedron*, 49 No. 46, pp. 10441–10488 (1993); Beaucage, S. L. and Iyer, R. P., *Tetrahedron*, 48 No. 12, pp. 2223–2311 (1992).

The present invention provides compounds that have a plurality of linked nucleosides and where at least one of the nucleosides is a 2'-functionalized nucleoside having a folate molecule linked to the 2'-position of the nucleoside; a heterocyclic base functionalized nucleoside having a folate molecule linked to the heterocyclic base of the nucleoside, a 5' terminal nucleoside having a folate molecule linked to the 5'-position of the nucleoside, a 3' terminal nucleoside having a folate molecule linked to the 3'-position of the nucleoside, or an inter-strand nucleoside having a folate molecule linked to an inter-stand linkage linking said inter-strand nucleoside to an adjacent nucleoside.

Oligonucleotide-folate conjugate compounds have been synthesized by the use of an oligonucleotide that bears a pendant reactive functionality such as that derived from the attachment of a linking molecule onto the oligonucleotide. This reactive oligonucleotide may be reacted directly with commercially available folates or folates that are synthesized bearing a variety of protecting groups. For example, reaction of folic acid with aminolinked oligonucleotides using carbodiimide activation has been reported by Low et al., U.S. Pat. No. 5,108,921. However, this procedure is difficult and of limited utility. In contrast, the methods of the present invention facilitate the synthesis of oligonucleotide-folate conjugates by the use of, in some preferred embodiments, nucleoside monomers that have been appropriately conjugated with folates. Such folate-nucleoside conjugates are prepared according to some preferred embodiments of the methods of the present invention via reaction of pteroic acid derivatives with the desired 2'-aminohexyloxy-nucleoside bearing a glutamate on the pendant 2'-amine. The glutamate may be attached to the nucleoside and linker via either its α- or γ-carboxyl groups. Thus, the methods of the present invention advantageously provide for complete control over the regiochemistry and structure of the conjugate, thus providing a significant benefit over existing synthetic techniques.

It will be appreciated that through the choice of appropriate protecting groups and cleavage reactions, the methods of the present invention allow the regioselective synthesis of α- and γ-isomers of folates conjugated to any desired nucleoside, preferably at the 2'-position of the nucleoside. In addition, conjugates of the invention can also be prepared wherein the folate or folate-linker moiety is attached at other locations on the nucleoside, as described, supra.

In some preferred embodiments, the folate-nucleoside conjugates of the present invention are converted to their corresponding 3'-phosphoramidites via phosphitylation reactions, as described herein. Methods for the use of such phosphoramidites in the synthesis of oligonucleotide-folate conjugates are disclosed herein, and in, for example, Ekstein, supra.

The present invention also provides methods of increasing cellular uptake of an oligonucleotide comprising contacting an organism with an oligonucleotide of the invention.

Oligonucleotide-folate compounds of the present invention can be included in compositions that further include one more inert carrier compounds.

Antisense therapeutics can be practiced in a plethora of various organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to antisense therapeutics and/or prophylactics. Seemingly diverse organisms such as bacteria, yeast, protozoa, algae, all plant and all higher animal forms, including warm-blooded animals, can be treated by antisense therapy. Further, since each of the cells of multicellular eukaryotes also includes both DNA-RNA transcription and RNA-protein translation as an integral part of its cellular activity, antisense therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles can also be included within the definition of organisms that are capable of being treated with antisense therapeutics or diagnostics. As used herein, therapeutics is meant to include both the eradication of a disease state, killing of an organism, e.g. bacterial, protozoan or other infection, or control of erratic or harmful cellular growth or expression.

While we do not wish to be bound by any particular theory, it is believed that the presence of many nuclear proteins in the nucleus is due to their selective entry through the nuclear envelope rather than to their selective retention within the nucleus after entry. By this mechanism, the nucleus is able to selectively take up certain proteins and not others. The uptake is based upon the sequence of the peptide or protein, which provides a selective signal sequence that allows accumulation of the peptide or protein in the nucleus. One such peptide signal sequence is found as part of the SV40 large T-antigen. See: Dingwell and Laskey, *Ann. Rev. Cell Bio.*, 2:367 (1986); Yoneda et. al., "Synthetic Peptides Containing a Region of SV40 Large T-Antigen Involved In Nuclear Localization Direct The Transport Of Proteins Into The Nucleus", *Experimental Cell Research*, 170:439 (1987); and Wychowski et. al., "The Intranuclear Location Of Simian Virus 40 Polypeptides VP2 and VP3 Depends On a Specific Amino Acid Sequence" *J. Virol.*, 61:3862 (1986).

The present invention provides oligonucleotide-folate conjugates that have improved therapeutic properties, including improved transfer across cellular membranes, and also provides methods for the preparation of said oligonucleotide-folate conjugates. In accordance with the present invention there are provided oligonucleotide-folate conjugates and compounds that comprise a plurality of linked nucleosides wherein at least one of the nucleosides is functionalized with a folate molecule, preferably by linking said folate molecule to the nucleoside with a linking moiety.

In accordance with the present invention, a folate molecule is attached to at least one nucleoside in an antisense diagnostic or therapeutic agent to assist in the transfer of the antisense therapeutic or diagnostic agent across cellular membranes. Such antisense diagnostic or therapeutic agent is preferably a nucleic acid or oligonucleotide formed of a plurality of linked nucleosides of a sequence that are "antisense" to a region of an RNA or DNA of interest. Thus one or more nucleosides of the oligonucleotide are conjugated to include a folate molecule linked to the nucleoside with or without the intermediacy of a linking group. For the purposes of identification, such conjugated nucleosides can be characterized as folate bearing nucleosides or folate-nucleoside conjugates. The linked nucleosides having at least one conjugated nucleoside within their sequence demonstrate enhanced antisense activity when compared to like linked nucleoside or oligonucleotides of the same sequence that are not conjugated. The linked nucleosides having at least one functionalized nucleoside within their sequence further demonstrate increased transfer across cellular membranes.

Particularly useful as folate molecules for the preparation of folate conjugates of the present invention are molecules selected from the group consisting of folic acid, dihydrofolic acid, tetrahydrofolic acid, folinic acid, pteropolyglutamic acid, dihydrofolates, tetrahydrofolates, tetrahydropterins, 1-deaza, 3-deaza, 5-deaza, 8-deaza, 10-deaza, 1,5-dideaza, 5,10-dideaza, 8,10-dideaza and 5,8-dideaza folate analogs. The terms deaza and dideaza analogs refers to the art recognized folate analogs that have a carbon atom substituted for one or two nitrogen atoms in the naturally occurring folic acid structure. The foregoing folic acid derivatives are conventionally referred to as folates because they have a structural resemblance to folic acid and because they bind to folate receptors. Folate molecules also include additional molecules that are known to bind to folate receptors and include, but are not limited to, antifolates such as aminopterin, methotrexate, $N^{10}$-methylfolate, 2-desaminohydroxyfolate, 1-deazamethotrexate, 3-deazamethotrexate, and dichloromethotrexate.

Various linking groups are useful for linking folate molecules to nucleosides in accordance with the invention. Preferred linking groups of the invention include, but are not limited to, ω-aminoalkoxy linkers, ω-aminoalkylamino linkers, cysteamine, heterobifunctional linkers, homobifunctional linkers, and a universal linker (derived from 3-dimethoxytrityloxy-2-aminopropanol). A particularly preferred linking molecule for the synthesis of oligonucleotide-folate conjugates of the invention is the 6-aminohexyloxy group.

Linking groups such as ω-aminoalkoxy moieties and ω-aminoalkylamino moieties, are particularly useful for linking molecular groups such as steroid molecules or reporter molecules to, for example, the 2'-position of a nucleoside. A variety of heterobifunctional and homobifunctional linking moieties are available from the Pierce Co. (Rockford, Ill.). Such heterobifunctional and homobifunctional linking moieties are particularly useful in conjunction with the ω-aminoalkoxy and ω-aminoalkylamino moieties to form extended linkers useful for linking peptides, proteins and other molecules such as folates to a nucleoside. Further useful linking groups that are commercially available are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, while the 3'-Amino-Modifier is also available from Clontech Laboratories Inc. (Palo Alto, Calif.). In addition, a nucleotide analog bearing a linking group pre-attached to the nucleoside is commercially available from Glen Research Corporation under the tradename "Amino-Modifier-dT." This nucleoside-linking group reagent, a uridine derivative having an [N(7-trifluoroacetylamino-heptyl)3-acrylamido]

substituent group at the 5 position of the pyrimidine ring, is synthesized as per the procedure of Jablonski, E., Moomaw, E. w., Tullis, R. H. and Ruth, J. L. (1986) *Nucleic Acid Research*, 14:6115. The present invention also includes as nucleoside analogs adenine nucleosides functionalized to include a linker on the N6 purine amino group, guanine nucleosides functionalized to include a linker at the exocyclic N2 purine amino group, and cytosine nucleosides functionalized to include a linker on either the N4 pyrimidine amino group or the 5 pyrimidine position.

The oligonucleotide-folate conjugates of the present invention also include conjugates of oligonucleotides and linked nucleosides wherein the folate is attached directly onto the nucleoside or nucleotide without the intermediacy of a linker group. This attachment of folate may be performed at either one or more of the 2'-, 3'-, 5'-, nucleobase or internucleotide linkage positions of the oligonucleotide or linked nucleosides of the invention. In the compounds and methods of the invention described herein, such structures are represented by those wherein variable $W_1$ is O, NH or S. The attachment of the folate may be performed at either of the α-carboxylate, γ-carboxylate, amino or oxo groups of the folate. Typical linkages may be as ester, amide, or carbamate groups.

The present invention employs oligonucleotides for use in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, turnover or degradation of the mRNA and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as modified oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of repeating units generically known as a nucleotides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the carbon 5 (5') position of the sugar of a first nucleotide and the carbon 3 (3') position of a second, adjacent nucleotide. A "nucleoside" is the combination of (1) a nucleobase and (2) a sugar in the absence of (3) a phosphate moiety (Kornberg, a., *DNA Replication*, W.H. Freeman & Co., San Francisco, 1980, pages 4–7). The backbone of an oligonucleotide positions a series of bases in a specific order; the written representation of this series of bases, which is conventionally written in 5' to 3' order, is known as a nucleotide sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. Antisense oligonucleotides have also been used as diagnostic aids based on their specific binding or hybridization to DNA or mRNA that are present in certain disease states and due to the high degree of sensitivity that hybridization based assays and amplified assays that utilize some of polymerase chain reaction afford. The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections. Other examples of antisense oligonucleotides are provided herein.

The oligonucleotides used in the compositions of the present invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage. In the context of this invention, the term "oligonucleotide" includes oligonucleotides composed of naturally-occurring nucleobases, sugars and covalent intersugar (backbone) linkages as well as oligonucleotides having non-naturally-occurring portions which function similarly. Such modified or substituted oligonucleotides may be preferred over native forms because of desirable properties such as, for example, enhanced cellular uptake, enhanced binding to target and increased stability in the presence of nucleases.

Specific examples of some preferred modified oligonucleotides envisioned for use in the oligonucleotide-folate conjugates of the present invention include oligonucleotides containing modified backbones or non-natural intersugar linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified, and in fact more than one of the following modifications may be incorporated in a single antisense compound or even in a single residue thereof, for example, at a single nucleoside within an oligonucleotide.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States Patents that teach the preparation of the above phosphorus atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified oligonucleotide backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation c he above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,6C2,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497.

Some preferred embodiments of the present invention may employ oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the oligonucleotide-folate conjugates of the present invention may additionally or alternatively comprise nucleobase (often referred to in the art simply as "base") modifications or substitutions. As used herein, "unmodified" or "natural" nucleobases include the purine bases adenine (a) and guanine (G), and the pyrimidine bases thymine (T), cytosine © and uracil (U). Modified nucleobases include other synthetic and natural nucleobases such as 5-mrethylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941, certain of which are commonly owned, and each of which is herein incorporated by reference, and commonly owned U.S. patent application Ser. No. 08/762,488, filed on Dec. 10, 1996, also herein incorporated by reference.

The oligonucleotides employed in the oligonucleotide-folate conjugates of the present invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O—CH$_2$CH$_2$OCH$_3$, also known as 2'-O-(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a O(CH$_2$)$_2$ON(CH$_3$)$_2$ group, also known as 2'-DMACE, as described in co-owned U.S. patent application Ser. No. 09/016,520, filed on Jan. 30, 1998, the contents of which are herein incorporated by reverence.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the oligonucleotide-folate conjugates of the present invention involves chemically linking to the oligonucleotide one or more additional non-folate moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned, and each of which is herein incorporated by reference.

The present invention also includes compositions employing antisense compounds which are chimeric compounds. "Chimeric" antisense compounds or "chimeras," in the context of this invention, a-e antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oliconucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oliconucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids, and ribozymes are not comprehended by the present invention.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy-substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that Leach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed on Jun. 6, 1995, also herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

The present invention further encompasses oligonucleotide-folate conjugates employing ribozymes. Synthetic RNA molecules and derivatives thereof that catalyze highly specific endoribonuclease activities are known as ribozymes. (See, generally, U.S. Pat. No. 5,543,508 to Haseloff et al., issued Aug. 6, 1996, and U.S. Pat. No. 5,545,729 to Goodchild et al., issued Aug. 13, 1996.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83, 8859; Forster et al., *Cell*, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

The oligonucleotides used in the conjugates of the present invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

Teachings regarding the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

In the oligonucleotide-folate conjugates and folate molecule-bearing sequence-specific linked nucleosides of the present invention, the nucleosides are assembled on a suitable DNA synthesizer utilizing standard nucleotide precursors, or nucleotide conjugate precursors that already bear the linking moiety, or folate-nucleoside conjugate precursors that already bear the folate molecule.

When using nucleotide conjugate precursors that already bear a linking moiety, the synthesis of the sequence-specific linked nucleosides is typically completed, and the folate molecule is then reacted with the linking moiety to form the oligonucleotide-folate conjugate. This approach to the synthesis of oligonucleotide conjugates bearing a variety of molecules such as steroids, vitamins, lipids and reporter molecules has previously been described. See Manoharan et al., PCT Application WO 93/07883. In a preferred embodiment the oligonucleotides or linked nucleosides of the present invention are synthesized by an automated synthesizer using phosphoramidites derived from folate-nucleoside conjugates in addition to the standard phosphoramidites used in oligonucleotide synthesis.

In U.S. application Ser. No. 91/00243, application Ser. No. 463,358 and application Ser. No. 566,977, all incorporated herein by reference, it is reported that incorporation of a 2'-O-methyl, 2'-O-ethyl, 2'-O-propyl, 2'-O-allyl, 2'-O-aminoalkyl or 2'-deoxy-21-fluoro group in nucleosides of an oligonucleotide confers enhanced hybridization properties to the oligonucleotide. It is further reported that oligonucleotides containing phosphorothioate backbones have enhanced nuclease stability. Thus, functionalized, linked nucleosides of the invention can be augmented to further include either or both a phosphorothioate backbone or a 2'-O-methyl, 2'-O-ethyl, 2'-O-propyl, 2'-O-aminoalkyl, 21-O-allyl or 2'-deoxy-2'-fluoro group thereon.

In some preferred embodiments, functionalized nucleoside sequences of the invention possessing an amino group at the 5'-terminus is prepared using a DNA synthesizer, and then reacted with an active ester derivative of folic acid. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which folic acid is attached to the 5'-position through a linking group. The amino group at the 5'-terminus can conveniently be prepared utilizing the above noted 5'-Amino-Modifier C6 reagent. In a preferred embodiment, folate molecules may be conjugated to oligonucleotides at the 5'-position by the use of a folate-nucleoside phosphoramidite wherein the folate is linked to the 5'-hydroxy group directly or indirectly via a linker. Such folate-nucleoside phosphoramidites are typically used at the end of an automated synthesis procedure to provide an oligonucleotide-folate conjugate bearing the folate molecule at the 5'-terminus.

In further preferred embodiments, functionalized nucleoside sequences of the invention can be prepared wherein folic acid is attached to the 3'-terminal amino group using a 3'-amino modified controlled pore glass (sold by Clontech Laboratories Inc., Palo Alto, Calif.) and subsequent attachment of the folic acid is achieved by reaction with a folic acid active ester.

In another preferred embodiment of the present invention, the folate may be attached to the oligonucleotide at the 3'-terminus through the use of an appropriate multifunctional linker such as a universal linker. In this case the folate is first derivatized with the universal linker and this conjugate then loaded onto a solid support. Subsequent synthesis of nucleic acids or oligonucleotides on this solid support affords upon cleavage and deprotection the oligonucleotide-folate conjugate bearing a folate molecule at the 3'-terminus.

In still further preferred embodiments, functionalized sequences of nucleosides and oligonucleotide-folate conjugates of the present invention can be prepared wherein the folate molecule is attached either directly or via a linking group to any one of the atoms of the nucleobase of any of the nucleoside units of the oligonucleotide. Thus, one or more folate molecules may be attached to the nucleobase at the 3'-terminus, the 5'-terminus or any position in between. Such attachment can be accomplished, for example, by chemistries described in the literature, and mentioned above. The preferred mode of attachment of folate molecules to nucleobases is via the intermediacy of an appropriate linker present on a nucleoside precursor. The folate-nucleoside conjugate is then phosphitylated at the 3'-position to afford a folate-nucleoside conjugate phosphoramidite which may be used subsequently as a building block together with traditional nucleoside phosphoramidites for the automated synthesis of oligonucleotides. The number and location of insertion of such folate nucleotide conjugate phosphoramidites will then dictate the number and location of folate molecules present in the synthesized oligonucleotide-folate conjugate of the present invention.

The present invention also provides oligonucleotide-folate conjugates wherein the folate molecule is attached to one of the atoms of the internucleotide linkage. One typical internucleotide linkage in nucleic acids and oligonucleotides is the phosphodiester linkage. Numerous modified internucleotide linkages are known in the art including, but not limited to, phosphorothioate, methyl phosphonate, and phosphordithioate, as described above. Folate molecules may be conjugated at one of the atoms of such internucleotide linkages with or without the intermediacy of a linking group. Attachment of the folate molecule may be accomplished in accordance with the methods of the invention either during the preparation of the nucleoside building block such as the phosphoramidite or may be performed during the formation of the internucleotide linkage during oligonucleotide synthesis.

In addition to the multiple sites on an oligonucleotide where a folate molecule may be attached, there exist multiple sites on the folate molecule through which the conjugation may occur. In accordance with the present invention the folic acid component of the oligonucleotide-folic acid conjugate can be attached at one of, but not limited to, the α-carboxylate, the γ-carboxylate, or amino group of the folate. Most preferred among the various available sites for conjugation are the α-carboxylate and the γ-carboxylate of the folic acid molecule, or derivative thereof. Conjugation is typically performed using an aminoalkyl linker via an amide bond.

In further preferred embodiments of the invention, the folate molecule is attached at multiple sites on one oligonucleotide. For example, oligonucleotide-folate conjugates can be prepared wherein one or more folates are attached to both ends of a linked nucleoside sequence. Preferably such a structure is prepared by reacting a 3',5'-diamino sequence with a folic acid active ester. The required oligonucleoside sequence can be synthesized, for example, utilizing the 3'-Amino-Modifier and the 5'-Amino-Modifier C6 (or Aminolink-2) reagents noted above or by utilizing the above noted 3'-amino modified controlled pore glass reagent in combination with the 5'-Amino-Modifier C2 (or Aminolink-2) reagents. Alternatively, such multiply conjugated oligonucleotides may readily be synthesized according to the methods of the invention using an appropriate folate-nucleoside conjugate phosphoramidites as and where needed in a given oligonucleotide sequence during automated synthesis.

In still further preferred embodiments of the invention, an oligonucleoside sequence bearing an aminolinker at the 2'-position of one or more selected nucleosides is prepared using a suitably functionalized nucleotide such as, for example, 5'-dimethoxytrityl-2'-O-(ε-phthalimidylaminopentyl)-2'-deoxyadenosine-3'-N,N-diisopropyl-cyanoethoxy phosphoramidite. See the above referenced U.S. patent applications Ser. Nos. 91/00243, 566, 977 and 463,358. Preferably, the nucleotide or nucleotides are attached to the folic acid by reaction with an active ester or a thioisocyanate thereof, at one or more of the nucleoside components of the oligonucleotide.

In yet further preferred embodiments, functionalized nucleoside sequences of the invention can be prepared wherein the heterocyclic base of one or more nucleosides can be linked to a folate molecule. For example, utilizing 5'-O-dimethoxytrityl-5-[N(7-trifluoroacetylaminoheptyl)-3-acrylamido]-2'-deoxyuridine 3'-O-(methyl N,N-diisopropyl)-phosphoramide as described by Jablonski et. al. supra (also commercially available from Glen Research) the desired nucleoside, functionalized to incorporate a linking group on its heterocyclic base, is incorporated into the linked nucleoside sequence using a DNA synthesizer.

In further functionalized linked nucleosides of the invention, conjugation (or linking) of folate molecules is achieved by conjugation of the folate to the above described amino linking group on the nucleoside. This can be effected in several ways. For example, a folate-nucleoside conjugate of the invention can be prepared by conjugation of the folate molecule to the nucleoside using EDC/sulfo-NHS (i.e. 1-ethyl-3(3-dimethylaminopropylcarbodiimide/N-hydroxysulfosuccinimide) to conjugate the carboxylate function of the folate with the amino function of the linking group on the nucleoside.

Oligonucleotide-folate conjugates of the present invention may be prepared by conjugation of the folate molecule to the nucleoside sequence via a heterobifunctional linker such as m-maleimidobenzoyl-N-hydroxysulfosuccinimide ester (MBS) or succinimidyl 4-(N-maleimidomethyl) cyclohexane-1-carboxylate (SMCC), to link a nucleophilic position, preferably a thiol, on the folate molecule to the amino function of the linking group on nucleoside sequence. By this mechanism, an oligonucleoside-maleimide conjugate is formed by reaction of the amino group of the linker on the linked nucleosides with the MBS or SMCC maleimide linker. The conjugate is then reacted with folate molecules, preferably those that possess a thiol functionality.

Alternatively, an oligonucleotide-folate conjugate can be prepared by conjugation of the folate molecule to the oligonucleotide or nucleoside via a homobifunctional linker such as disuccinimidyl suberate (DSS), to link an amino function on the folate to the amino group of a linker on the oligonucleotide sequence. By this mechanism, an oligonucleoside-succinimidyl conjugate is formed by reaction of the amino group of the linker on the nucleoside sequence with a disuccinimidyl suberate linker. The disuccinimidyl suberate linker couples with the amine linker on the nucleoside to extend the size of the linker. The extended linker is then reacted with an amino group of the folate molecule.

A number of non-folate molecules have been conjugated to oligonucleotides in order to enhance the activity, cellular distribution or cellular uptake of the oligonucleotide, and procedures for performing such conjugations are available in the scientific literature. Such non-folate moieties have included lipid moieties such as cholesterol (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block such as a phosphoramidite via an alcohol group present in the molecule or by attachment of a linker bearing an alcohol group that may be phosphitylated.

Each of these approaches may be used for the synthesis of oligonucleotide-folate conjugates. Aminolinked oligonucleotides may be coupled directly with folic acid via the use of coupling reagents or following activation of the folic acid as an NHS or pentfluorophenolate ester. While this procedure does afford the oligonucleotide-folic acid conjugate, the yield is low and the reaction affords a mixture of the α-conjugate and γ-conjugate formed via attachment of the α-carobylic acid and the γ-carboxylic acid of folic acid to the amino group of the oligonucleotide. Folic acid phosphoramidites may be synthesized via the attachment of an aminohexanol linker to one of the carboxyl groups followed by phosphitylation of the terminal alcohol functionality. Other linkers such as cysteamine may also be utilized for conjugation to a chloroacetyl linker present on a synthesized oligonucleotide.

The foregoing approaches can afford oligonucleotide-folate conjugates. However, they are limited by the nature of the folate that may be coupled because of the common insolubility of many folates and folate analogs. Further, these approaches lack regioselectivity, because of the two similar carboxylic groups present in many folates, and will often afford a mixture of α- and γ-conjugates that may result in variability in the biological effects observed when studying such conjugates. Because these conjugations are post-synthetic, that is, after automated synthesis of the oligonucleotide has been performed, these approaches are limited to providing conjugates at only those positions that may be derivatized during automated synthesis and subsequently reacted with folate.

The methods of the present invention also provide synthetic paths that circumvent the solubility and regioselectivity problems of such conventional conjugations of folic acid and related folates, by using a novel conjugation approach that constructs the folate from its three major components during the process of conjugation.

Most folates are comprised of three portions: a pterin, p-aminobenzoic acid and glutamic acid which together form the pteroyl-p-aminobenzoylglutamate strutre of folic acid. In preferred embodiments, the methods of the present invention provide for the synthesis of oligonucleotide-folate conjugates via first attachment of appropriately protected glutamic acid or other amino acids such a homoglutamic acid and aspartic acid to a nucleoside precursor or oligonucleotide. This attachment is preferably performed via an acylation reaction at the amine functionality of an amino linker present on the nucleoside or oligonucleotide. An appropriate pteroyl-p-amino benzoic acid is then condensed with the pendant amino group of the previously conjugated glutamic acid. This two step conjugation reaction is affords significant benefits over current synthetic methods, including the elimination of all the problems associated with poor solubility of folates during conjugation reactions. In addition, because of the availability of many different selectively protected lutamate and other amino acids, the methods of this invention provide tremendous regioselectivity and control over the nature of the oligonucleotide-folate conjugate that may be synthesized.

The methods of the invention provide for the preparation of a variety of folate compounds wherein the glutamic acid moiety of the folic acid is replaced with another amino acid, preferably a naturally occurring amino acid. As used herein, the term "naturally occurring amino acid" is intended to mean amino acids found in nature, for example the α-amino acids having the formula HOOC—CH(sidechain)—NH$_2$ that occur in living organisms. Representative sidechains of naturally occurring amino acids include the glutamyl side chain (—(CH$_2$)$_2$—COOH), the aspartyl sidechain (—CH$_2$—COOH). Further representative sidechains of naturally occurring amino acid can be found in Lehninger, *Biochemistry*, Second Edition, Worth Publishers, Inc, 1975, pages 73–75, which is incorporated by reference herein.

The methods of the present invention allow for the selective synthesis of each of the two regioisomeric oligonucleotide-folate conjugates that may be formed by reaction of folic acid at either the α-carboxylate or the γ-carboxylate, by systematically constructing the folate conjugate. Because glutamic acid is available in a number of different selectively protected derivatives, the α-carboxylate of glutamic acid may be selectively reacted with a pendant amino group on a nucleoside by using the γ-t-butyl ester of N-Fmoc glutamic acid. Likewise, the γ-carboxylate of glutamic acid may be selectively reacted with a pendant amino group on a nucleoside by using the α-t-butyl ester of N-Fmoc glutamic acid. Subsequent reaction with pteroic acid, according to the methods of the invention affords selectively both regioisomers of the oligonucleotide-folate conjugate as discrete compounds of the methods of the invention.

In one preferred embodiment of the methods of the invention, the preparation of oligonucleotide-folate conjugates of the present invention commences with the selection of appropriate precursor molecules upon which to construct the folate molecule. Typically the precursor is an appropriately protected derivative of the commonly used nucleosides. For example, the synthetic precursors for the synthesis of the oligonucleotide-folate conjugates of the present invention include, but are not limited to, 2'-ω-aminoalkoxy-5'-ODMT-nucleosides, 2'-ω-aminoalkylamino-5'-ODMT-nucleosides, 5'-ω-aminoalkoxy-2'-deoxy-nucleosides, 5'-ω-aminoalkyxy-2'-protected-nucleosides, 3'-ω-aminoalkoxy-5'-ODMT-nucleosides, and 3'-aminoalkylamino-5'-ODMT-nucleosides that may be further protected in the nucleobase portion of the molecule. The use of such precursors is anticipated to afford oligonucleotide-folate conjugates where attachment is at one of many possible sites such as the 2', 3' or 5' position of one or more of the nucleoside components of oligonucleotides. Methods for the synthesis of such aminolinked protected nucleoside precursors are known to the art skilled and are available in the literature.

In accordance with preferred embodiments of the methods of the invention, the aminolinked protected nucleoside precursors are first reacted with an appropriately protected amino acid, preferably glutamic acid, more preferably the α-t-butyl ester of N-Fmoc glutamic acid or the γ-t-butyl ester of N-Fmoc glutamic acid. Alternate protecting groups that may be used for the pendant carboxylate group include the O-allyl ester. Coupling of the free carboxylate of the glutamic acid with the available amino group pendant from the nucleoside precursor is performed, for example, using dicyclohexylcarbodiimide (DCC) and HONB as activating reagent in anhydrous DMF. In some preferred embodiments, 2'-O-(hexylamino)-5'-ODMT-5-methyl-uridine is reacted with N-Fmoc-α-t-butyl-L-glutamic acid affords the corresponding nucleoside-γ-glutamic acid conjugate. Likewise reaction of 2'-O-(hexylamino)-5'-ODMT-uridine with N-Fmoc-γ-t-butyl-L-glutamic acid affords the corresponding nucleoside-α-glutamic acid conjugate. The methods of the present invention, in addition to their utility in the preparation of such nucleoside-amino acid conjugates, are also applicable for the synthesis of a variety of other conjugates derived from other nucleosides and amino acids.

In some preferred embodiments, nucleoside-glutamic acid conjugates prepared according to the methods of the present invention are next treated with a deprotecting reagent such as, but not limited to, a mixture of 0.1 M DBU in acetonitrile or a 10% solution of piperidine in acetonitrile, to cleave the pendant amine protecting group such as the Fmoc group (i.e., "deprotection"). In further preferred embodiments, the intermediate nucleoside-glutamic acid conjugates of the invention are then reacted with a pteroyl-p-aminobenoate to provide the folate molecule.

The pteroyl-p-aminobenzoate intermediate necessary for the construction of folate conjugates may also be synthesized according to the methods of the present invention. While many syntheses of folic acid and related folates are available in the literature, most of these syntheses tend to be costly, multistep and tedious in nature. Thus, in accordance with preferred embodiments of the invention, the an appropriately substituted and protected pteroyl-p-aminobenzoate can be synthesized via a novel set of reactions according to the methods of the present invention. In preferred embodiments, the oxidative cleavage of folic acid is effected using, for example, a mixture of HBr and bromine at 95–100° C. Significantly, the methods of the present invention provide an increased yield of the desired pterin-aldehyde intermediate, by performing the oxidative cleavage under conditions of elevated temperature and pressure. Thus, the present invention provides methods for the synthesis of pterin aldehyde, and methods for the preparation of folate-oligonucleotide conjugates using the pterin aldehyde.

In preferred embodiments, selective protection of the amino group of the pterin aldehyde is then performed. For example, the 2-amino group of the pterin aldehyde obtained from folic acid can be treated with isobutyric anhydride at a temperature of 130° C. for 30 hours to afford N2-isobutyrl-6-formyl pterin. The 4-oxo moiety of the pterins may also be protected as the diphenylcarbamate species by using diphenylcarbamoyl chloride as reagent.

In accordance with further preferred embodiments, the N2-isobutyryl-6-formyl pterin intermediates can then be subjected to reductive amination using commercially available p-aminobenzoic acid with, for example, pyridine-borane complex in the presence of PPTS, as proton source, to produce N2 isobutyrylpteroic acid. Preferably, the intermediate is then further protected by, for example, conversion of the N10-functionality to a $N^{10}$-trifluoroacetyl group via reaction with, for example, trifluoroacetic anhydride at room temperature.

In further preferred embodiments, the pteroic acid derivative is coupled with the ω-aminoalkoxy nucleoside to obtain a folate-nucleoside conjugate. This coupling of the pteroic acid derivative and the w-aminoalkoxy nucleoside may be performed using any one of a variety of reagents, including but not limited to HONB/DCC, HATU, HBTU and PyBrop. More preferred is the use of PyBroP in the presence of a non-nucleophilic amine as a base to neutralize the HBr that is generated during the coupling reaction. The folate-nucleoside conjugate so synthesized according to the methods of the invention is typically isolated in yields of about 40–50%. In some prefered embodiments, the folate-nucleoside conjugate is then subjected to a phosphitylation reaction using conventional reagents to afford the corresponding folate-nucleoside conjugate phosphoramidite in yields of about 60–70%.

Both α-folic acid conjugate phosphoramidites and γ-folic acid conjugate phosphoramidites are synthesized following the methods of the present invention described herein. Use of such amidites derived from different nucleosides afford a variety of different oligonucleotide-folate conjugates of the present invention. Typically, the folate-nucleoside phosphoramidites of the present invention are used during automated oligonucleotide synthesis as solutions in dry dichloromethane, dimethyl formamide or acetonitrile using coupling times in excess of those used for the standard phosphoramidites.

Phosphoramidites may also be synthesized from the intermediate protected nucleoside conjugates such as, for example, the glutamic acid-nucleoside conjugate. These amidites may also be used according to the methods of the present invention to provide oligonucleotide conjugates.

The use of t-butyl protecting groups for pendant carboxylate groups of the glutamate portion of the conjugates of the present invention allows for facile cleavage of the t-butyl ester. However, in instances where this protecting group is difficult to remove using the conventional cleavage reagents of TFA and TFA in dichloromethane, other protecting groups such as the O-allyl group may be used.

The oligonucleotide-folate conjugates of the present invention are expected to exhibit enhanced transport into cells compared to the parent oligonucleotides. The conjugation with the folates facilitates the active transport of the conjugates of the present invention via receptor mediated endocytosis following recognition of the folate by membrane folate binding receptors and transporters. Since folate binding receptors and transporters are widely present in a variety of cells and tissues, the oligonucleotide-folate conjugates of the present invention are anticipated to deliver higher levels of oligonucleotide into these cells and tissues.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

As used herein, the term "alkanoyl" has its accustomed meaning as a group of formula —C(=O)-alkyl. A preferred alkanoyl group is the acetoyl group.

In general, the term "hetero" denotes an atom other than carbon, preferably but not exclusively N, O, or S. Accordingly, the term "heterocycle" denotes a cyclic structure having at least one non-carbon atom.

Additional objects, advantages, and novel features of this invention will become apparent to those skilled in the art upon examination of the following examples, which are not intended to be limiting.

For the following examples, anhydrous dimethylformamide, folic acid and N-hydroxysuccinimide were purchased from Aldrich Chemical Co. (Milwaukee, Wis.), ethyl-3-(3-dimethylamino)propylcarbodiimide (EDAC or EDC) was obtained from JBL Scientific (San Luis Obispo, Calif.) as the free base under the label EDAC or from Pierce (Rockford, Ill.) under the label EDC, Aminolink-2 was purchased from ABI and 3'-Amino-Modifier, 5'-Amino-Modifier C6 and Amino-Modifier dT reagents were purchased from Glen Research Corporation. NMR Spectra were run on a Varian Unity-400 instrument. Oligonucleotide synthesis were performed on an Applied Biosystems 380 B or 394 DNA synthesizer following standard phosphoramidite protocols using reagents supplied by the manufacturer. When modified phophoramidites were used, a longer coupling time (10–15 min) was employed. HPLC was performed on a Waters 600E instrument equipped with a model 991 detector. Unless otherwise noted, for analytical chromatography the following conditions were employed: Hamilton PRP-1 column (15×2.5 cm); solvent a: 50 mm TEAA, pH 7.0; solvent B: 45 mm TEAA with 80% $CH_3CN$; flow rate: 1.5 ml/min; gradient: 5% B for the first 5 minutes, linear (1%) increase in B every minute thereafter and for preparative purposes: Waters Delta Pak C-4 column; flow rate: 5 ml/min; gradient: 5% B for the first 10 minutes, linear 1% increase for every minute thereafter.

All oligonucleotide sequences are listed in a standard 5' to 3' order from left to right.

EXAMPLES

Example 1

6-Formylpterin (21)

Folic acid (20 g, 45 mmole) was added to a stirred solution of bromine(36;2 g, 226.5 mmole) in 40% hydrogen bromide (120 ml) in a one liter pressure bottle. When all the folic acid was dissolved, the solution was heated to 90–95° C. for two hours with continuous stirring. The resulting yellow precloitate was collected by filtration, washed thoroughly with water and the solid cake was extracted with hot acetone. The product was dried in vacuum at 50° C. to furnish the desired 6-formylpterin 21 as a yellow powder, yield=6.7 g 78%, $^1H$ NMR (TFA): δ 10.21 (s, 1H), 9.46 (s, 1H). These chemical shifts agree with standard 6-formylpterin obtained from Aldrich Chemical Co. Mass spec, 30 m/z, M-H$^+$=192 for $C_7H_5N_5O_2$.

Example 2

$N^2$-Isobutyryl-6-formylpterin (25)

6-Formylpterin 21, (5 g) was suspended in isobutyric anhydride (250 ml) and heated under argon at 130° C. with continuous stirring until all sold had dissolved (30 hours). The reaction mixture was cooled to room temperature, and then placed in refrigerator for 24 hours. The precipitated product was collected by filtration and washed thoroughly with hexanes and the last with 1:1 mixture of hexanes/IPA. The light cream colored $N^2$-iBu-6-formylpterin was dried in vacuo at 50° C., and resulted in 5 g (75%) clean product, which was used without further purification. $^1H$ NMR (DMSO): 10.10 (s, 1H), 9.30 (s, 1H) 2.80–2.86 (m, 1H), 1.15–1.18 (2s, 6H).

Example 3

$N^2$-Isobutyryl-pteroic Acid (26)

$N^2$-iBu-6-formylpterin (25) 4.0 gm, 15 mmole) was suspended in MeOH. To this suspension was added 4-aminobenzoic acid (2.1 g, 15 mmole) followed by stirring for 10 minutes. The reaction mixture was then cooled in an ice bath with continuous stirring. A solution of pyridinium para-toluene sulfonate (PPTS, 1 M in MeOH, 15 ml, 15 mmol) was added in one portion, followed by the addition of pyridine-borane complex (1.9 ml of 8M solution, 15 mmol) dropwise over a period of 10 minutes. The ice bath was removed, and stirring was continued at room temperature for 3 hours. The fine precipitated product was collected by centrifugation and washed with a 1:1 mixture of hexanes-MeOH several times, and finally with MeOH. The product was dried in vacuum over $P_2O_5$ for 24 sours to give light cream-colored powder, yield=5.3 gm, 91%. $^1H$ NMR (DMSO): δ 8.87 (s, 1H), 4.62 (s, 2H), 2.75–2.82 (m, 1H), 1.13, 1.16 (2s, 6H); MS, m/z, M-H$^+$=383 for $C_{18}H_{18}N_6O_4$.

Example 4

$N^2$-Isobutyryl-N10-trifluoroacetylpteroic Acid (27)

$N^2$-isobutyryl-pteroic acid 26 (1.5 gm, 3.9 mmol) was dried over $P_2O_5$ for 24 hours under reduced pressure and then placed in a round bottom flask. To this was added triflouroacetic anhydride (32 ml) dropwise over 30 minutes with continuous stirring. The reaction mixture was protected from light and moisture and was stirred at room temperature until all sold had dissolved, and the stirring was continued for an additional one hour. The trifluoroacetic anhydride was then removed under reduced pressure and MeOH was added to the remaining dark syrup, followed by stirring for one hour. A cream-colored precipitate was obtained which was collected by filtration and washed with MeOH three times and then twice with $CH_2Cl_2$. The material was dried for 24 hours over $P_2O_5$ under reduced pressure to yield 1.26 g (70%) of compound 27 as a light cream-colored powder. $^1H$ NMR (DMSO): δ 8.91 (s, 1H), 5.25 (s, 2H) 2.76–2.83 (m, 1H). 1.13, 1.17 (2s, 6H) MS m/z MH$^+$=479 for $C_{20}H_{17}N_6O_5F_3$.

Example 5

2'-O-(N-Fmoc-a-tert.Butyl-g-L-glutamyl)-aminohexyl-5'-O-DMT-uridine (30)

To a solution of N-Fmoc-a-tert.butyl protected L-glutamic acid 28 (1.3 g, 3.0 mmol) in anhydrous DMF (7 ml) was added DCC (1.0 gm, 4.8 mmol) and HONB (0.85 gm, 4.7 mmol) successively and the reaction was allowed to stir for 30 minutes to make the active ester. After this time compound 18 (2.3 gm, 3.5 mmol) was added to the reaction mixture and the stirring was continued for 7 hours, when the tic system (50:40:10 EtOAc:hexane:MeOH) indicated the completion of the reaction. It was diluted with EtOAc (200 ml), washed with brine (3×25 ml). The organic layer was dried over anhydrous $Na_2SO_4$, concentrated to a form, and purified by column chromatography on silica gel using the above solvent system to furnish a residue which had couple of impurities. The product was repurified by column chromatography using 30% acetone in $CH_2Cl_2$. The appropriate fractions were collected and concentrated to furnish 30 as a white foam, yield=2.0 gm, 61%. $^1H$ NMR (CDCl$_3$): δ 9.60 (bs, 1H), 8.00 (d, 1H, J=8.2 Hz), 7.74 (d, 2H, J=7.3 Hz), 7.61–7.57 (m, 2H), 7.37–7.25 (m, 13H) 6.85–6.81 (m, 4H), 6.22 (m, 1H), 5.93 (bs, 1H), 5.83 (d, 1H, J=7.9 Hz), 5.55 (d, 1H, J=7.9 Hz) 4.44–2.82 (m, 21H), 2.23–1.04 (m, 19H+ some DCU).

Example 6

2'-O-(N-Fmoc-a-tert.Butyl-g-L-glutamyl)-aminohexyl-5'-O-DMT-5-methyl-uridine (31)

This compound was prepared by following the similar method as described for compound 30. Thus from 28 (2.6 gms, 6.1 mmol) 29 (4.6 gm, 6.9 mol), DCC (2.0 gm, 9.6 mmol) and HONB (1.7 gm, 9.5 mmol) in anhydrous DMF (15 ml), after 10 hours of stirring at room temperature and the usual workup described for compound 30, followed by the chromatographic purification using 5% isopropanol in $CH_2Cl_2$ as the eluant to give desired conjugate as a foam, yield 4.5 gm, 60%.

Example 7

2'-O-(α-tert.Butyl-g-L-glutamyl)-aminohexyl-5'-O-DMT-uridine (32)

A solution of 30 (0.76 gm, 0.72 mmol) was stirred in 0.1 M DBU (20 ml) for 1 hour at which time the tlc system (7% MeOH in $CH_2Cl_2$) showed the completion of the reaction. The solvent was removed under educed pressure and the residual oil was purified by flash chromatography on silica-gel using 10% MeOH in $CH_2Cl_2$. The fractions containing the desired compound were concentrated to furnish the free amino acid as a white foam, yield=0.40 gm, 67%.

Example 8

2'-O-(α-tert-Butyl-g-L-glutamyl)-aminohexyl-5'-O-DMT-5 Methyl-uridine (33)

This compound was essentially prepared by the same method as described for 32 with some minor changes in the workup. Therefore, compound 31 (3.8 gm, 3.56 mmol) was treated witch 0.1M DBU (100 ml) for 1.2 hours, at which time the deprotection was complete. The soliution was concentrated to dryness and the residue dissolved in EtOAc (100 ml) and washed with water (2×30 ml). The organic layer dried as usual and the compound purified by column chromatography using 7% MeOH to give the desired derivative 33 as a colorless foam, yield=2.3 gms, 76% 1H NMR (DMSO-$d_6$): δ 7.77–7.55 (m, 1H), 7.52 (s, 1H), 7.39–7.26 (m, 9H) 6.94–6.90 (m, 4H), 5.86 (d, 1H, J=4.6 Hz), 5.20 (bs, exg. 1H), 4.25 (hs, 1H), 4.04–3.97 (m, 1H), 3.75 (s, 6H), 3.67–2.97 (m, 6.H) 2.10–2.0 (m, 3H) 1.9–1.28 (m, 17H).

Example 9

5'-O-DMT-2'-O-Aminohexyl-uridine-$N^{10}$-trifloroacetyl-α-tert-butyl-folic Acid-γ-cojugate (35)

To a solution of $N^{10}$-TFA-pteroic acid, 34 from Aldrich Chemical Co. (0.1 gm, 0.24 mmol) in anhydrous DMF (1.5 ml) was added PyBrOP (bromo-tris-pyrrolidino-phosphonium hexafluorophosphate, 0.12 gm, 0.25 mmol) and the suspension was stirred for 15 minutes. To this mixture was added DIPEA (diisopropylethylamine, 0.063 gm, 0.48 mmol) when the reaction mixture became a thick Gel. After breaking the thick gel by agitation, it was stirred for 25 minutes and at this point anhydrous DMF (1 ml) was added to effect a suspresnion. To this suspension was added nucleoside-linked glutamic acid derivative 32 (0.20 gm, 0.24 mmol), when the reaction became a clear solution in 5–7 minutes. The mixture was stirred for 15 hours after which time the tic system (15% MeOH/$CH_2Cl_2$) showed the completion of the reaction. The reaction mixture was diluted with $CH_2Cl_2$ (30 ml) and purified by column chromatography on silicagel using 10% MeOH/$CH_2Cl_2$ as the eluent. The fluorescent faction along with the other less polar impurities was eluted fairly quickly because of the presence of DMF in the reaction mixture. The appropriate fractions were collected and concentrated to minimum volume and then addition of $CH_3CN$ (1 ml) Furnished a solid which was collected by filtration and washed with $CH_3CN$, the solid was dried under vacuum for 3 hours to give the desired nucleoside-folicacid conjugate (35) as a single spot compound yield=0.085 gm. The mother liquor was concentrated and re-chromatographed using 7–10% MeOH/$CH_2Cl_2$ and after usual treatment furnished an additional 0.035 gm, giving final yield of 40% of the desired compound. $^1$H NMR, 400 MHz (DMSO-$d_6$): δ 11.37 (s, 1H), 8.76 (d, 1H, J=7.2 Hz), 8.61 (s, 1H), 7.88 (d, 2H, J=8.4 Hz), 7.78 (bs, 1H), 7.72 (d, 1H, J=8.0 Hz), 7.61 d, 2H, J=8.0 Hz), 7.37–7.22 (m, 9H), 6.88 (d, 4H, J=8.8 Hz), 5.77 (bs, 1H), 5.27 (d, 1H, J=8.4 Hz) 5.12–5.10 (m, 3H), 4.25–4.15 (m, 2H), 3.94–3.87 (m, 2H), 3.72 (s, 6H), 3.59–3.47 (m, 2H), 3.82–3.20 (m, 7H), 2.98–2.97 (m, 2H), 2.18–1.88 (m, 4H), 1.47–1.22 (m, L3H); $^{13}$C NMR (DMSO-$d_6$): δ 171.03, 165.61, 162.99, 158.11, 156.74, 155.77, 155.40, 154.07, 150.26, 149.39, 144.62, 144.00, 141.52, 140.21, 135.33, 135.05, 134.44, 129.75, 128.68, 128.37, 128.11, 127.90, 127.68, 126.79, 117.52, 114.66, 113.23, 101.45, 87.113, 85.87, 82.60, 80.86, 80.55, 69.81, 68.45, 62.59, 55.03, 53.78, 53.15, 31.74, 29.06, 27.63, 26.32, 26.21, 25.12; ESMS (-ive ion) M-1, 1219.3 which agrees with $C_{61}H_{67}N_{10}O_{14}F_3$.

Example 10

5'-O-DMT-2'-O-Aminohexyl-uridine-$N^{10}$-trifloroacetyl-α-tert-butyl-folic Acid-γ-cojugate 3'-Phosphoramidite (36)

To a suspension of compound 35 (0.11 gm, 0.09 mmol) was added DIPEA (0.029 gm, 0.22 mmol) and the reaction mixture was stirred for 10 minutes when 2-cyanoethoxy N,N-diisopropylchlorophosphoramidite (0.027 gm, 0.11 mmol). The reaction mixture was stirred for 2 hours when the reaction was complete. The reaction mixture was loaded directly onto silicagel column and it was eluted with 10% MeOH/$CH_2Cl_2$, the appropriate fractions were collected and concentrated to give the desired phophoramidite as solid. Yield=0.085 gms, 66%; $^{31}$P NMR (CDCl$_3$): δ 150.91, 150.52 (with some impurity 8%, at 121.91 ppm).

Example 11

2'-O-(N-Fmoc-γ-tert.Butyl-α-L-glutamyl)-aminohexyl-5'-O-DMT-uridine (38)

To a solution of N-Fmoc-L-glutamic acid-g-tert.butyl ester (1.5 gm, 3.25 mmol) in anhydrous DEF (7 ml) was added DCC (1.0 gm, 4.9 mmol) and HONB (0.85 gm, 4.74 mmol) successively and the reaction mixture was stirred at room temperature for 35 minutes, when a suspension was observed. To this stirring mixture was added nucleoside (2.3 gm, 3.56 mmol) and the stirring was continued for 2.5 hours at room temperature, after which tire the reaction was complete, as judged by tlc (10% MeOH/$CH_2Cl_2$). The reaction mixture was diluted with EtOAc (50 ml) and washed with water (2×20 ml). The black water layer was extracted with EtOAc (20 ml) and the combined organic layer was dried over anhydrous $Na_2SO_4$ and the solvent removed under reduced pressure to give an oil which was purified by column chromatography using 5–10% MeOH/$CH_2Cl_2$ as the eluant. The appropriate fractions were collected and concentrated to give an oil which after drying under vacuum for 5 hours gave a Foam yield=2.2 gm, 60%.

Example 12

2'-O-(N-Fmoc-γ-tert.Butyl-α-L-glutamyl)-aminohexyl-5'-O-DMT-5-methyl-uridine (39)

This compound was prepared by the same method as described for compound 38. Thus from 1.3 gms (3.0 mmol) of 37, 2.3 gm (3.48 mmol) of 29, 1.0 gm (4.8 mmol)of DCC and 0.8 gm (4.4 mmol) of HONB, 2.0 gm (62%) of pure product, along with additional 1.0 gm (30%) of 85% pure product of desired conjugate was obtained.

Example 13

2'-O-(γ-tert-Butyl-α-L-glutamyl)-aminohexyl-5'-O-DMT-uridine (40)

A solution of 38 (0.5 gm, 0.47 mmol) in 0.1 M solution of DBU (15 ml) was stirred at room temperature for 1 hour. The reaction was complete as judged by tlc (10% MeOH/$CH_2Cl_2$) analysis which was followed by the removal of the solvent under reduced pressure. The residue was dissolved in $CH_2Cl_2$ (50 ml) and was washed with water (20 ml). The organic layer was concentrated and purified by flash chromatography on silicagel using 7% MeOH in $CH_2Cl_2$ as the eluant. The fractions containing the desired compound were concentrated and dried to furnish 40 as a colorless foam, yield 0.275 gm, 70%.

Example 14

2'-O-(γ-tert.Butyl-α-L-glutamyl)-aminohexyl-5'-O-DMT-5 Methyl-uridine (41)

A solution of 39 (2.4 gm, 2.25 mmol) was stirred with 0.1 M DBU (70 ml) for 1 hour. The reaction was judged complete (tlc, 10% MeOH/$CH_2Cl_2$) and was diluted with EtOAc (100 ml), washed with saturated sodium bicarbonate (2×30 ml), water (30 ml) and the organic layer concentrated and purified by column chromatography using 7%, MeOH in $CH_2Cl_2$ as the eluant. The removal of the solvent furnished the desired compound 41 as a foam, yield=1.2 gm, 60%.

Example 15

5'-O-DMT-2'-O-Aminohexyl-uridine-$N^{10}$-trifloroacetyl-γ-tert-butyl-folic Acid-α-conjugate (42)

To a suspension of $N^{10}$-TFA-ptercic acid (0.094 gm, 0.23 mmol) in anhydrous DMF (1 ml) was added DIPEA (0.062 gm, 0.48 mmol) and the suspension was agitated to form a thick slurry. To this was added PyBrOP (0.113 gm, 0.24 mmol) and the stirring was continued for an additional 30 minutes. After this time compound 40 was added to the reaction mixture and the clear solution was allowed to stir for 24 hours when the tlc analysis 10% MeOH in $CH_2Cl_2$ indicated that some starting material was still left unreacted. The stirring was continued for an additional 12 hours, $CH_3CN$ (5 ml) was added, and the reaction mixture was left at 4° C. overnight. The separated solid was removed by filtration and washed with a small volume of $CH_3CN$. The solid material was purified by column chromatography on silicagel using 10% MeOH in $CH_2Cl_2$ as the eluant. The appropriate fractions were collected and concentrated to furnish nucleoside-folic acid-α-conjugate 42 as a light cream colored solid, yield=0.07 gm, 25%, $^1$H NMR, 400 MHz (DMSO-$d_6$) δ 11.51 (bs, 1%), 11.39 (bs, 1H), 8.62 (s, 1H), 8.50 (d, 1H, J=7.2 Hz), 7.88 1,m, 3H), 7.78 (d, 1H, J=8.4 Hz), 7.62 (d, 2H, J=8.0 Hz), 7.40–7.20 (m, 9H), 6.68 (d, 4H, J=8.4 Hz), 5.80 (bs, 1H), 5.30 (d, 1H, J=8.4 Hz), 5.14–5.10 (m, 3H), 4.35–4.25 (s, 1H), 4.21–4.18 (m, 1H), 3.92–3.83 (m, 2H), 3.66 (s, 6H), 3.59–3.45 (m, 2H), 3.38–3.20 (m, 3H), 3.17–3.00 (m, 2H), 2.26–2.20 (m, 2H), 2.03–1.80 (m, 2H), 1.58–1.14 (m, 15H); $^{13}$C NMR (DMSO-$d_6$): δ 171.67, 170.82, 165.41, 162.99, 160.68, 159.11, 156.76, 155.77, 155.43, 154.01, 150.26, 149.39, 144.64, 143.98, 141.43, 140.21, 135.33, 135.05, 134.54, 129.75, 128.55, 128.09, 127.89,127.68, 126.79, 117.54, 114.67, 113.23, 101.45, 87.13, 85.87, 82.58, 80.86, 79.61, 69.81, 68.45, 62.59, 55.03, 53.80, 52.91, 31.59, 29.06, 28.98, 27.67, 26.91, 26.12, 25.10; ESMS (-ive ion): M-1, 1219.1 which agrees with $C_{61}H_{67}N_{10}O_{14}F_3$.

Example 16

5'-O-DMT-2'-O-Aminohexyl-5-methyl-uridine-$N^2$-ibu-$N^{10}$-trifloroacetyl-α-tert-butyl-folic Acid-γ-cojugate (43)

To a stirring solution of $N^2$-ibu-$N^{-10}$-trifluoroacetyl pteroic acid 27 (1.0 gms, 2.0 mmol, 70% pure by NMR) in anhydrous DMF (10 ml) and to this was added PyBrOP (1.1 gm, 2.35 mmol) and the reaction mixture was stirred at room temperature for 10 minutes. After this time, DIPEA (1.1 ml, 6.3 mmol) was added and the stirring was continued for an additional 15 minutes. Then the nucleoside-glutamic acid derivative 31 (1.8 gm, 2.13 mmol) was added and the stirring was continued overnight. The tlc analysis (10% MeOH in $CH_2Cl_2$) showed that the reaction was complete. It was diluted with EtOAc (100 ml) and washed with saturated sodium bicarbonate solution (2×30 ml), water (30 ml) and brine (30 ml). The organic layer was dried and concentrated to furnish a orange colored foam, which was purified by flash chromatography using 7% MeOH/$CH_2Cl_2$ as the eluant. The collection and the concentration of the appropriate factions gave a yellow colored foam, which still showed the presence of some impurities along with the desired compound. The further purification was achieved by chromatography using 3% MeOH in $CH_2Cl_2$ and concentrating the des red fractions to furnish 43 as a light yellow foam yield=0.85 ms 31% (48% based on 70% pure pteroic acid). $^1$H NMR 200 MHz (DMSO-$d_6$) δ 12.40 (bs, 1H), 12.00 (bs, 1H), 11.40 (bs, 1H), 8.92 (s, 1H), 8.81 (d, 1H, J=7.2 Hz), 7.94 (d, 2H, J=8.3 Hz), 7.85–7.79 (m, 2H), 7.71 (d, 2H, J=8.2 Hz), 7.52 (s, 1H), 7.43–7.25 (m, 9H), 6.94–6.89 (m, 4H), 5.86 (d, 1H, J=4.4 Hz), 5.77 (s, 2H), 4.32–4.18 (m, 2H), 4.04 (m, 2H), 3.75 (s, 6H), 3.67–3.44 (m, 2H), 3.30 (m, 2H), 3.07–2.84 (m, 2H), 2.89–2.72 (m, 1H), 2.30–1.85 (M, 4H), 1.50–1.13 (m, 26H); high resolution FAB MS (MH$^+$) m/e 1305.5389 ($C_{66}H_{76}N_{10}O_{13}F_3$) requires, 1305.5444; (MNa+) 1328.00.

Example 17

5'-O-DMT-2'-O-Aminohexyl-5-methyl-uridine-$N^2$-ibu-$N^{10}$-trifloroacetyl-α-tert-butyl-folic Acid-γ-conjugate 3'-Phosphoramidite (44)

To a solution of nuclecside-folic acid conjugate 43 (0.50 gm, 0.38 mmol, 90% pure) n anhydrous $CH_2Cl_2$ (5 ml) was added DIPEA (0.2 ml, 1.14 mmol) and the solution was stirred for 5 minutes. To this was then added 2-cyanoethyl N,N-diisopropyl chlorophosphoramidite (0.136 gm, 0.57 mmol) and the reaction mixture was stirred at room temperature for 1 hour when the reaction was complete. The reaction mixture was diluted with $CH_2Cl_2$ (50 ml), washed with saturated bicarbonate solution (2×30 ml) and brine (30 ml). The organic layer was dried over anhydrous $Na_2SO_4$ and the solvent removed under reduced pressure. The residue was purified by column chromatography, first eluting the column with a mixture of 60:33:7 (EtOAc:hexane:MeOH) allowed by 10% MeOH in $CH_2Cl_2$. The appropriate fractions were collected and concentrated to furnish the desired phosphoramidite as light yellow foam, yield=0.375 gm, 66%; $^{31}$P NMR (CD$_3$CN): δ 151.01, 150.80 ppm, high resolution FAB MS (M+Cs$^+$) m/e 1637.5624 ($C_{75}H_{92}N_{12}O_{16}CsPF_3$) requires 1637.5498.

Example 18

5'-O-DMT-2'-O-Aminohexyl-5-methyl-uridine-$N^2$-ibu-$N^{10}$-trifloroacetyl-γ-tert-butyl-folic Acid-α-conjugate (45)

This compound was prepared using the same procedure as described for compound 43. Thus form 0.93 gms (1.94 mmol of pteroic acid analog, less than 70% pure), PyBrOP (1.08 gm, 2.31 mmol), DIPEA (1.2 ml, 6.8 mmol) and nucleoside-L-glutamic acid α-conjugate 41 (1.7 gms, 2.00 mmol) in anhydrous DMF (10 ml). After the overnight reaction, and the workup and chromatography, the product 45 was obtained at 80% purity, yield=0.40 gms, 16%, high resolution FAB MS (MH$^+$) m/e 1305.5386 ($C_{66}H_{76}N_{10}O_{15}F_3$) requires, 1305.5444. This compound was used in the next step without further purification.

Example 19

5'-O-DMT-2'-O-Aminohexyl-uridine-$N^2$-ibu-$N^{10}$-trifloroacetyl-γ-tert-butyl-folic Acid-α-conjugate 3'-Phosphoramidite (46)

To a stirring solution of compound 45 (0.40 gm, 0.30 mmol) and DIPEA (0.123 gm, 0.95 mmol) in anhydrous $CH_2Cl_2$ was added 2-cyanoethyl N,N-diisopropyl chlorophosphoramidite (0.117 gm, 0.5 mmol) slowly over 5 minutes and the reaction mixture was stirred under argon atmosphere at room temperature for 1.5 hour. The tlc system (60:33:7, EtOAc:hexane:MeOH) indicated the completion of the reaction. The fluorescent impurity in the starting material did not get phosphoryated. The reaction mixture was diluted with $CH_2Cl_2$ (50 ml), washed with saturated sodium bicarbonate solution (2×20 ml), brine (20 ml) and the organic layer dried over $Na_2SO_4$ and the solvent removed under reduced pressure to give a residue which was purified by column chromatography on silicagel using 10–15% MeOH in a 60:30 mixture of EtOAc:hexane as the eluant. The fractions containing the product was concentrated to furnish 46 as a foam, yield=0.343 gm, 74% (25% of the fluorescent non-phosphorus impurity was still present), $^{31}$P NMR ($CD_3CN$) δ 150.99, 150.77; high resolution FAB MS (M+Cs) m/e 1637.5632 ($C_{75}H_{92}N_{12}O_{16}CsPF_3$) requires 1637.5498.

Example 20

2'-O-(N-Fmoc-α-Allyl-γ-L-glutamyl)-aminohexyl-5-O-DMT-5-methyl-uridine (48)

To a solution of N-Fmoc protected-α-allyl-L-glutamic acid 47 (2.0 gm, 4.8 mmol) in anhydrous DMF (12 ml) was added DCC (1.51 gm, 7.31 mmol) and HONB (1.31 gm, 7.31 mmol) successively and the reaction mixture was stirred for 15 minutes, when 2'-O-hexylamino-5'-O-DMT-5-methyl-uridine 30 (3.91 gm, 5.92 mmol) was added and the reaction was allowed to stir overnight. It was diluted with EtOAc (100 ml) and washed with water (3×20 ml), organic layer dried over anhydrous $Na_2SO_4$ and concentrated. The residue was purified on silicagel using 3% MeOH/$CH_2Cl_2$ as the eluant. The appropriate fractions were collected and concentrated to furnish 48 as a colorless foam, yield=3.30 gm, 64%, $^1$H NMR (DMSO-$d_6$) d 11.40 (bs, 1H), 7.92–7.71(m, 5), 7.51–7.25 (m, 13H), 6.93–6.88 (m, 4H), 5.90–5.80 (m, 2H), 5.61–5.53 (m, 1H), 5.39–5.15 (m, 3H), 4.58 (bs, 2H), 4.30–3.95 (m, 7H), 3.74 (s, 6H), 3.62–3.00 (m, 8H), 2.18–1.12 (m, 1H).

Example 21

2'-O-(α-Allyl-γ-L-glutamyl)-aminohexyl-5'-O-DMT-5 Methyl-uridine (49)

A solution of compound 48 (2.0 gm, 1.9 mmol) was stirred in 10% piperidine in $CH_3CN$ (20 ml) for 30 minutes when the tlc system (10% MeOH/$CH_2Cl_2$) indicated the reaction was complete. The solvent was removed and the residue was purified on silicagel by flash chromatography method using 7% MeOH in $CH_2Cl_2$. The fractions were collected and concentrated to give the desired compound as a colorless foam, yield=1.5 gms, 95%.

Example 22

5'-O-DMT-2'-O-Aminohexyl-5-methyl-uridine-$N^2$-ibu-$N^{10}$-trifloroacetyl-α-allyl-folic Acid-γ-conjugate (50)

A solution of 27 (0.80 gm, 1.67 mmol) in anhydrous DMF (5 ml) was stirred and to tis was added DIPEA (0.50 ml, 2.90 mmol) and the stirring was continued for 5 minutes. After this time, PyBrOP (0.77 gm, 1.66 mmol) was added and the reaction mixture stirred for an additional 15 minutes followed by the addition of nucleoside-amino acid conjugate 49 (1.2 gm, 1.45 mmol) and the stirring was continued overnight at room temperature. It was diluted with EtOAc (100 ml) and then washed with saturated sodium bicarbonate (2×20 ml) followed by brine (2×23 ml). The organic layer dried over anhydrous $Na_2SO_4$ and concentrated. The residual solid was purified by column chromatography using 10% MeOH in EtOAc and the fractions containing the major compound were combined and concentrated. It was repurified using 5% MeOH in $CH_2Cl_2$, The fractions which were relatively clean were combined and concentrated to furnish compound 50 as a light yellow foam. Yield=0.584 gm, 27%+0.156 gm, 7% about 85% pure compound by NMR. $^1$H NMR (CDCl$_3$): δ 12.56 (bs, 1H), 10.93 (bs, 1H), 10.20 (bs, 8), 8.89 (s, 1H), 8.40–8.37 (m, 1H), 7.93 (d, 2H, J=8.4 Hz), 7.69 (s, 1H), 7.32–7.22 (m, 11H), 6.8 (d, 4H, J=8.6 Hz), 6.37–6.32 (m, 1H), 6.03 (d, 1H, J=3.3 Hz), 6.00–5.80 (m, 1H), 5.34–5.20 (m, 4H), 4.64–4.40 (m, 4H), 4.10–3.98 (m, 2H), 3.78–3.32 (m, 13H), 2.7–1.23 (m, 17H); ESMS (-ive ion) m/e 1288.3) which is in agreement with $C_{65}H_{70}N_{10}O_{15}F_3$.

Example 23

5'-O-DMT-2'-O-Aminohexyl-5-methyl-uridine-$N^2$-ibu-$N^{10}$-trifloroacetyl-α-allyl-folic Acid-γ-cojugate 3'-Phosphoramidite (51)

To a solution of compound 50 (0.25 gm, 0.19 mmol), DIPEA (0.057 gm, 0.44 mmol), in anhydrous $CH_2Cl_2$ (3 ml) was added chlorophosphitylating agent (0.071 gm, 0.31 mmol) and the reaction mixture was stirred for 1.5 hours when tlc (10% MeOH) indicated the reaction was incomplete. 10% more phosphityiating reagent was added and the reaction was allowed to stir for an additional 3 hours. The reaction mixture was diluted with $CH_2Cl_2$ (50 ml) and washed with saturated sodium bicarbonate (2×20 ml), brine (20 ml and dried over anhydrous $Na_2SO_4$. The solvent was removed and the compound purified by 5% MeOH in $CH_2Cl_2$. The fractions containing the amidite were concentrated to give a foam yield, 0.110 gm, 39%. $^{31}$P NMR ($CD_3CN$): δ 151.01 and 150.81.

Example 24

Folic Acid Derivatized Oligonucleotides Oligonucleotide Synthesis.

The oligonucleotide synthesis was performed on an ABI 380B DNA Synthesizer. A solid support bound 19-mer DMT-GCATC$_5$AG$_2$C$_2$AC$_2$AT was assembled using standard reagents, cycles, and procedures, phosphoramidite chemistry, and either commercial oxidizer or 3H-1,2- benzodithiol-3-one 1,1-dioxide (0.05 M in MeCN) as the sulfur-transfer reagent. If introduction of 2 was planned, DMT $C^{tBPA}$ 2-cyanoethyl phosphoramidite was used for the chain assembly. Phosphoramidite building blocks 1–4 were employed on the last coupling step. For their attachment, 5-methylthio-1H-tetrazole was used as an activator, and the coupling time was extended to 10 minUTES. Phosphoramidites 1–2, 4 were used as 0.1 M solutions in MeCN. For 3, solution in DMF (0.05 M) was employed. Following the coupling of 2, the oxidation step was performed with the aid of t-butyl hydroperoxide reagent (10% in MeCN; 10 min). In all cases except for 3 good coupling yield was observed. Synthesized oligonucleotides are listed in Table 1.

Table 1

Oligonucleotides Synthesized with the Aid of 1–2, 4

| Amidite | Backbone | Solid support bound oligo-nucleotide | Deprotected oligo-nucleotide | ES MS, MW Found | Calculated |
|---|---|---|---|---|---|
| 1 | P = S | 5 | 8 | 6880.53[a] | 6882.72[a] |
| 2 | P = O | 6 | 9 | 6218.3 | 6219.0 |
| 4 | P = S | 7 | 10 | 6880.65[a] | 6882.72[a] |

[a]tBu ester.

Deprotection of Oligonucleotides 5,7.

Solid support bound oligonucleotides 5,7 were treated with conc. aq. ammonia for h hour at room temperature. The solid support was removed, and the solution was kept at 50° C. for 8 hours. The deprotection mixture was evaporated to dryness, dissolved in water, and separated by HPLC.

Deprotection of Oligonucleotide 6.

A mixture of tetrakis(triphenylphosphine)palladium(0) (20 mg), triphenylphosphine (45 mg) and n-butylammonium formate (1.2 M in THF; upper phase; 1.0 mL) was shaken to obtain homogeneous solution and added to a solid support bound oligonucleotide 6. The reaction mixture was shaken at 50° C. for 1.5 hours, liquid phase was withdrawn, and solid support was washed with THF (5×1 mL). An aqueous sodium N,N-diethyldithiocarbamate (0.1 M; 1.0 mL) was added, the suspension was shaken for 1 minutes, the liquid was withdrawn, and the solid support was washed with water (5×1 mL). Fresh portion of sodium N,N-diethyldithiocarbamate (0.1 M; 1.0 mL) was added, and the washing cycle was repeated. Finally, the solid support was washed with THF (3×1 mL) suspended in 40% aq methylamine (1.5 mL) and was kept at room temperature for 4 hours with occasional shaking. The liquid was collected, and the solid was washed with water (3×0.5 mL). The combined solutions were evaporated to dryness, the residue was dissolved in water (2 mL) and separated by HPLC.

Deprotection and Isolation of Oligonucleotide Conjugates.

Crude oligonucleotides were applied on a DeltaPak 15 C18 300 HPLC column (3.8×300 mm,) eluted with a linear gradient from 0 to 60% B in 60 min :0.1 M aq NE OAc as buffer A, 80% aq MeCN as buffer B). A major peak was collected, detritylated with 80% aq AcOH for 15 minutes, re-purified on the same column, and desalted. The oligonucleotides 8–10 were characterized by ES MS (Table 1).

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula XIIIA, XIIIB, XIIIC or XIIID:

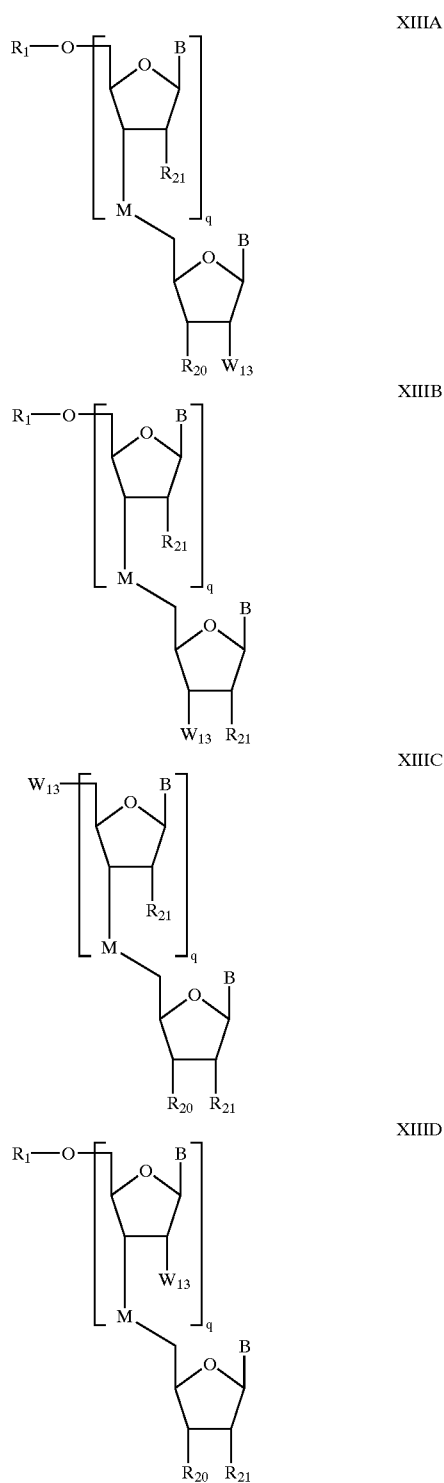

wherein:

$W_{13}$ has the Formula:

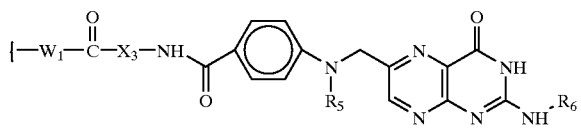

$R_1$ is H or a hydroxyl protecting group;

B is a nucleobase;

each $R_{21}$ is H, OH, F, or a group of formula Z—$R_{22}$—$(R_{23})_v$;

Z is O, S, NH or N—$R_{22}$—$(R_{23})_v$;

$R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_{21}$ has one of the formulas:

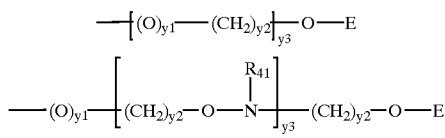

wherein:
y1 is 0 or 1;
y2 is 0 to 10;
y3 is 1 to 10;
E is $N(R_{41})(R_{42})$ or $N=C(R_{41})(R_{42})$;
each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;

v is from 0 to about 10;

q is 0 to about 50, provided that when said compound has formula XIIID, q is at least 1;

M is an optionally protected internucleoside linkage;

$W_1$ is —O—$(CH_2)_n$—NH— where n is from 1 to about 10;

$R_{20}$ is OH or a group of Formula:

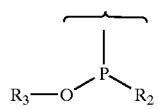

$R_2$ is —$N(R_7)_2$, or a heterocycloalkyl or heterocycloalkenyl ring containing from 4 to 7 atoms, and having up to 3 heteroatoms selected from nitrogen, sulfur, and oxygen;

$R_7$ is straight or branched chain alkyl having from 1 to 10 carbons;

$R_3$ is a phosphorus protecting group;

$R_5$ is H or an amino protecting group;

$R_6$ is H or an amino protecting group;

$X_3$ is —$CH(Z_1)$— or a group of Formula XI:

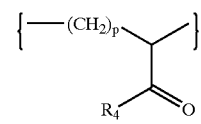

$Z_1$ is the sidechain of a naturally occurring amino acid, or a protected sidechain of a naturally occurring amino acid;

p is 1 or 2; and $R_4$ is a hydroxyl group, or a protected hydroxyl group.

2. The compound of claim 1 wherein n is 6.

3. The compound of claim 1 wherein $X_5$ has the Formula XI.

4. The compound of claim 3 wherein p is 2.

5. The compound of claim 4 wherein $W_1$ is —O—$(CH_2)_6$—NH—.

6. The compound of claim 5 wherein $R_4$ is t-butoxy.

7. The compound of claim 6 wherein $R_1$ is dimethoxytrityl, $R_5$ is trifluoroacetoyl, and $R_6$ is —C(=O)—CH(CH_3)_2.

8. The compound of claim 7 wherein q is 0.

9. The compound of claim 8 wherein $R_{20}$ is a group of Formula:

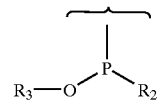

where $R_3$ is β-cyanoethyl, and $R_2$ is diisopropylamino.

10. A composition comprising a compound of claim 4, said composition being substantially free of a compound of Formula XIVA, XIVB, XIVC, or XIVD:

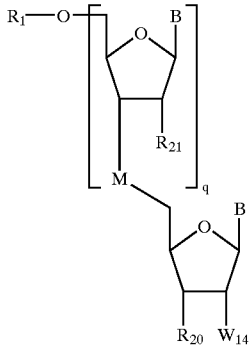

XIVA

-continued
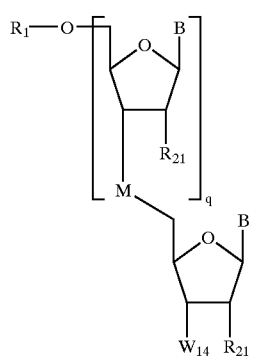
XIVB
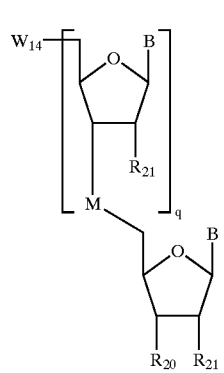
XIVC
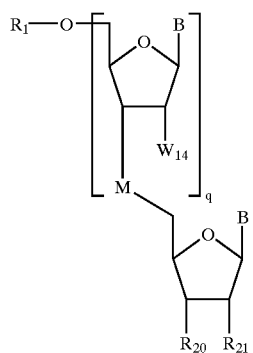
XIVD
wherein:
$W_{14}$ has the Formula:
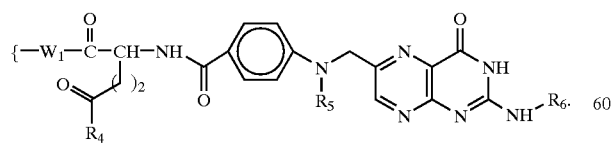
11. The compound of claim 7 wherein $R_{20}$ is H.
12. The compound of claim 11 wherein q is 0.
13. A compound having the Formula XIIIA, XIIIB, XIIIC or XIIID:
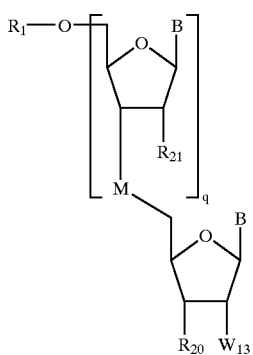
XIIIA
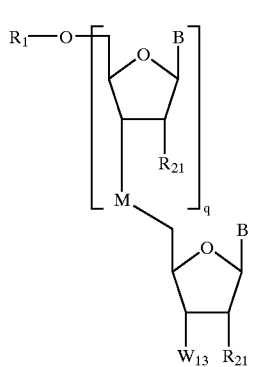
XIIIB
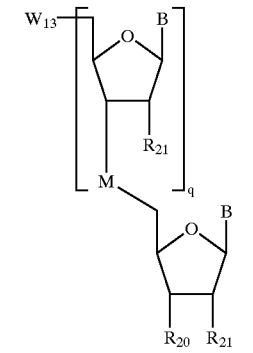
XIIIC
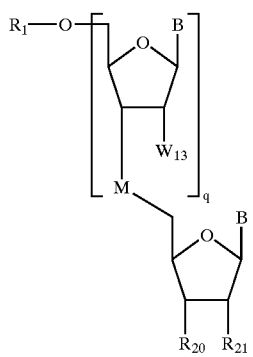
XIIID wherein:

$W_{13}$ has the Formula:

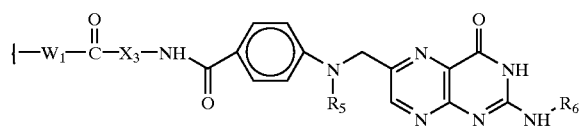

$R_1$ is dimethoxytrityl;

B is a nucleobase;

each $R_{21}$ is H, OH, F, or a group of formula $Z—R_{22}—(R_{23})_v$;
  Z is O, S, NH or $N—R_{22}—(R_{23})_v$;
  $R_{22}$ is $C_1–C_{20}$ alkyl, $C_2–C_{20}$ alkenyl, or $C_2–C_{20}$ alkynyl;
  $R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
  or $R_{21}$ has one of the formulas:

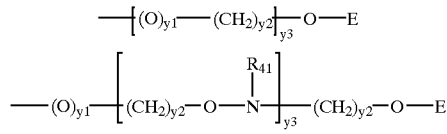

wherein:
  y1 is 0 or 1;
  y2 is 0 to 10;
  y3 is 1 to 10;
  E is $N(R_{41})(R_{42})$ or $N=C(R_{41})(R_{42})$;
  each $R_{41}$ and each $R_{42}$ is independently H, $C_1–C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;
  v is from 0 to about 10;

q is 0 to about 50, provided that when said compound has formula XIIID, q is at least 1;

M is an optionally protected internucleoside linkage;

$W_1$ is a linking group, O, NH or S;

$R_{20}$ is OH or a group of Formula:

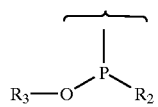

$R_2$ is $—N(R_7)_2$, or a heterocycloalkyl or heterocycloalkenyl ring containing from 4 to 7 atoms, and having up to 3 heteroatoms selected from nitrogen, sulfur, and oxygen;
$R_7$ is straight or branched chain alkyl having from 1 to 10 carbons;

$R_3$ is a phosphorus protecting group;
$R_5$ is trifluoroacetoyl;
$R_6$ is $—C(=O)—CH(CH_3)_2$;
$X_3$ is $—CH(Z_1)—$ or a group of Formula XI:

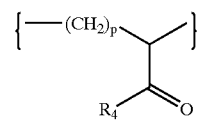

XI $Z_1$ is the sidechain of a naturally occurring amino acid, or a protected sidechain of a naturally occurring amino acid;
p is 1 or 2; and
$R_4$ is t-butoxy.

14. A compound having the Formula XIIIA, XIIIB, XIIIC or XIIID:

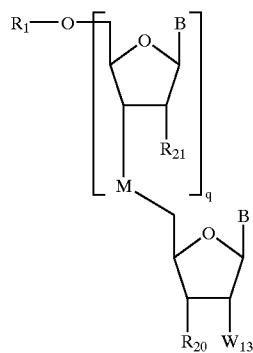

XIIIA

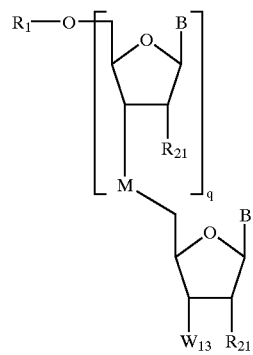

XIIIB

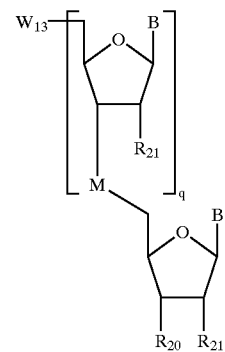

XIIIC

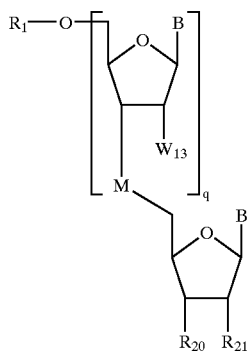

wherein:
W$_{13}$ has the Formula:

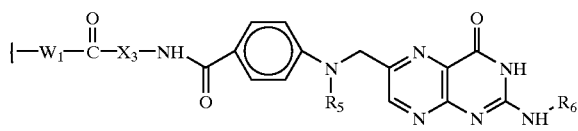

R$_1$ is H or a hydroxyl protecting group;
B is a nucleobase;
each R$_{21}$ is H, OH, F, or a group of formula Z—R$_{22}$—(R$_{23}$)$_v$;
Z is O, S, NH or N—R$_{22}$—(R$_{23}$);
R$_{22}$ is C$_1$–C$_{20}$ alkyl, C$_2$–C$_{20}$ alkenyl, or C$_2$–C$_{20}$ alkynyl;
R$_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
or R$_{21}$ has one of the formulas:

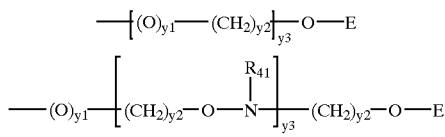

wherein:
y1 is 0 or 1;
y2 is 0 to 10;
y3 is 1 to 10;
E is N(R$_{41}$)(R$_{42}$) or N═C(R$_{41}$)(R$_{42}$);
each R$_{41}$ and each R$_{42}$ is independently H, C$_1$–C$_{10}$ alkyl, a nitrogen protecting group, or R$_{41}$ and R$_{42}$ taken together form a nitrogen protecting group; or R$_{41}$ and R$_{42}$ taken together with the N or C atom to which they are attached form a ring structure that can include at least one heteroatom selected from N and O;

v is from 0 to about 10;
q is 0 to about 50, provided that when said compound has formula XIIID, q is at least 1;
M is an optionally protected internucleoside linkage;
W$_1$ is a linking group, O, NH or S;
R$_{20}$ is a group of Formula:

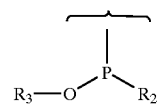

where R$_3$ is β-cyanoethyl, and R$_2$ is diisopropylamino;
R$_2$ is —N(R$_7$)$_2$, or a heterocycloalkyl or heterocycloalkenyl ring containing from 4 to 7 atoms, and having up to 3 heteroatoms selected from nitrogen, sulfur, and oxygen;
R$_7$ is straight or branched chain alkyl having from 1 to 10 carbons;
R$_3$ is a phosphorus protecting group;
R$_5$ is H or an amino protecting group;
R$_6$ is H or an amino protecting group;
X$_3$ is —CH(Z$_1$)— or a group of Formula XI:

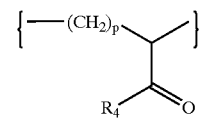

Z$_1$ is the sidechain of a naturally occurring amino acid, or a protected sidechain of a naturally occurring amino acid;
p is 1 or 2; and
R$_4$ is a hydroxyl group, or a protected hydroxyl group.

15. The compound of claim 14 wherein W$_1$ is —O—(CH$_2$)$_6$—NH—, R$_1$ is dimethoxytrityl, R$_5$ is trifluoroacetoyl, R$_6$ is —C(═O)—CH(CH$_3$)$_2$, and R$_4$ is t-butoxy.

16. The compound of claim 14, wherein said compound has the formula XIIIA, XIIIB or XIIIC and wherein q is 0.

17. A compound having the Formula XIIIA, XIIIB, XIIIC or XIIID:

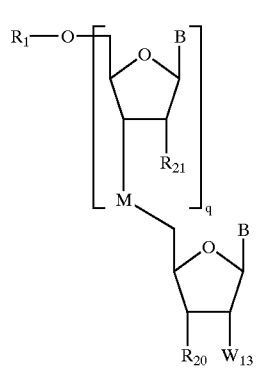

-continued

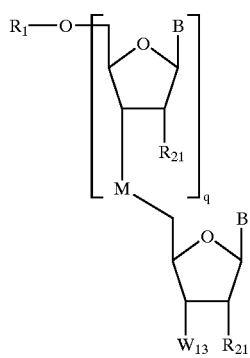

XIIIB

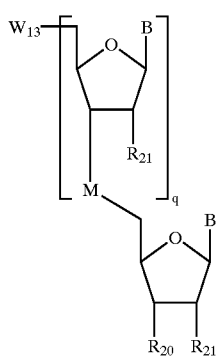

XIIIC

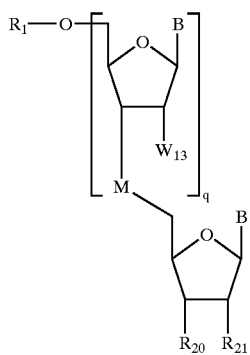

XIIID wherein:
$W_{13}$ has the Formula:

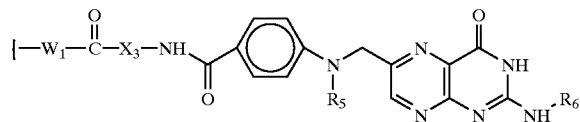

$R_1$ is H or a hydroxyl protecting group;
B is a nucleobase;
each $R_{21}$ is H, OH, F, or a group of formula $Z-R_{22}-(R_{23})_v$;
Z is O, S, NH or $N-R_{22}-(R_{23})_v$;
$R_{22}$ is $C_1-C_{20}$ alkyl, $C_2-C_{20}$ alkenyl, or $C_2-C_{20}$ alkynyl;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
or $R_{21}$ has one of the formulas:

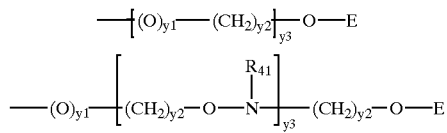

wherein:
y1 is 0 or 1;
y2 is 0 to 10;
y3 is 1 to 10;
E is $N(R_{41})(R_{42})$ or $N=C(R_{41})(R_{42})$;
each $R_{41}$ and each $R_{42}$ is independently H, $C_1-C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;
v is from 0 to about 10;
q is 0 to about 50, provided that when said compound has formula XIIID, q is at least 1;
M is an optionally protected internucleoside linkage;
$W_1$ is a linking group, O, NH or S;
$R_{20}$ is OH or a group of Formula:

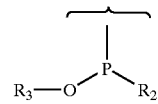

$R_2$ is $-N(R_7)_2$, or a heterocycloalkyl or heterocycloalkenyl ring containing from 4 to 7 atoms, and having up to 3 heteroatoms selected from nitrogen, sulfur, and oxygen;
$R_7$ is straight or branched chain alkyl having from 1 to 10 carbons;
$R_3$ is a phosphorus protecting group;
$R_5$ is H or an amino protecting group;
$R_6$ is H or an amino protecting group;
$X_3$ is a group of Formula XI:

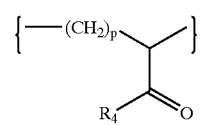

XI $Z_1$ is the sidechain of a naturally occurring amino acid, or a protected sidechain of a naturally occurring amino acid;
p is 1 or 2; and
$R_4$ is a hydroxyl group, or a protected hydroxyl group.
18. The method of claim 17 further comprising contacting said compound of Formula VIIA or VIID with a phosphitylating reagent to form a compound of Formula VIIIA or VIIID:

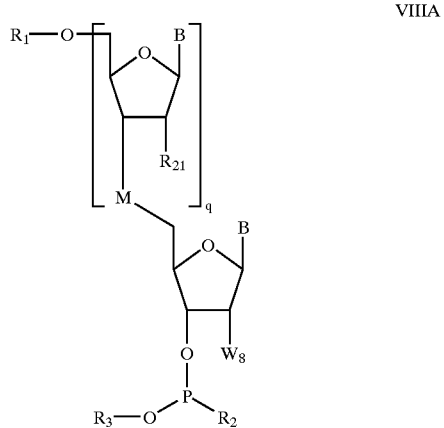

VIIIA

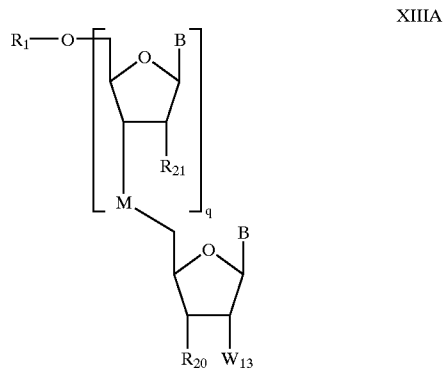

XIIIA

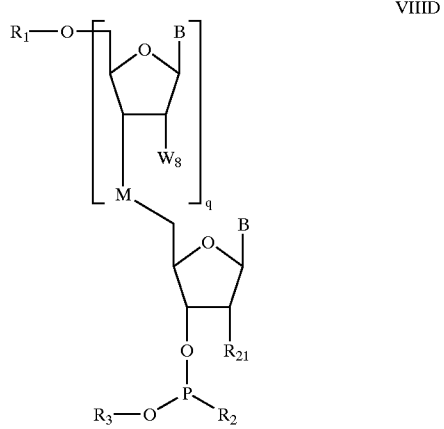

VIIID

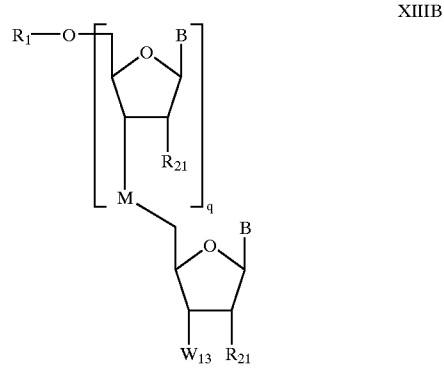

XIIIB wherein:

$R_2$ is —$N(R_7)_2$, or a heterocloalkyl or heterocycloalkenyl ring containing from 4 to 7 atoms, and having up to 3 heteroatoms selected from nitrogen, sulfur, and oxygen;

$R_7$ is a straight or ranched chain alkyl having from 1 to 10 carbon atoms;

$R_3$ is a phosphorus protecting group; and $W_8$ has the Formula:

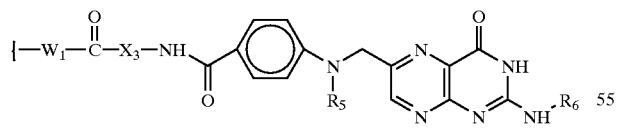

provided that when said compound has formula VIIID, q is at least 1.

19. The method of claim 10 wherein $X_3$ has the formula XI.

20. The method of claim 19 wherein $R_1$ is dimethoxytrityl, $W_1$ has the formula —O—$(CH_2)_n$—NH— where n is 6, p is 2, $R_4$ is t-butoxy, $R_5$ is trifluoroacetoyl, $R_6$ is —C(=O)—$CH(CH_3)_2$, and $R_{30}$ is FMOX.

21. A compound having the Formula XIIIA, XIIIB, XIIIC or XIIID:

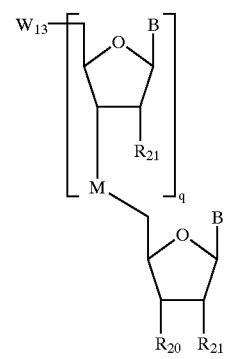

XIIIC

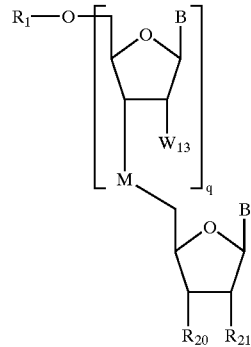

XIIID wherein:

$W_{13}$ has the Formula:

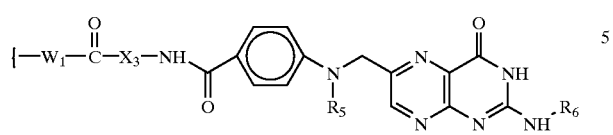

$R_1$ is H or a hydroxyl protecting group;

B is a nucleobase;

each $R_{21}$ is H, OH, F, or a group of formula $Z—R_{22}—(R_{23})_v$;

$Z$ is O, S, NH or $N—R_{22}—(R_{23})_v$;

$R_{22}$ is $C_1–C_{20}$ alkyl, $C_2–C_{20}$ alkenyl, or $C_2–C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_{21}$ has one of the formulas:

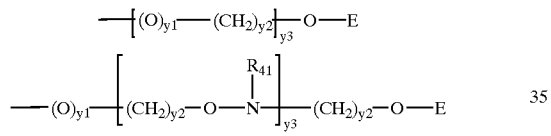

wherein:

y1 is 0 or 1;

y2 is 0 to 10;

y3 is 1 to 10;

E is $N(R_{41})(R_{42})$ or $N=C(R_{41})(R_{42})$;

each $R_{41}$ and each $R_{42}$ is independently H, $C_1–C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;

v is from 0 to about 10;

q is 0 to about 50, provided that when said compound has formula XIIID, q is at least 1;

M is an optionally protected internucleoside linkage;

$W_1$ is a linking group, O, NH or S;

$R_{20}$ is OH;

$R_2$ is $—N(R_7)_2$, or a heterocycloalkyl or heterocycloalkenyl ring containing from 4 to 7 atoms, and having up to 3 heteroatoms selected from nitrogen, sulfur, and oxygen;

$R_7$ is straight or branched chain alkyl having from 1 to 10 carbons;

$R_3$ is a phosphorus protecting group;

$R_5$ is H or an amino protecting group;

$R_6$ is H or an amino protecting group;

$X_3$ is $—CH(Z_1)—$ or a group of Formula XI:

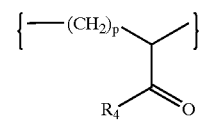

$Z_1$ is the sidechain of a naturally occurring amino acid, or a protected sidechain of a naturally occurring amino acid;

p is 1 or 2; and $R_4$ is a hydroxyl group, or a protected hydroxyl group.

22. The compound of claim 21 wherein q is 0.

23. A synthetic method comprising the steps of:

(a) providing a compound of Formula IA, IB, IC or ID:

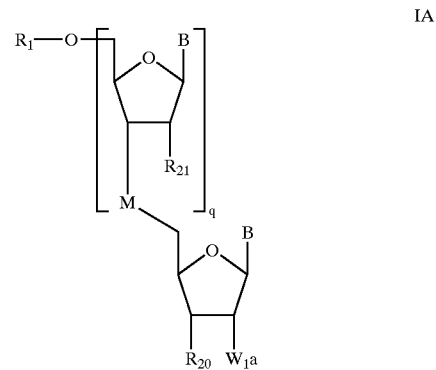

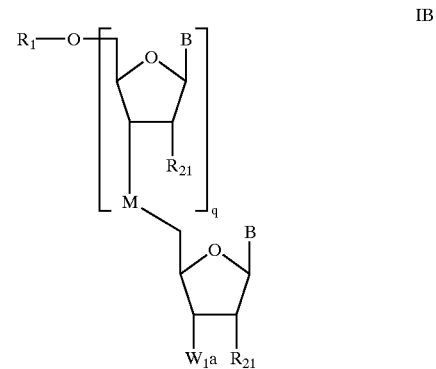

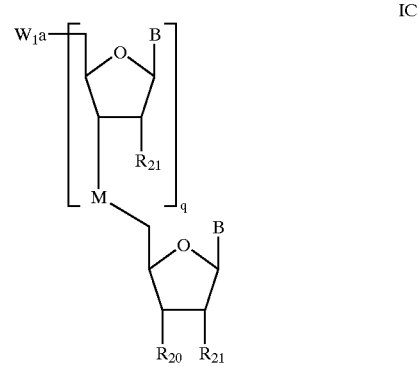

-continued

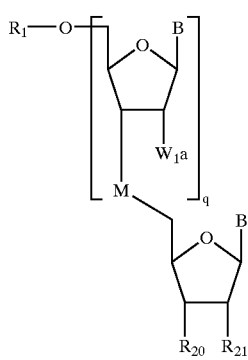

ID wherein:
W$_{1a}$ is W$_{1b}$—H, OH, NH$_2$ or SH where W$_{1b}$ is a linking group;
R$_1$ is H or a hydroxyl protecting group;
B is a nucleobase;
R$_{20}$ is a group of Formula:

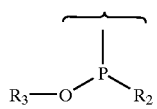

each R$_{21}$ is H, OH, F, or a group of formula Z—R$_{22}$—(R$_{23}$)$_v$;
Z is O, S, NH, or N—R$_{22}$—(R$_{23}$)$_v$;
R$_{22}$ is C$_1$–C$_{20}$ alkyl, C$_2$–C$_{20}$ alkenyl, or C$_2$–C$_{20}$ alkynyl;
R$_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
v is from 0 to about 10;
or R$_{21}$ has one of the formulas:

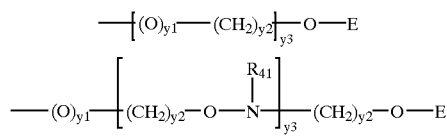

wherein:
y1 is 0 or 1;
y2 is 0 to 10;
y3 is 1 to 10;
E is N(R$_{41}$)(R$_{42}$) or N=C(R$_{41}$)(R$_{42}$);
each R$_{41}$ and each R$_{42}$ is independently H, C$_1$–C$_{10}$ alkyl, a nitrogen protecting group, or R$_{41}$ and R$_{42}$ taken together form a nitrogen protecting group; or R$_{41}$ and R$_{42}$ taken together with the N or C atom to which they are attached form a ring structure that can include at least one heteroatom selected from N and O;

q is 0 to about 50, provided that when said compound has formula ID, q is at least 1;
M is an optionally protected internucleoside linkage;

(b) reacting said compound of Formula I with a compound of Formula II:

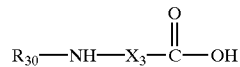

wherein:

R$_{30}$ is an amino protecting group;
X$_3$ is —CH(Z$_1$)— or a group of Formula XI:

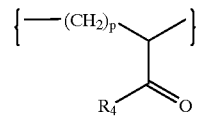

XI

Z$_1$ is the sidechain of a naturally occurring amino acid, or a protected sidechain of a naturally occurring amino acid;
R$_4$ is a hydroxyl group, or a protected hydroxyl group;
p is 1 or 2;

to form a compound of Formula IVA, IVB, IVC, or IVD:

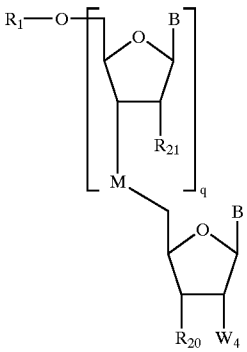

IVA

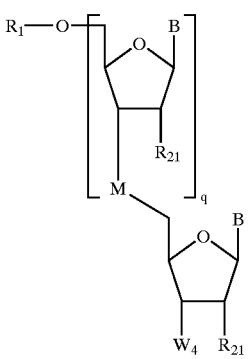

IVB

IVC
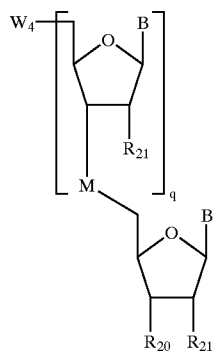
IVD
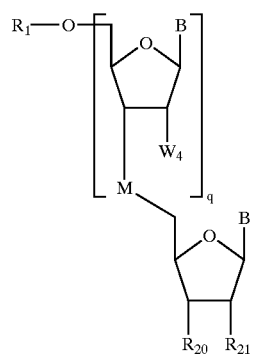
wherein:
W₄ has the formula:
{ —W₁—C(=O)—X₃—N(H)—R₃₀
where W₁ is a linking group, O, NH, or S; and
treating said compound of Formula IVA, IVB, IVC or IVD with a deprotecting reagent to form a compound of Formula VA, VB, VC or VD:
VA
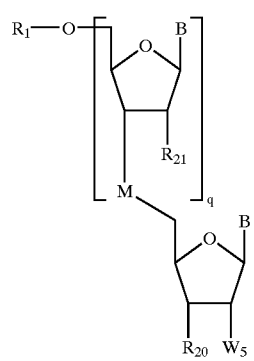
VB
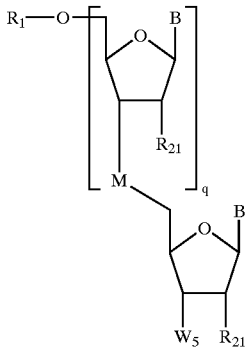
VC
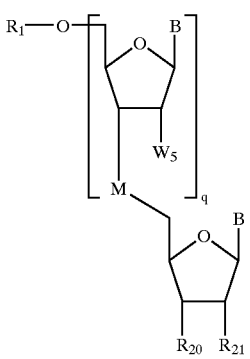
VD
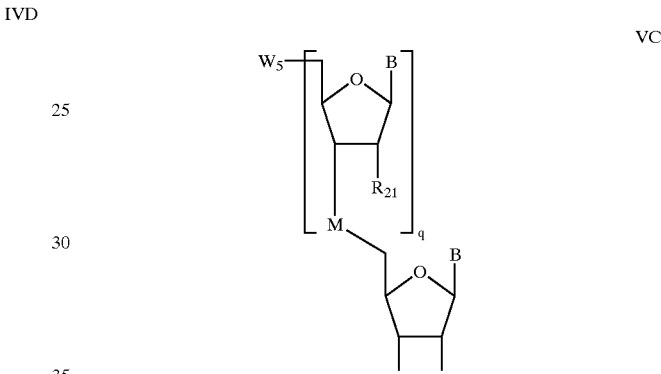
where W₅ has the Formula:
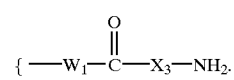
{ —W₁—C(=O)—X₃—NH₂.
24. A compound having the Formula XVIA, XVIB, XVIC or XVID:

XVIA 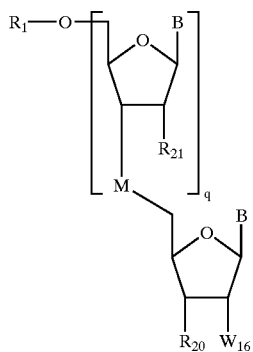

XVIB 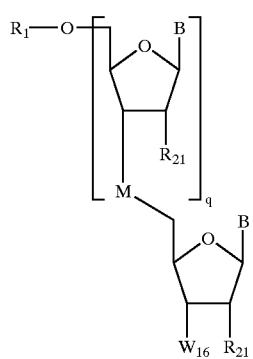

XVIC 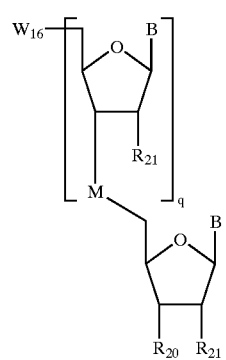

XVID 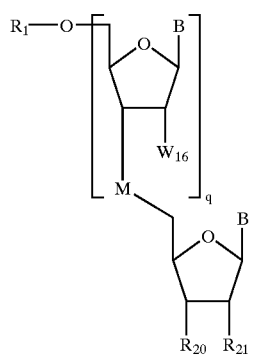

wherein:

$W_{16}$ has the Formula:

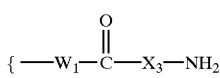

$R_1$ is H or a hydroxyl protecting group;
B is a nucleobase;
each $R_{21}$ is H, OH, F, or a group of formula $Z-R_{22}-(R_{23})_v$;
Z is O, S, NH or $N-R_{22}-(R_{23})_v$;
$R_{22}$ is $C_1-C_{20}$ alkyl, $C_2-C_{20}$ alkenyl, $C_2-C_{20}$ alkynyl, $C_1-C_{20}$ akoxy, $C_2-C_{20}$ alkenyloxy, or $C_2-C_{20}$ alkynyloxy;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkyene glycol, or polyether; or $R_{21}$ has one of the formulas:

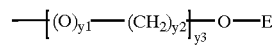

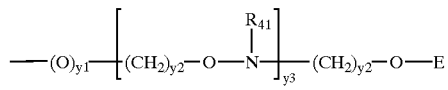

wherein:
y1 is 0 or 1;
y2 is 0 to 10;
y3 is 1 to 10;
E is $N(R_{41})(R_{42})$ or $N=C(R_{41})(R_{42})$;
each $R_{41}$ and each $R_{42}$ is independently H, $C_1-C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;
v is from 0 to about 10;
q is 0 to about 50 provided that when said compound has formula XVID, q is at least 1;
M is an optionally protected internucleoside linkage;
$W_1$ is a linking group;
$R_{20}$ is OH or a group of Formula:

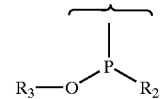

$R_2$ is $-N(R_7)_2$, or a heterocycloalkyl or heterocycloalkenyl ring containing from 4 to 7 atoms, and having up to 3 heteroatoms selected from nitrogen, sulfur, and oxygen;
$R_7$ is straight or branched chain alkyl having from 1 to 10 carbons;
$R_3$ is a phosphorus protecting group;
$X_3$ is $-CH(Z_1)-$ or a group of Formula XI:

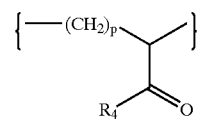

XI $Z_1$ is the sidechain of a naturally occurring amino acid, or a protected sidechain of a naturally occurring amino acid; and p is 1 or 2.

25. The compound of claim 24 wherein $X_3$ has the Formula XI.

26. The compound of claim 25 wherein p is 2.

27. The compound of claim 26 wherein $W_1$ is —O—$(CH_2)_n$—NH— where n is from 1 to about 10.

28. The compound of claim 27 wherein n is 6.

29. A compound having the Formula XVIIA, XVIIB, XVIIC or XVIID:

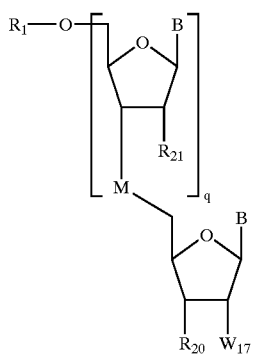

XVIIA

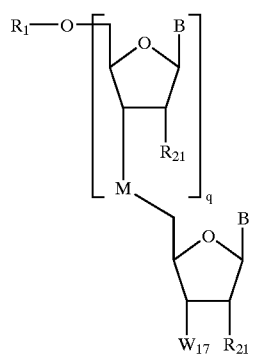

XVIIB

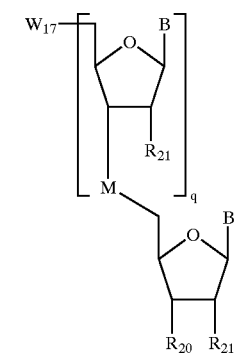

XVIIC

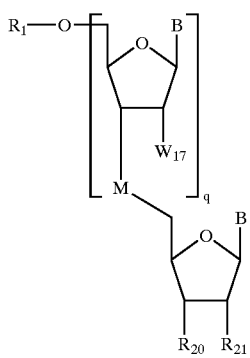

XVIID wherein:

$W_{17}$ has the Formula:

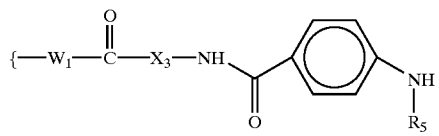

$R_1$ is H or a hydroxyl protecting group;

B is a nucleobase;

each $R_{21}$ is H, OH, F, or a group of formula Z—$R_{22}$—$(R_{23})_v$;

Z is O, S, NH or N—$R_{22}$—$(R_{23})_v$;

$R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_{21}$ has one of the formulas:

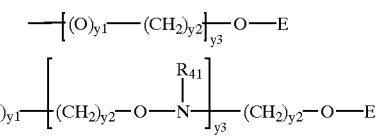

wherein:

y1 is 0 or 1;

y2 is 0 to 10;

y3 is 1 to 10;

E is $N(R_{41})(R_{42})$ or $N=C(R_{41})(R_{42})$;

each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;

v is from 0 to about 10;

q is 0 to about 50, provided that when said compound has formula XVIID, q is at least 1;

M is an optionally protected internucleoside linkage;

$W_1$ is a linking group, O, NH or S;

$R_{20}$ is OH or a group of Formula:

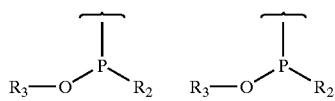

$R_2$ is —N($R_7$)$_2$, or a heterocycloalkyl or heterocycloalkenyl ring containing from 4 to 7 atoms, and having up to 3 heteroatoms selected from nitrogen, sulfur, and oxygen;

$R_7$ is straight or branched chain alkyl having from 1 to 10 carbons;

$R_3$ is a phosphorus protecting group;

$X_3$ is —CH($Z_1$)— or a group of Formula XI:

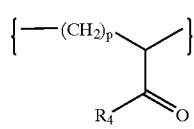

$Z_1$ is the sidechain of a naturally occurring amino acid, or a protected sidechain of a naturally occurring amino acid;

p is 1 or 2; and $R_5$ is H or an amino protecting group.

30. The compound of claim 29 wherein $X_3$ has the Formula XI.

31. The compound of claim 30, wherein p is 2.

32. The compound of claim 31, wherein $W_1$ is —O—(CH$_2$)$_n$—NH— where n is from 1 to about 10.

33. The compound of claim 32 wherein n is 6.

34. A synthetic method comprising the steps of:

(a) providing a compound of Formula IA, IB, IC or ID:

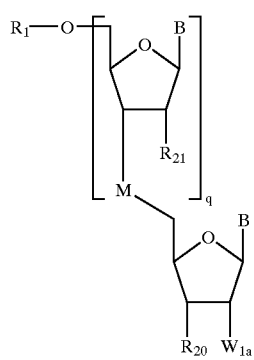

IA

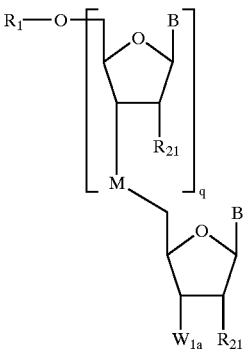

IB

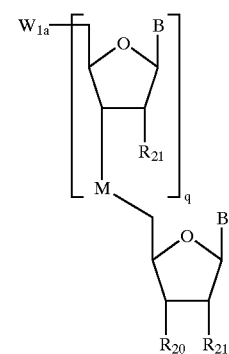

IC

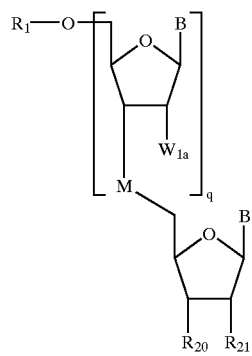

ID wherein:
$W_{1a}$ is $W_{1b}$—H, OH, NH$_2$ or SH, where $W_{1b}$ is a linking group;
$R_1$ is H or a hydroxyl protecting group;
B is a nucleobase;
$R_{20}$ is a group of Formula:

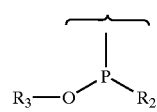

each $R_{21}$ is H, OH, F, or a group of formula Z—$R_{22}$—($R_{23}$)$_v$;
Z is O, S, NH, or N—$R_{22}$—($R_{23}$)$_v$
$R_{22}$ is $C_1$–$C_{20}$ alkyl, $C_2$–$C_{20}$ alkenyl, or $C_2$–$C_{20}$ alkynyl;

R$_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10;

or R$_{21}$ has one of the formulas:

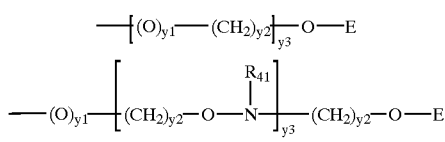

wherein:

y1 is 0 or 1;

y2 is 0 to 10;

y3 is 1 to 10;

E is N(R$_{41}$)(R$_{42}$) or N=C(R$_{41}$)(R$_{42}$);

each R$_{41}$ and each R$_{42}$ is independently H, C$_1$–C$_{10}$ alkyl, a nitrogen protecting group, or R$_{41}$ and R$_{42}$ taken together form a nitrogen protecting group; or R$_{41}$ and R$_{42}$ taken together with the N or C atom to which they are attached form a ring structure that can include at least one heteroatom selected from N and O;

q is 0 to about 50, provided that when said compound has formula ID, q is at least 1;

M is an optionally protected internucleoside linkage;

(b) reacting said compound of Formula I with a compound of Formula II:

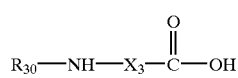

II wherein:

R$_{30}$ is an amino protecting group;

X$_3$ is —CH(Z$_1$)— or a group of Formula XI:

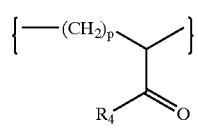

XI

Z$_1$ is the sidechain of a naturally occurring amino acid, or a protected sidechain of a naturally occurring amino acid;

p is 1 or 2;

to form a compound of Formula IVA, IVB, IVC, or IVD:

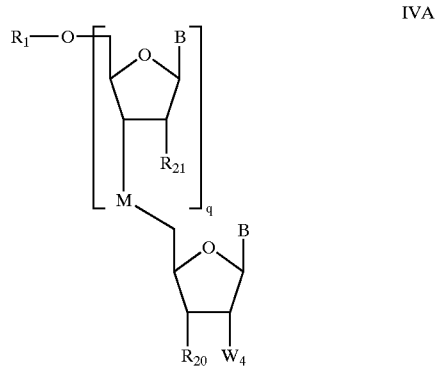

IVA

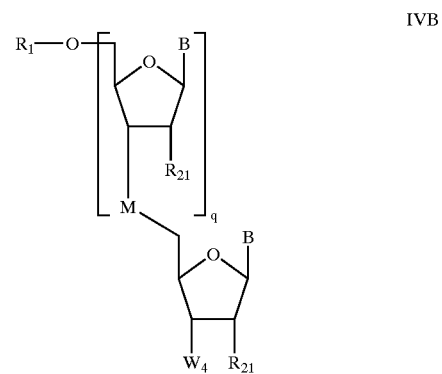

IVB

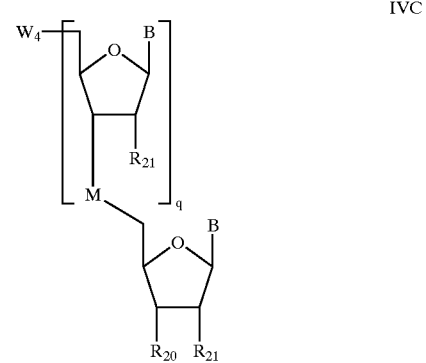

IVC

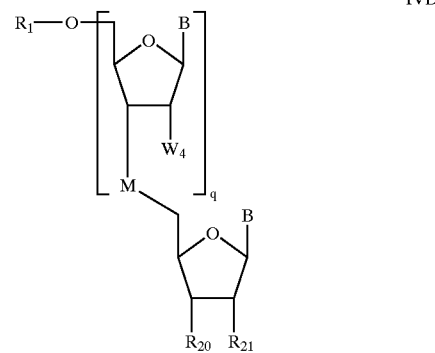

IVD wherein:

W$_4$ has the formula:

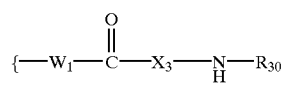

wherein W$_1$ is a linking group, O, NH or S; and
treating said compound of Formula IVA, IVB, IVC or IVD with a deprotecting reagent to form a compound of Formula VA, VB, VC or VD:

VA

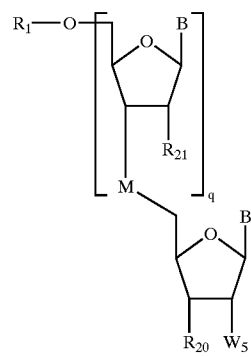

VB

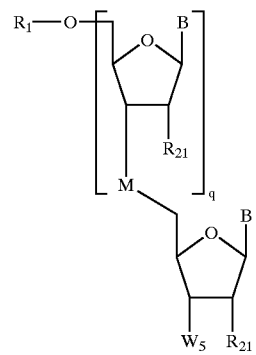

VC

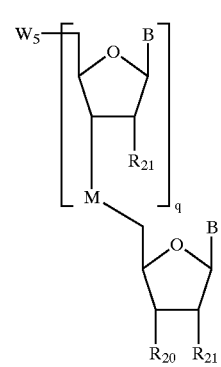

VD

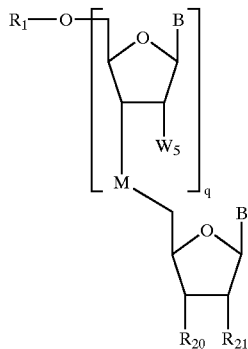

where W$_5$ has the Formula:

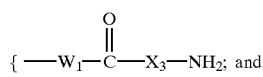

(c) condensing said compound of Formula V with a compound of Formula VI:

VI

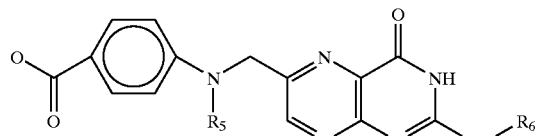

wherein:

R$_5$ is H or an amino protecting group;

R$_6$ is H or an amino protecting group;

to form a compound of Formula VIIA, VIIB, VIIC, or VIID:

VIIA

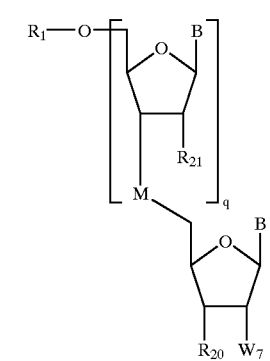

-continued

VIIB
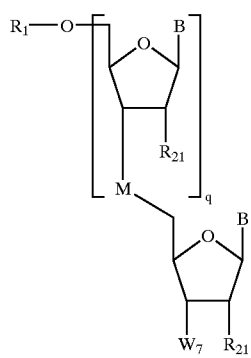

VIIC
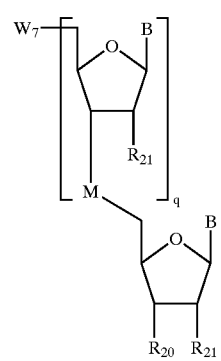

VIID
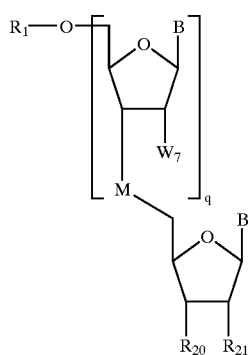

wherein $W_7$ has the Formula:

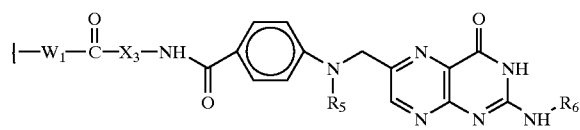

35. The method of claim 14 wherein $X_3$ is a group of Formula XI:

XI
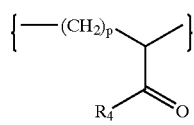

wherein:

p is 1 or 2;

$R_4$ is a hydroxyl group, or a protected hydroxy group;

or $X_3$ is a group of Formula XII:

XII
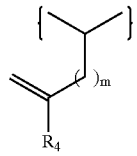

wherein m is 1 or 2.

36. The method of claim 35 wherein q is 0.

37. The method of claim 35 wherein $R_{30}$ is fluornene-9-yl methoxycarbonyl.

38. The method of claim 35 wherein $X_3$ is a group of Formula XI.

39. The method of claim 35 wherein $W_1$ has the formula —O—$(CH_2)_n$—NH—, where n is from 1 to about 10.

40. The method of claim 38 wherein $R_1$ is dimethoxytrityl, $W_1$ has the formula —O—$(CH_2)_n$—NH— where n is 6, p is 2, $R_4$ is t-butoxy, $R_5$ is trifluoroacetoyl, $R_6$ is —C(=O)—CH$(CH_3)_2$, and $R_{30}$ is FMOX.

41. The method of claim 39 wherein n is 6.

42. A compound having the Formula XIIIA, XIIIB, or XIIIC:

XIIIA
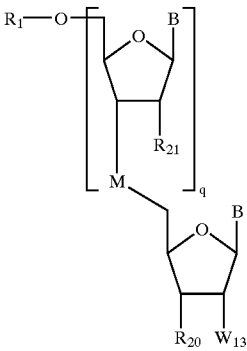

XIIIB
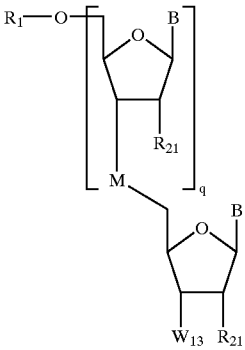

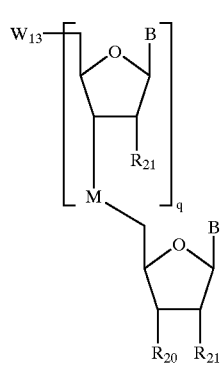

XIIIC wherein:

$W_{13}$ has the Formula:

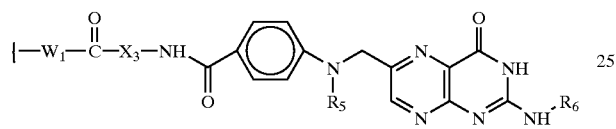

$R_1$ is H or a hydroxyl protecting group;

B is a nucleobase;

each $R_{21}$ is H, OH, F, or a group of formula Z—$R_{22}$—$(R_{23})_v$;

Z is O, S, NH or N—$R_{22}$—$(R_{23})_v$;

$R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_{21}$ has one of the formulas:

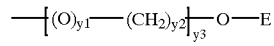

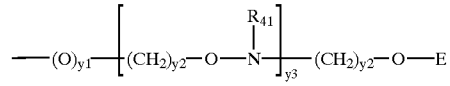

wherein:

y1 is 0 or 1;

y2 is 0 to 10;

y3 is 1 to 10;

E is $N(R_{41})(R_{42})$ or $N=C(R_{41})(R_{42})$;

each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O;

v is from 0 to about 10;

q is 0;

M is an optionally protected internucleoside linkage;

$W_1$ is a linking group, O, NH or S;

$R_{20}$ is OH or a group of Formula:

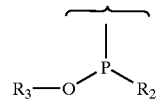

$R_2$ is —$N(R_7)_2$, or a heterocycloalkyl or heterocycloalkenyl ring containing from 4 to 7 atoms, and having up to 3 heteroatoms selected from nitrogen, sulfur, and oxygen;

$R_7$ is straight or branched chain alkyl having from 1 to 10 carbons;

$R_3$ is a phosphorus protecting group;

$R_5$ is H or an amino protecting group;

$R_6$ is H or an amino protecting group;

$X_3$ is —$CH(Z_1)$— or a group of Formula XI:

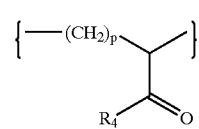

XI $Z_1$ is the sidechain of a naturally occurring amino acid, or a protected sidechain of a naturally occurring amino acid;

p is 1 or 2; and $R_4$ is a hydroxyl group, or a protected hydroxyl group.

* * * * *

UNITED STATES PATENT AND TRADEMARK OFFICE
CERTIFICATE OF CORRECTION

PATENT NO. : 6,528,631 B1
DATED : March 4, 2003
INVENTOR(S) : Cook et al.

It is certified that error appears in the above-identified patent and that said Letters Patent is hereby corrected as shown below:

Column 61,
Lines 60 through 64, delete the Formula: 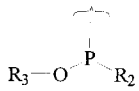 and replace with: 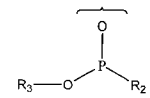

Column 62,
Lines 39 through 44, delete the Formula: 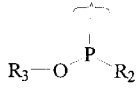 and replace with: 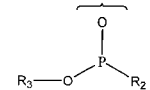

Column 63,
Line 64, please add -- O -- before the letter "H".

Column 65,
Lines 56 through 60, delete the Formula: 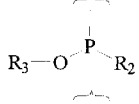 and replace with: 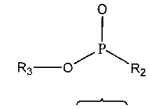

Column 68,
Lines 10 through 14, delete the Formula: 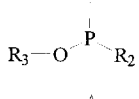 and replace with: 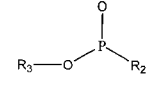

Column 70,
Lines 33 through 38, delete the Formula: 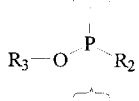 and replace with: 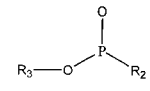

Column 75,
Lines 26 through 30, delete the Formula: 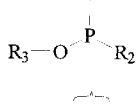 and replace with: 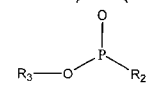

Column 80,
Lines 44 through 49, delete the Formula: 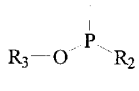 and replace with: 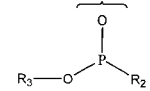

Column 83,
Lines 6 through 10, delete the Formulas:

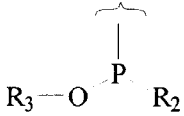   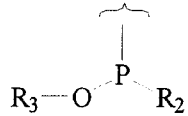

and replace with the following Formula:

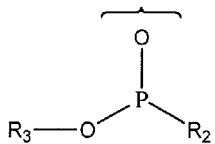

UNITED STATES PATENT AND TRADEMARK OFFICE
CERTIFICATE OF CORRECTION

PATENT NO. : 6,528,631 B1
DATED : March 4, 2003
INVENTOR(S) : Cook et al.

It is certified that error appears in the above-identified patent and that said Letters Patent is hereby corrected as shown below:

Column 84,
Lines 57 through 62, delete the Formula: 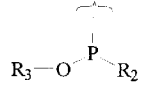 and replace with: 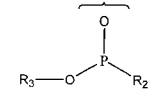

Column 92,
Lines 23 through 27, delete the Formula: 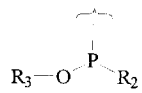 and replace with: 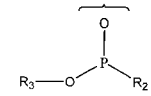

Signed and Sealed this

Thirtieth Day of December, 2003

JAMES E. ROGAN
*Director of the United States Patent and Trademark Office*